US008845699B2

(12) United States Patent
Bonutti

(10) Patent No.: US 8,845,699 B2
(45) Date of Patent: Sep. 30, 2014

(54) METHOD OF SECURING TISSUE

(75) Inventor: Peter M. Bonutti, Effingham, IL (US)

(73) Assignee: Bonutti Skeletal Innovations LLC, Plano, TX (US)

( * ) Notice: Subject to any disclaimer, the term of this patent is extended or adjusted under 35 U.S.C. 154(b) by 0 days.

(21) Appl. No.: 13/413,393

(22) Filed: Mar. 6, 2012

(65) Prior Publication Data

US 2012/0165841 A1 Jun. 28, 2012

Related U.S. Application Data

(63) Continuation of application No. 11/067,911, filed on Feb. 28, 2005, now Pat. No. 8,128,669, which is a continuation of application No. 10/007,360, filed on Oct. 29, 2001, now Pat. No. 6,860,885, which is a continuation of application No. 09/370,865, filed on Aug. 9, 1999, now Pat. No. 6,447,516.

(51) Int. Cl.
*A61B 17/04* (2006.01)
*A61B 17/68* (2006.01)
*A61F 2/08* (2006.01)

(52) U.S. Cl.
CPC ............... *A61B 17/68* (2013.01); *A61F 2/0811* (2013.01); *A61B 17/0401* (2013.01); *A61B 2017/0414* (2013.01); *Y10S 606/902* (2013.01); *A61F 2/0805* (2013.01)
USPC ........................... 606/300; 606/304; 606/902

(58) Field of Classification Search
USPC ......... 606/300–321, 86 R, 96–100, 104, 105, 606/62–68
See application file for complete search history.

(56) References Cited

U.S. PATENT DOCUMENTS 157,343 A 12/1874 Molesworth
319,296 A 6/1885 Molesworth
(Continued)

FOREIGN PATENT DOCUMENTS

CA 1312518 C 1/1993
CA 2641580 8/2007
(Continued)

OTHER PUBLICATIONS

David E. Taylor et al., Technical Note, entitled: Femoral Bone Plug Recession in Endoscopic Anterior Cruciate Ligament Reconstruction, Arthroscopy: The Journal of Arthroscopic and Related Surgery, vol. 12, No. 4, Aug. 1996: pp. 513-515.

(Continued)

*Primary Examiner* — Jerry Cumberledge
*Assistant Examiner* — Tara Carter
(74) *Attorney, Agent, or Firm* — Martin & Ferraro, LLP

(57) ABSTRACT

A retainer member formed of bone secures tissue relative to a bone. The retainer member forms an opening in a compact outer layer of the bone. The retainer member is enclosed in a tubular member or sleeve to prevent breaking of the retainer member during formation of the opening in the bone. The extent of movement of the retainer member into the hone in the patient's body is determined as the retainer member is moved into the bone. A suture may be connected with the retainer member and used to connect tissue with the bone. The retainer member may be positioned across a fracture in a bone to hold portions of the hone relative to each other. The retainer member may be used at a joint between end portions of bones to immobilize the joint and be released by breaking the retainer member.

28 Claims, 6 Drawing Sheets

(56) References Cited

U.S. PATENT DOCUMENTS

| | | |
|---|---|---|
| 668,878 A | 2/1901 | Jensen |
| 668,879 A | 2/1901 | Miller |
| 673,783 A | 5/1901 | Peters |
| 702,789 A | 6/1902 | Gibson |
| 832,201 A | 10/1906 | Kistler |
| 862,712 A | 8/1907 | Collins |
| 1,213,005 A | 1/1917 | Pilllsbury |
| 1,433,031 A | 10/1922 | Henri |
| 1,725,670 A | 8/1929 | Novack |
| 1,863,057 A | 6/1932 | Innes |
| 1,870,942 A | 8/1932 | Beatty |
| 2,121,193 A | 12/1932 | Hanicke |
| 1,909,967 A | 5/1933 | Jones |
| 1,959,615 A | 5/1934 | Derrah |
| 2,187,852 A | 8/1936 | Friddle |
| 2,178,840 A | 11/1939 | Libarid |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,433,815 A | 12/1947 | Nicephore et al. |
| 2,518,276 A | 8/1950 | Braward |
| 2,526,662 A | 10/1950 | Hipps et al. |
| 2,557,669 A | 6/1951 | Lloyd |
| 2,566,499 A | 9/1951 | Richter |
| 2,589,720 A | 3/1952 | McMath |
| 2,621,145 A | 12/1952 | Sano |
| 2,621,653 A | 12/1952 | Briggs |
| 2,642,874 A | 6/1953 | Keeling |
| 2,687,719 A | 8/1954 | Hoyt |
| 2,701,559 A | 2/1955 | Cooper |
| 2,724,326 A | 11/1955 | Long |
| 2,725,053 A | 11/1955 | Bambara |
| 2,830,587 A | 4/1958 | Everett |
| 2,854,983 A | 10/1958 | Baskin |
| 2,936,760 A | 5/1960 | Gants |
| 2,955,530 A | 10/1960 | Nilo |
| 3,039,468 A | 6/1962 | Price |
| 3,048,522 A | 8/1962 | Velley |
| 3,081,773 A | 3/1963 | Boyd |
| 3,108,357 A | 10/1963 | Liebig |
| 3,108,595 A | 10/1963 | Overment |
| 3,204,635 A | 9/1965 | Voss et al. |
| 3,229,006 A | 1/1966 | Nohl |
| 3,253,594 A | 5/1966 | Matthews et al. |
| 3,347,234 A | 10/1967 | Voss |
| 3,367,809 A | 2/1968 | Soloff |
| 3,391,690 A | 7/1968 | Armao |
| 3,397,699 A | 8/1968 | Kohl |
| 3,417,745 A | 12/1968 | Emanuel |
| 3,459,175 A | 8/1969 | Miller |
| 3,469,003 A | 9/1969 | Hardy |
| 3,477,429 A | 11/1969 | Sampson |
| 3,495,586 A | 2/1970 | Regenbogen |
| 3,513,848 A | 5/1970 | Winston et al. |
| 3,514,791 A | 6/1970 | Sparks |
| 3,517,128 A | 6/1970 | Hines |
| 3,518,993 A | 7/1970 | Blake |
| 3,554,192 A | 1/1971 | Isberner |
| 3,557,794 A | 1/1971 | Patten |
| 3,577,991 A | 5/1971 | Wilkinson |
| 3,593,709 A | 7/1971 | Halloran |
| 3,596,292 A | 8/1971 | Erb et al. |
| 3,608,539 A | 9/1971 | Miller |
| 3,613,497 A | 10/1971 | Heldermann |
| 3,620,218 A | 11/1971 | Schmitt et al. |
| 3,624,747 A | 11/1971 | McKnight et al. |
| 3,625,220 A | 12/1971 | Engelsher |
| 3,626,949 A | 12/1971 | Shute |
| 3,635,223 A | 1/1972 | Klieman |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,670,732 A | 6/1972 | Robinson |
| 3,678,980 A | 7/1972 | Gutshall |
| 3,698,017 A | 10/1972 | Scales et al. |
| 3,709,218 A | 1/1973 | Halloran |
| 3,711,347 A | 1/1973 | Wagner et al. |
| 3,716,051 A | 2/1973 | Fischer |
| 3,721,244 A | 3/1973 | Elmaleh |
| 3,739,773 A | 6/1973 | Schmitt et al. |
| 3,750,652 A | 8/1973 | Sherwin |
| 3,760,808 A | 9/1973 | Bleuer |
| 3,769,980 A | 11/1973 | Karman |
| 3,774,244 A | 11/1973 | Walker |
| 3,774,596 A | 11/1973 | Cook |
| 3,779,239 A | 12/1973 | Fischer et al. |
| 3,788,318 A | 1/1974 | Kim et al. |
| 3,789,852 A | 2/1974 | Kim et al. |
| 3,800,788 A | 4/1974 | White |
| 3,802,438 A | 4/1974 | Wolvek |
| 3,804,089 A | 4/1974 | Bridgman |
| 3,807,393 A | 4/1974 | McDonald |
| 3,807,394 A | 4/1974 | Attenborough |
| 3,809,075 A | 5/1974 | Matles |
| 3,811,449 A | 5/1974 | Gravlee et al. |
| 3,812,855 A | 5/1974 | Banko |
| 3,825,010 A | 7/1974 | McDonald |
| 3,833,003 A | 9/1974 | Taricco |
| 3,835,849 A | 9/1974 | McGuire |
| 3,841,304 A | 10/1974 | Jones |
| 3,842,824 A | 10/1974 | Neufeld |
| 3,845,772 A | 11/1974 | Smith |
| 3,850,172 A | 11/1974 | Cazalis |
| 3,850,720 A | 11/1974 | Collins |
| 3,852,830 A | 12/1974 | Marmor |
| 3,857,396 A | 12/1974 | Hardwick |
| 3,863,639 A | 2/1975 | Kleaveland |
| 3,867,932 A | 2/1975 | Huene |
| 3,869,731 A | 3/1975 | Waugh et al. |
| 3,874,264 A | 4/1975 | Polos |
| 3,875,652 A | 4/1975 | Arnold |
| 3,875,946 A | 4/1975 | Duncan |
| 3,882,852 A | 5/1975 | Sinnreich |
| 3,889,686 A | 6/1975 | Duturbure et al. |
| 3,894,530 A | 7/1975 | Dardik et al. |
| 3,898,992 A | 8/1975 | Balamuth |
| 3,903,549 A | 9/1975 | Deyerle |
| 3,911,923 A | 10/1975 | Yoon |
| 3,915,171 A | 10/1975 | Shermeta |
| 3,918,442 A | 11/1975 | Nikolaev et al. |
| 3,920,022 A | 11/1975 | Pastor |
| 3,939,835 A | 2/1976 | Bridgman |
| 3,945,375 A | 3/1976 | Banko |
| 3,960,143 A | 6/1976 | Terada |
| 3,961,632 A | 6/1976 | Moossun |
| 3,967,625 A | 7/1976 | Yoon |
| 3,968,800 A | 7/1976 | Vilasi |
| 3,970,089 A | 7/1976 | Saice |
| 3,973,277 A | 8/1976 | Semple et al. |
| 3,976,079 A | 8/1976 | Samuels et al. |
| 3,989,049 A | 11/1976 | Yoon |
| 3,991,426 A | 11/1976 | Flom et al. |
| 3,994,287 A | 11/1976 | Turp et al. |
| 4,000,525 A | 1/1977 | Klawitter et al. |
| 4,022,216 A | 5/1977 | Stevens |
| 4,023,559 A | 5/1977 | Gaskell |
| 4,040,413 A | 8/1977 | Ohshiro |
| 4,053,953 A | 10/1977 | Flom et al. |
| 4,055,862 A | 11/1977 | Farling |
| 4,064,566 A | 12/1977 | Fletcher et al. |
| 4,077,412 A | 3/1978 | Moossun |
| 4,081,866 A | 4/1978 | Upshaw et al. |
| 4,083,369 A | 4/1978 | Sinnreich |
| 4,085,466 A | 4/1978 | Goodfellow et al. |
| 4,085,743 A | 4/1978 | Yoon |
| 4,089,071 A | 5/1978 | Kainberz et al. |
| 4,092,113 A | 5/1978 | Hardy |
| 4,103,680 A | 8/1978 | Yoon |
| RE29,757 E | 9/1978 | Helfet |
| 4,122,605 A | 10/1978 | Hirabayashi et al. |
| 4,142,517 A | 3/1979 | Contreras et al. |
| 4,148,307 A | 4/1979 | Utsugi |

(56) References Cited

U.S. PATENT DOCUMENTS

| | | |
|---|---|---|
| 4,156,574 A | 5/1979 | Boden |
| 4,164,794 A | 8/1979 | Spector et al. |
| 4,169,470 A | 10/1979 | Ender et al. |
| 4,171,544 A | 10/1979 | Hench et al. |
| 4,177,814 A | 12/1979 | Knepshield et al. |
| 4,183,102 A | 1/1980 | Guiset |
| 4,186,448 A | 2/1980 | Brekke |
| 4,191,747 A | 3/1980 | Scheicher |
| 4,198,981 A | 4/1980 | Sinnreich |
| 4,199,864 A | 4/1980 | Ashman |
| 4,200,939 A | 5/1980 | Oser |
| 4,203,444 A | 5/1980 | Bonnell et al. |
| 4,209,012 A | 6/1980 | Smucker |
| 4,209,861 A | 7/1980 | Walker et al. |
| 4,210,148 A | 7/1980 | Stivala |
| 4,210,580 A | 7/1980 | Amrani |
| 4,213,209 A | 7/1980 | Insall et al. |
| 4,213,816 A | 7/1980 | Morris |
| 4,224,696 A | 9/1980 | Murray et al. |
| 4,224,929 A | 9/1980 | Furihata |
| 4,228,802 A | 10/1980 | Trott |
| 4,230,119 A | 10/1980 | Blum |
| 4,235,233 A | 11/1980 | Mouwen |
| 4,235,238 A | 11/1980 | Ogiu et al. |
| 4,240,433 A | 12/1980 | Bordow |
| 4,243,048 A | 1/1981 | Griffin |
| 4,244,370 A | 1/1981 | Furlow et al. |
| 4,257,411 A | 3/1981 | Cho |
| 4,263,900 A | 4/1981 | Nicholson |
| 4,265,231 A | 5/1981 | Scheller, Jr. et al. |
| 4,265,848 A | 5/1981 | Rusch |
| 4,274,414 A | 6/1981 | Johnson et al. |
| 4,281,649 A | 8/1981 | Derweduwen |
| 4,291,698 A | 9/1981 | Fuchs |
| 4,295,464 A | 10/1981 | Shihata |
| 4,298,002 A | 11/1981 | Ronel et al. |
| 4,298,992 A | 11/1981 | Burstein et al. |
| 4,298,998 A | 11/1981 | Naficy |
| 4,299,224 A | 11/1981 | Noiles |
| 4,299,227 A | 11/1981 | Lincoff |
| 4,304,178 A | 12/1981 | Haeberle |
| 4,309,488 A | 1/1982 | Heide et al. |
| 4,311,145 A | 1/1982 | Esty et al. |
| 4,312,353 A | 1/1982 | Shahbabian |
| 4,320,762 A | 3/1982 | Bentov |
| 4,344,193 A | 8/1982 | Kenny |
| 4,349,029 A | 9/1982 | Mott |
| 4,349,921 A | 9/1982 | Kuntz |
| 4,351,069 A | 9/1982 | Ballintyn et al. |
| 4,352,883 A | 10/1982 | Lim |
| 4,357,940 A | 11/1982 | Muller |
| 4,364,381 A | 12/1982 | Sher et al. |
| 4,365,356 A | 12/1982 | Broemer et al. |
| 4,369,768 A | 1/1983 | Vukovic |
| 4,373,217 A | 2/1983 | Draenert |
| 4,373,709 A | 2/1983 | Whitt |
| 4,374,523 A | 2/1983 | Yoon |
| 4,385,404 A | 5/1983 | Sully et al. |
| 4,388,921 A | 6/1983 | Sutter et al. |
| 4,391,909 A | 7/1983 | Lim |
| 4,395,798 A | 8/1983 | McVey |
| 4,400,833 A | 8/1983 | Kurland |
| 4,407,273 A | 10/1983 | Ouchi |
| 4,409,974 A | 10/1983 | Freedland |
| 4,414,166 A | 11/1983 | Charlson et al. |
| 4,421,112 A | 12/1983 | Mains et al. |
| 4,430,760 A | 2/1984 | Smestad |
| 4,434,797 A | 3/1984 | Silander |
| 4,437,191 A | 3/1984 | Van der Zat et al. |
| 4,437,362 A | 3/1984 | Hurst |
| 4,442,655 A | 4/1984 | Stroetmann et al. |
| 4,444,180 A | 4/1984 | Schneider et al. |
| 4,445,509 A | 5/1984 | Auth |
| 4,447,227 A | 5/1984 | Kotsanis |
| 4,448,194 A | 5/1984 | DiGiovanni et al. |
| 4,450,591 A | 5/1984 | Rappaport |
| 4,453,421 A | 6/1984 | Umano |
| 4,453,539 A | 6/1984 | Raftopoulos et al. |
| 4,456,005 A | 6/1984 | Lichty |
| 4,457,302 A | 7/1984 | Caspari et al. |
| 4,461,281 A | 7/1984 | Carson |
| 4,466,429 A | 8/1984 | Loscher et al. |
| 4,466,888 A | 8/1984 | Verkaart |
| 4,472,840 A | 9/1984 | Jefferies |
| 4,474,177 A | 10/1984 | Whiteside |
| 4,484,579 A | 11/1984 | Meno et al. |
| 4,485,096 A | 11/1984 | Bell |
| 4,487,203 A | 12/1984 | Androphy |
| 4,493,317 A | 1/1985 | Klaue |
| 4,495,664 A | 1/1985 | Blanquaert |
| 4,501,031 A | 2/1985 | McDaniel et al. |
| 4,501,266 A | 2/1985 | McDaniel |
| 4,501,269 A | 2/1985 | Bagby |
| 4,502,159 A | 3/1985 | Woodroof et al. |
| 4,502,161 A | 3/1985 | Wall |
| 4,504,268 A | 3/1985 | Herlitze |
| 4,505,274 A | 3/1985 | Speelman |
| 4,506,681 A | 3/1985 | Mundell |
| 4,509,518 A | 4/1985 | McGarry et al. |
| 4,514,125 A | 4/1985 | Stol |
| 4,516,276 A | 5/1985 | Mittelmeier et al. |
| 4,526,173 A | 7/1985 | Sheehan |
| 4,532,926 A | 8/1985 | O'Holla |
| 4,535,757 A | 8/1985 | Webster |
| 4,535,772 A | 8/1985 | Sheehan |
| 4,540,404 A | 9/1985 | Wolvek |
| 4,541,423 A | 9/1985 | Barber |
| 4,543,375 A | 9/1985 | Doebler et al. |
| 4,545,374 A | 10/1985 | Jacobson |
| 4,547,327 A | 10/1985 | Bruins et al. |
| 4,551,135 A | 11/1985 | Gorman et al. |
| 4,553,272 A | 11/1985 | Mears |
| 4,554,686 A | 11/1985 | Baker |
| 4,555,242 A | 11/1985 | Saudagar |
| 4,556,059 A | 12/1985 | Adamson, Jr. |
| 4,556,350 A | 12/1985 | Bernhardt et al. |
| 4,556,391 A | 12/1985 | Tardivel et al. |
| 4,562,598 A | 1/1986 | Kranz |
| 4,565,192 A | 1/1986 | Shapiro |
| 4,566,138 A | 1/1986 | Lewis et al. |
| 4,572,186 A | 2/1986 | Gould et al. |
| 4,573,448 A | 3/1986 | Kambin |
| 4,574,794 A | 3/1986 | Cooke et al. |
| 4,575,371 A | 3/1986 | Nordqvist et al. |
| 4,584,722 A | 4/1986 | Levy et al. |
| 4,585,000 A | 4/1986 | Hershenson |
| 4,589,414 A | 5/1986 | Yoshida et al. |
| 4,589,686 A | 5/1986 | McGrew |
| 4,589,868 A | 5/1986 | Dretler |
| 4,590,928 A | 5/1986 | Hunt et al. |
| 4,597,379 A | 7/1986 | Kihn et al. |
| 4,599,085 A | 7/1986 | Riess et al. |
| 4,601,893 A | 7/1986 | Cardinal |
| 4,603,694 A | 8/1986 | Wheeler |
| 4,606,335 A | 8/1986 | Wedeen |
| 4,608,052 A | 8/1986 | Van Kampen et al. |
| 4,608,965 A | 9/1986 | Anspach, Jr. et al. |
| 4,610,662 A | 9/1986 | Weikl et al. |
| 4,611,593 A | 9/1986 | Fogarty et al. |
| 4,615,717 A | 10/1986 | Neubauer et al. |
| 4,619,391 A | 10/1986 | Sharkany et al. |
| 4,621,640 A | 11/1986 | Mulhollan et al. |
| 4,623,553 A | 11/1986 | Ries et al. |
| 4,624,254 A | 11/1986 | McGarry et al. |
| 4,630,609 A | 12/1986 | Chin |
| 4,632,101 A | 12/1986 | Freedland |
| 4,641,648 A | 2/1987 | Shapiro |
| 4,642,117 A | 2/1987 | Nguyen et al. |
| 4,642,120 A | 2/1987 | Nevo et al. |
| 4,645,503 A | 2/1987 | Lin et al. |
| 4,646,736 A | 3/1987 | Auth |
| 4,646,738 A | 3/1987 | Trott |
| 4,649,918 A | 3/1987 | Pegg et al. |
| 4,651,717 A | 3/1987 | Jakubczak |

(56) References Cited

U.S. PATENT DOCUMENTS

| | | |
|---|---|---|
| 4,651,752 A | 3/1987 | Fuerst |
| 4,654,464 A | 3/1987 | Mittelmeier et al. |
| 4,657,460 A | 4/1987 | Bien |
| 4,657,548 A | 4/1987 | Nichols |
| 4,659,268 A | 4/1987 | Del Mundo et al. |
| 4,662,063 A | 5/1987 | Collins et al. |
| 4,662,068 A | 5/1987 | Polonsky |
| 4,662,372 A | 5/1987 | Sharkany et al. |
| 4,662,887 A | 5/1987 | Turner et al. |
| 4,669,473 A | 6/1987 | Richards et al. |
| 4,678,470 A | 7/1987 | Nashef et al. |
| 4,681,106 A | 7/1987 | Kensey et al. |
| 4,681,107 A | 7/1987 | Kees, Jr. |
| 4,682,598 A | 7/1987 | Beraha |
| 4,685,458 A | 8/1987 | Leckrone |
| 4,685,460 A | 8/1987 | Thornton |
| 4,691,741 A | 9/1987 | Affa et al. |
| 4,696,667 A | 9/1987 | Masch |
| 4,705,040 A | 11/1987 | Mueller et al. |
| 4,706,659 A | 11/1987 | Matthews et al. |
| 4,706,670 A | 11/1987 | Andersen et al. |
| 4,708,139 A | 11/1987 | Dunbar, IV |
| 4,711,233 A | 12/1987 | Brown |
| 4,712,542 A | 12/1987 | Daniel et al. |
| 4,713,076 A | 12/1987 | Draenert |
| 4,713,077 A | 12/1987 | Small |
| 4,714,074 A | 12/1987 | Rey et al. |
| 4,716,893 A | 1/1988 | Fischer et al. |
| 4,716,901 A | 1/1988 | Jackson et al. |
| 4,718,909 A | 1/1988 | Brown |
| 4,718,916 A | 1/1988 | Morscher |
| 4,719,908 A | 1/1988 | Averill et al. |
| 4,721,096 A | 1/1988 | Naughton et al. |
| 4,721,103 A | 1/1988 | Freedland |
| 4,721,104 A | 1/1988 | Kaufman et al. |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,743,229 A | 5/1988 | Chu |
| 4,743,259 A | 5/1988 | Bolander et al. |
| 4,744,364 A | 5/1988 | Kensey |
| 4,747,405 A | 5/1988 | Leckrone |
| 4,749,585 A | 6/1988 | Greco et al. |
| 4,750,488 A | 6/1988 | Wuchinich et al. |
| 4,750,492 A | 6/1988 | Jacobs |
| 4,751,922 A | 6/1988 | Dipietropolo |
| 4,755,184 A | 7/1988 | Silverberg |
| 4,759,350 A | 7/1988 | Dunn et al. |
| 4,768,507 A | 9/1988 | Fischell |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,779,611 A | 10/1988 | Grooters et al. |
| 4,781,182 A | 11/1988 | Purnell et al. |
| 4,781,681 A | 11/1988 | Sharrow et al. |
| 4,781,922 A | 11/1988 | Bone |
| 4,784,133 A | 11/1988 | Mackin |
| 4,789,663 A | 12/1988 | Wallace et al. |
| 4,790,303 A | 12/1988 | Steffee |
| 4,790,819 A | 12/1988 | Li et al. |
| 4,792,336 A | 12/1988 | Hiavacek et al. |
| 4,793,359 A | 12/1988 | Sharrow |
| 4,794,854 A | 1/1989 | Swaim |
| 4,795,467 A | 1/1989 | Piez et al. |
| 4,796,629 A | 1/1989 | Grayzel |
| 4,798,205 A | 1/1989 | Bonomo et al. |
| 4,798,213 A | 1/1989 | Doppelt |
| 4,800,901 A | 1/1989 | Rosenberg |
| 4,801,299 A | 1/1989 | Brendel et al. |
| 4,802,479 A | 2/1989 | Haber et al. |
| 4,817,591 A | 4/1989 | Klaue |
| 4,817,602 A | 4/1989 | Beraha |
| 4,822,224 A | 4/1989 | Carl et al. |
| 4,823,794 A | 4/1989 | Pierce |
| 4,825,857 A | 5/1989 | Kenna |
| 4,828,563 A | 5/1989 | Muller-Lierheim et al. |
| 4,832,025 A | 5/1989 | Coates |
| 4,832,026 A | 5/1989 | Jones |
| 4,832,683 A | 5/1989 | Idemoto et al. |
| 4,834,752 A | 5/1989 | Van Kampen |
| 4,834,757 A | 5/1989 | Brantigan |
| 4,841,960 A | 6/1989 | Garner |
| 4,842,517 A | 6/1989 | Kawahara et al. |
| 4,843,112 A | 6/1989 | Gerhart et al. |
| 4,844,064 A | 7/1989 | Thimsen et al. |
| 4,846,791 A | 7/1989 | Hattler et al. |
| 4,846,812 A | 7/1989 | Walker et al. |
| 4,846,835 A | 7/1989 | Grande |
| 4,857,045 A | 8/1989 | Rydell |
| 4,861,334 A | 8/1989 | Nawaz |
| 4,862,874 A | 9/1989 | Kellner |
| 4,862,882 A | 9/1989 | Venturi et al. |
| 4,862,974 A | 9/1989 | Warren et al. |
| 4,863,472 A | 9/1989 | Tormala et al. |
| 4,867,157 A | 9/1989 | McGurk-Burleson et al. |
| 4,869,242 A | 9/1989 | Galluzzo |
| 4,870,957 A | 10/1989 | Goble et al. |
| 4,875,468 A | 10/1989 | Krauter et al. |
| 4,877,020 A | 10/1989 | Vich |
| 4,880,429 A | 11/1989 | Stone |
| 4,883,048 A | 11/1989 | Purnell et al. |
| 4,883,666 A | 11/1989 | Sabel et al. |
| 4,888,022 A | 12/1989 | Huebsch |
| 4,890,612 A | 1/1990 | Kensey |
| 4,892,552 A | 1/1990 | Ainsworth et al. |
| 4,895,148 A | 1/1990 | Bays et al. |
| 4,898,156 A | 2/1990 | Gatturna et al. |
| 4,899,729 A | 2/1990 | Gill et al. |
| 4,899,743 A | 2/1990 | Nicholson et al. |
| 4,899,744 A | 2/1990 | Fujitsuka et al. |
| 4,901,721 A | 2/1990 | Hakki |
| 4,902,296 A | 2/1990 | Bolander et al. |
| 4,904,259 A | 2/1990 | Itay |
| 4,904,261 A | 2/1990 | Dove |
| 4,909,789 A | 3/1990 | Taguchi |
| 4,911,721 A | 3/1990 | Aendergaten et al. |
| 4,919,667 A | 4/1990 | Richmond |
| 4,921,478 A | 5/1990 | Solano et al. |
| 4,921,479 A | 5/1990 | Grayzel |
| 4,922,897 A | 5/1990 | Sapega et al. |
| 4,923,464 A | 5/1990 | DiPisa, Jr. |
| 4,924,865 A | 5/1990 | Bays et al. |
| 4,924,866 A | 5/1990 | Yoon |
| 4,927,412 A | 5/1990 | Menasche |
| 4,927,421 A | 5/1990 | Goble et al. |
| 4,932,956 A | 6/1990 | Reddy et al. |
| 4,932,959 A | 6/1990 | Horzewski et al. |
| 4,932,960 A | 6/1990 | Green et al. |
| 4,932,973 A | 6/1990 | Gendler |
| 4,935,023 A | 6/1990 | Whiteside et al. |
| 4,935,026 A | 6/1990 | Drews |
| 4,935,028 A | 6/1990 | Drews |
| 4,936,848 A | 6/1990 | Bagby |
| 4,936,852 A | 6/1990 | Kent et al. |
| 4,944,760 A | 7/1990 | Kenna |
| 4,945,625 A | 8/1990 | Winston |
| 4,945,896 A | 8/1990 | Gade |
| 4,946,468 A | 8/1990 | Li |
| 4,950,296 A | 8/1990 | McIntyre |
| 4,950,298 A | 8/1990 | Gustilo et al. |
| 4,952,213 A | 8/1990 | Bowman et al. |
| 4,954,126 A | 9/1990 | Wallsten |
| 4,955,910 A | 9/1990 | Bolesky |
| 4,957,498 A | 9/1990 | Caspari et al. |
| 4,961,740 A | 10/1990 | Ray et al. |
| 4,961,741 A | 10/1990 | Hayhurst |
| 4,961,954 A | 10/1990 | Goldberg et al. |
| 4,963,151 A | 10/1990 | Ducheyne et al. |
| 4,963,489 A | 10/1990 | Naughton et al. |
| 4,964,862 A | 10/1990 | Arms |

(56) References Cited

U.S. PATENT DOCUMENTS

| | | |
|---|---|---|
| 4,964,865 A | 10/1990 | Burkhead et al. |
| 4,966,583 A | 10/1990 | Debbas |
| 4,968,298 A | 11/1990 | Michelson |
| 4,968,315 A | 11/1990 | Gatturna |
| 4,969,888 A | 11/1990 | Scholten et al. |
| 4,969,892 A | 11/1990 | Burton et al. |
| 4,969,895 A | 11/1990 | McLeod et al. |
| 4,979,949 A | 12/1990 | Matsen, III et al. |
| 4,979,957 A | 12/1990 | Hodorek |
| 4,983,179 A | 1/1991 | Sjostrom |
| 4,984,563 A | 1/1991 | Renaud |
| 4,984,564 A | 1/1991 | Yuen |
| 4,985,038 A | 1/1991 | Lyell |
| 4,990,161 A | 2/1991 | Kampner |
| 4,994,047 A | 2/1991 | Walker et al. |
| 4,994,067 A | 2/1991 | Summers |
| 4,994,071 A | 2/1991 | MacGregor |
| 4,995,868 A | 2/1991 | Brazier |
| 4,997,445 A | 3/1991 | Hodorek |
| 4,998,539 A | 3/1991 | Delsanti |
| 5,002,550 A | 3/1991 | Li |
| 5,002,557 A | 3/1991 | Hasson |
| 5,002,563 A | 3/1991 | Pyka et al. |
| 5,007,912 A | 4/1991 | Albrektsson et al. |
| 5,009,652 A | 4/1991 | Morgan et al. |
| 5,009,662 A | 4/1991 | Wallace et al. |
| 5,009,663 A | 4/1991 | Broome |
| 5,009,664 A | 4/1991 | Sievers |
| 5,013,316 A | 5/1991 | Goble et al. |
| 5,015,247 A | 5/1991 | Michelson |
| 5,015,255 A | 5/1991 | Kuslich |
| 5,019,090 A | 5/1991 | Pinchuk |
| 5,019,104 A | 5/1991 | Whiteside et al. |
| 5,021,056 A | 6/1991 | Hofmann et al. |
| 5,021,059 A | 6/1991 | Kensey et al. |
| 5,026,373 A | 6/1991 | Ray et al. |
| 5,027,827 A | 7/1991 | Cody et al. |
| 5,032,132 A | 7/1991 | Matsen, III et al. |
| 5,035,699 A | 7/1991 | Coates |
| 5,035,713 A | 7/1991 | Friis |
| 5,037,404 A | 8/1991 | Gold et al. |
| 5,037,422 A | 8/1991 | Hayhurst et al. |
| 5,037,423 A | 8/1991 | Kenna |
| 5,041,093 A | 8/1991 | Chu |
| 5,041,114 A | 8/1991 | Chapman et al. |
| 5,041,125 A | 8/1991 | Montano, Jr. |
| 5,041,129 A | 8/1991 | Hayhurst et al. |
| 5,042,976 A | 8/1991 | Ishitsu et al. |
| 5,046,513 A | 9/1991 | Gatturna et al. |
| 5,047,055 A | 9/1991 | Bao et al. |
| 5,051,049 A | 9/1991 | Wills |
| 5,053,009 A | 10/1991 | Herzberg |
| 5,053,039 A | 10/1991 | Hofmann et al. |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,060,678 A | 10/1991 | Bauman et al. |
| 5,061,274 A | 10/1991 | Kensey |
| 5,061,281 A | 10/1991 | Mares et al. |
| 5,061,286 A | 10/1991 | Lyle |
| 5,062,843 A | 11/1991 | Mahony, III |
| 5,069,674 A | 12/1991 | Fearnot et al. |
| 5,071,411 A | 12/1991 | Hillstead |
| 5,073,373 A | 12/1991 | O'Leary et al. |
| 5,078,731 A | 1/1992 | Hayhurst |
| 5,078,744 A | 1/1992 | Chvapil |
| 5,078,745 A | 1/1992 | Rhenter et al. |
| 5,082,670 A | 1/1992 | Gage et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,092,348 A | 3/1992 | Dubrul et al. |
| 5,098,433 A | 3/1992 | Freedland |
| 5,098,434 A | 3/1992 | Serbousek |
| 5,098,436 A | 3/1992 | Ferrante et al. |
| 5,098,437 A | 3/1992 | Kashuba et al. |
| 5,099,859 A | 3/1992 | Bell |
| 5,100,405 A | 3/1992 | McLaren |
| 5,100,409 A | 3/1992 | Coates et al. |
| 5,100,417 A | 3/1992 | Cerier et al. |
| 5,100,689 A | 3/1992 | Goldberg et al. |
| 5,101,720 A | 4/1992 | Bianchi |
| 5,102,417 A | 4/1992 | Palmaz |
| 5,102,421 A | 4/1992 | Anspach, Jr. |
| 5,104,383 A | 4/1992 | Shichman |
| 5,108,399 A | 4/1992 | Eitenmuller et al. |
| 5,108,433 A | 4/1992 | May et al. |
| 5,108,441 A | 4/1992 | McDowell |
| 5,111,987 A | 5/1992 | Moeinzadeh et al. |
| 5,116,374 A | 5/1992 | Stone |
| 5,120,175 A | 6/1992 | Arbegast et al. |
| 5,122,122 A | 6/1992 | Allgood |
| 5,122,144 A | 6/1992 | Bert et al. |
| 5,123,520 A | 6/1992 | Schmid et al. |
| 5,123,906 A | 6/1992 | Kelman |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller |
| 5,135,522 A | 8/1992 | Fahrenkrug et al. |
| 5,139,520 A | 8/1992 | Rosenberg |
| 5,141,520 A | 8/1992 | Goble et al. |
| 5,143,062 A | 9/1992 | Peckham |
| 5,143,093 A | 9/1992 | Sahota |
| 5,147,362 A | 9/1992 | Goble |
| 5,152,744 A | 10/1992 | Krause et al. |
| 5,152,765 A | 10/1992 | Ross et al. |
| 5,152,778 A | 10/1992 | Bales, Jr. et al. |
| 5,154,717 A | 10/1992 | Matsen, III et al. |
| 5,154,720 A | 10/1992 | Trott et al. |
| 5,156,613 A | 10/1992 | Sawyer |
| 5,156,616 A | 10/1992 | Meadows et al. |
| 5,158,553 A | 10/1992 | Berry et al. |
| 5,158,566 A | 10/1992 | Pianetti |
| 5,158,571 A | 10/1992 | Picha |
| 5,158,934 A | 10/1992 | Ammann et al. |
| 5,159,921 A | 11/1992 | Hoover |
| 5,162,506 A | 11/1992 | Hadden |
| 5,163,949 A | 11/1992 | Bonutti |
| 5,163,960 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,251 A | 12/1992 | Bregen et al. |
| 5,171,276 A | 12/1992 | Caspari et al. |
| 5,174,300 A | 12/1992 | Bales et al. |
| 1,312,518 A | 1/1993 | Hayhurst |
| 5,176,682 A | 1/1993 | Chow |
| 5,176,684 A | 1/1993 | Ferrante et al. |
| 5,176,702 A | 1/1993 | Bales et al. |
| 5,178,622 A | 1/1993 | Lehner, II |
| 5,179,964 A | 1/1993 | Cook |
| 5,180,388 A | 1/1993 | DiCarlo |
| 5,183,053 A | 2/1993 | Yeh et al. |
| 5,183,464 A | 2/1993 | Dubrul et al. |
| 5,185,001 A | 2/1993 | Galanakis |
| 5,186,178 A | 2/1993 | Yeh et al. |
| 5,192,287 A | 3/1993 | Fournier et al. |
| 5,192,326 A | 3/1993 | Bao et al. |
| 5,192,327 A | 3/1993 | Brantigan |
| 5,195,507 A | 3/1993 | Bilweis |
| 5,195,970 A | 3/1993 | Gahara |
| 5,197,166 A | 3/1993 | Meier et al. |
| 5,197,488 A | 3/1993 | Kovacevic |
| 5,197,955 A | 3/1993 | Stephens et al. |
| 5,197,968 A | 3/1993 | Clement |
| 5,197,971 A | 3/1993 | Bonutti |
| 5,197,987 A | 3/1993 | Koch et al. |
| 5,201,768 A | 4/1993 | Caspari et al. |
| 5,203,784 A | 4/1993 | Ross et al. |
| 5,203,787 A | 4/1993 | Noblitt et al. |
| 5,204,106 A | 4/1993 | Schepers et al. |

(56) References Cited

U.S. PATENT DOCUMENTS

| | | |
|---|---|---|
| 5,207,692 A | 5/1993 | Kraus et al. |
| 5,208,950 A | 5/1993 | Merritt |
| 5,209,776 A | 5/1993 | Bass et al. |
| 5,211,647 A | 5/1993 | Schmieding |
| 5,217,463 A | 6/1993 | Mikhail |
| 5,217,486 A | 6/1993 | Rice et al. |
| 5,217,493 A | 6/1993 | Raad et al. |
| 5,219,359 A | 6/1993 | McQuilkin et al. |
| 5,224,946 A | 7/1993 | Hayhurst et al. |
| 5,226,426 A | 7/1993 | Yoon |
| 5,226,877 A | 7/1993 | Epstein |
| 5,226,899 A | 7/1993 | Lee et al. |
| 5,226,915 A | 7/1993 | Bertin |
| 5,228,459 A | 7/1993 | Caspari et al. |
| 5,234,006 A | 8/1993 | Eaton et al. |
| 5,234,425 A | 8/1993 | Fogarty et al. |
| 5,234,433 A | 8/1993 | Bert et al. |
| 5,236,432 A | 8/1993 | Matsen, III et al. |
| 5,236,438 A | 8/1993 | Wilk |
| 5,236,445 A | 8/1993 | Hayhurst et al. |
| 5,242,902 A | 9/1993 | Murphy et al. |
| 5,244,946 A | 9/1993 | Guest et al. |
| 5,246,441 A | 9/1993 | Ross et al. |
| 5,250,026 A | 10/1993 | Ehrlich et al. |
| 5,250,055 A | 10/1993 | Moore et al. |
| 5,250,070 A | 10/1993 | Parodi |
| 5,254,091 A | 10/1993 | Aliahmad et al. |
| 5,254,113 A | 10/1993 | Wilk |
| 5,258,004 A | 11/1993 | Bales et al. |
| 5,258,007 A | 11/1993 | Spetzler et al. |
| 5,258,015 A | 11/1993 | Li et al. |
| 5,258,016 A | 11/1993 | DiPoto et al. |
| 5,258,031 A | 11/1993 | Salib et al. |
| 5,258,032 A | 11/1993 | Bertin |
| 5,261,914 A | 11/1993 | Warren |
| 5,263,498 A | 11/1993 | Caspari et al. |
| 5,263,987 A | 11/1993 | Shah |
| 5,266,325 A | 11/1993 | Kuzma et al. |
| 5,268,001 A | 12/1993 | Nicholson et al. |
| 5,269,783 A | 12/1993 | Sander |
| 5,269,785 A | 12/1993 | Bonutti |
| 5,269,809 A | 12/1993 | Hayhurst et al. |
| 5,273,524 A | 12/1993 | Fox et al. |
| 5,275,166 A | 1/1994 | Vaitekunas et al. |
| 5,281,235 A | 1/1994 | Haber et al. |
| 5,282,803 A | 2/1994 | Lackey |
| 5,282,832 A | 2/1994 | Toso et al. |
| 5,282,861 A | 2/1994 | Kaplan |
| 5,284,655 A | 2/1994 | Bogdansky et al. |
| 5,285,655 A | 2/1994 | Sung-Il et al. |
| 5,290,249 A | 3/1994 | Foster et al. |
| 5,290,281 A | 3/1994 | Tschakaloff |
| 5,298,254 A | 3/1994 | Prewett et al. |
| 2,696,338 A | 4/1994 | Perrin |
| 5,304,119 A | 4/1994 | Balaban et al. |
| 5,304,181 A | 4/1994 | Caspari et al. |
| 5,306,280 A | 4/1994 | Bregen et al. |
| 5,306,301 A | 4/1994 | Graf et al. |
| 5,312,438 A | 5/1994 | Johnson |
| 5,315,741 A | 5/1994 | Dubberke |
| 5,318,588 A | 6/1994 | Horzewski et al. |
| 5,320,611 A | 6/1994 | Bonutti et al. |
| 5,322,505 A | 6/1994 | Krause et al. |
| 5,324,308 A | 6/1994 | Pierce |
| 5,326,361 A | 7/1994 | Hollister |
| 5,328,480 A | 7/1994 | Melker et al. |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot et al. |
| 5,330,486 A | 7/1994 | Wilk |
| 5,330,497 A | 7/1994 | Freitas et al. |
| 5,331,975 A | 7/1994 | Bonutti |
| 5,334,146 A | 8/1994 | Ozasa |
| 5,336,231 A | 8/1994 | Adair |
| 5,336,240 A | 8/1994 | Metzler et al. |
| 5,339,799 A | 8/1994 | Kami et al. |
| 5,345,927 A | 9/1994 | Bonutti |
| 5,349,956 A | 9/1994 | Bonutti |
| 5,352,229 A | 10/1994 | Goble et al. |
| 5,354,298 A | 10/1994 | Lee et al. |
| 5,354,302 A | 10/1994 | Ko |
| 5,356,413 A | 10/1994 | Martins et al. |
| 5,360,450 A | 11/1994 | Giannini |
| 5,366,480 A | 11/1994 | Corriveaau et al. |
| 5,370,646 A | 12/1994 | Reese et al. |
| 5,370,660 A | 12/1994 | Weinstein et al. |
| 5,370,662 A | 12/1994 | Stone et al. |
| 5,372,146 A | 12/1994 | Branch |
| 5,374,235 A | 12/1994 | Ahrens |
| 5,376,101 A | 12/1994 | Green et al. |
| 5,376,126 A | 12/1994 | Lin |
| 5,379,759 A | 1/1995 | Sewell, Jr. |
| 5,382,254 A | 1/1995 | McGarry et al. |
| 5,383,883 A | 1/1995 | Wilk et al. |
| 5,383,905 A | 1/1995 | Golds et al. |
| 5,383,937 A | 1/1995 | Mikhail |
| RE34,866 E | 2/1995 | Kensey et al. |
| 5,390,683 A | 2/1995 | Pisharodi |
| 5,391,171 A | 2/1995 | Schmieding |
| 5,391,173 A | 2/1995 | Wilk |
| RE34,871 E | 3/1995 | McGuire et al. |
| 5,395,308 A | 3/1995 | Fox et al. |
| 5,395,376 A | 3/1995 | Caspari et al. |
| 5,397,311 A | 3/1995 | Walker et al. |
| 5,397,331 A | 3/1995 | Himpens et al. |
| 5,400,805 A | 3/1995 | Warren |
| 5,403,312 A | 4/1995 | Yates et al. |
| 5,403,317 A | 4/1995 | Bonutti |
| 5,403,348 A * | 4/1995 | Bonutti .................. 606/232 |
| 5,405,359 A | 4/1995 | Pierce |
| 5,411,523 A | 5/1995 | Goble |
| 5,413,585 A | 5/1995 | Pagedas |
| 5,415,663 A | 5/1995 | Luckman et al. |
| 5,417,691 A | 5/1995 | Hayhurst |
| 5,417,700 A | 5/1995 | Egan |
| 5,417,701 A | 5/1995 | Holmes |
| 5,417,712 A | 5/1995 | Whittaker et al. |
| 5,423,796 A | 6/1995 | Shikhman et al. |
| 5,423,819 A | 6/1995 | Small et al. |
| 5,423,860 A | 6/1995 | Lizardi et al. |
| 5,425,733 A | 6/1995 | Schmieding |
| 5,431,670 A | 7/1995 | Holmes |
| 5,439,470 A | 8/1995 | Li |
| 5,441,502 A | 8/1995 | Bartlett |
| 5,441,538 A | 8/1995 | Bonutti |
| 5,443,482 A | 8/1995 | Stone et al. |
| 5,443,512 A | 8/1995 | Parr et al. |
| 5,445,615 A | 8/1995 | Yoon |
| 5,447,503 A | 9/1995 | Miller |
| 5,449,372 A | 9/1995 | Schmaltz et al. |
| 5,449,382 A | 9/1995 | Dayton |
| 5,451,235 A | 9/1995 | Lock |
| 5,453,090 A | 9/1995 | Martinez et al. |
| 5,454,365 A | 10/1995 | Bonutti |
| 5,456,722 A | 10/1995 | McLeod et al. |
| 5,458,653 A | 10/1995 | Davidson |
| 5,462,549 A | 10/1995 | Glock |
| 5,462,561 A | 10/1995 | Voda |
| 5,464,424 A | 11/1995 | O'Don |
| 5,464,425 A | 11/1995 | Skiba |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,474,559 A | 12/1995 | Bertin et al. |
| 5,478,351 A | 12/1995 | Meade et al. |
| 5,478,353 A | 12/1995 | Yoon |
| 5,480,403 A | 1/1996 | Lee et al. |
| 5,484,437 A | 1/1996 | Michelson |
| 5,486,197 A | 1/1996 | Le et al. |
| 5,487,844 A | 1/1996 | Fujita |
| 5,488,958 A | 2/1996 | Topel et al. |

(56) References Cited

U.S. PATENT DOCUMENTS

| | | |
|---|---|---|
| 5,492,697 A | 2/1996 | Boyan et al. |
| 5,496,292 A | 3/1996 | Burnham |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner |
| 5,505,735 A | 4/1996 | Li |
| 5,507,754 A | 4/1996 | Green et al. |
| 5,514,091 A | 5/1996 | Yoon |
| 5,514,153 A | 5/1996 | Bonutti |
| 5,520,700 A | 5/1996 | Beyar et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,542,947 A | 8/1996 | Treacy |
| 5,545,178 A | 8/1996 | Kensey et al. |
| 5,545,180 A | 8/1996 | Le et al. |
| 5,545,206 A | 8/1996 | Carson |
| 5,545,222 A | 8/1996 | Bonutti |
| 5,549,630 A | 8/1996 | Bonutti |
| 5,549,631 A | 8/1996 | Bonutti |
| 5,549,689 A | 8/1996 | Epstein et al. |
| 5,550,172 A | 8/1996 | Regula et al. |
| 2,215,943 A | 9/1996 | Collette |
| 5,556,402 A | 9/1996 | Xu |
| 5,562,668 A | 10/1996 | Johnson |
| 5,562,684 A | 10/1996 | Kammerer |
| 5,562,688 A | 10/1996 | Riza |
| 5,569,252 A | 10/1996 | Justin et al. |
| 5,569,259 A | 10/1996 | Ferrante et al. |
| 5,569,305 A | 10/1996 | Bonutti |
| 5,569,306 A | 10/1996 | Thal |
| 5,571,139 A | 11/1996 | Jenkins, Jr. |
| 5,571,196 A | 11/1996 | Stein |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer |
| 5,577,517 A | 11/1996 | Bonutti |
| 5,580,344 A | 12/1996 | Hasson |
| 5,584,835 A | 12/1996 | Greenfield |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van de Moer et al. |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,565 A | 2/1997 | Huebner |
| 5,601,595 A | 2/1997 | Smith |
| 5,607,427 A | 3/1997 | Tschakaloff |
| 5,609,595 A | 3/1997 | Pennig |
| 5,609,635 A | 3/1997 | Michelson |
| 5,618,314 A | 4/1997 | Harwin et al. |
| 5,620,448 A | 4/1997 | Puddu |
| 5,620,461 A | 4/1997 | Muijs Van De Moer et al. |
| 5,624,462 A | 4/1997 | Bonutti |
| 5,624,463 A | 4/1997 | Stone et al. |
| 5,626,612 A | 5/1997 | Bartlett |
| 5,626,614 A | 5/1997 | Hart |
| 5,626,718 A | 5/1997 | Philippe et al. |
| 5,628,751 A | 5/1997 | Sander et al. |
| 5,630,824 A | 5/1997 | Hart |
| 5,634,926 A | 6/1997 | Jobe |
| 5,643,274 A | 7/1997 | Sander et al. |
| 5,643,293 A | 7/1997 | Kogasaka et al. |
| 5,643,295 A | 7/1997 | Yoon |
| 5,643,320 A | 7/1997 | Lower et al. |
| 5,643,321 A | 7/1997 | McDevitt |
| 5,644,002 A | 7/1997 | Cooper et al. |
| 5,645,553 A | 7/1997 | Kolesa et al. |
| 5,645,588 A | 7/1997 | Graf et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,662,710 A | 9/1997 | Bonutti |
| 5,665,089 A | 9/1997 | Dall et al. |
| 5,665,109 A | 9/1997 | Yoon |
| 5,665,112 A | 9/1997 | Thal |
| 5,667,513 A | 9/1997 | Torrie et al. |
| 5,667,520 A | 9/1997 | Bonutti |
| 5,669,909 A | 9/1997 | Zdeblick et al. |
| 5,669,917 A | 9/1997 | Sauer et al. |
| 5,674,240 A | 10/1997 | Bonutti |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,682,886 A | 11/1997 | Delp et al. |
| 5,683,401 A | 11/1997 | Schmieding et al. |
| 5,683,418 A | 11/1997 | Luscombe et al. |
| 5,683,469 A | 11/1997 | Johnson et al. |
| 5,685,820 A | 11/1997 | Riek et al. |
| 5,685,826 A | 11/1997 | Bonutti |
| 5,688,283 A | 11/1997 | Knapp |
| 5,690,654 A | 11/1997 | Ovil |
| 5,690,655 A | 11/1997 | Hart et al. |
| 5,690,674 A | 11/1997 | Diaz |
| 5,690,676 A | 11/1997 | DiPoto et al. |
| 5,693,055 A | 12/1997 | Zahiri et al. |
| 5,694,951 A | 12/1997 | Bonutti |
| 5,697,950 A | 12/1997 | Fucci et al. |
| 5,702,397 A | 12/1997 | Gonle et al. |
| 5,702,462 A | 12/1997 | Oberlander |
| 5,707,390 A | 1/1998 | Bonutti |
| 5,707,395 A | 1/1998 | Li |
| 5,713,897 A | 2/1998 | Goble et al. |
| 5,713,903 A | 2/1998 | Sander et al. |
| 5,713,921 A | 2/1998 | Bonutti |
| 5,715,836 A | 2/1998 | Kliegis et al. |
| 5,716,325 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,722,978 A | 3/1998 | Jenkins, Jr. |
| 5,723,016 A | 3/1998 | Minns et al. |
| 5,725,529 A | 3/1998 | Nicholson et al. |
| 5,725,541 A * | 3/1998 | Anspach et al. ............... 606/151 |
| 5,725,556 A | 3/1998 | Moser et al. |
| 5,725,557 A | 3/1998 | Gatturna et al. |
| 5,725,582 A | 3/1998 | Bevan |
| 5,730,747 A | 3/1998 | Ek et al. |
| 5,733,306 A | 3/1998 | Bonutti |
| 5,735,875 A | 4/1998 | Bonutti et al. |
| 5,735,877 A | 4/1998 | Pagedas |
| 5,735,899 A | 4/1998 | Schwartz et al. |
| 5,741,268 A | 4/1998 | Schutz |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,763,416 A | 6/1998 | Bonadio et al. |
| 5,766,221 A | 6/1998 | Benderev et al. |
| 5,766,251 A | 6/1998 | Koshino |
| 5,769,854 A | 6/1998 | Bastian et al. |
| 5,769,894 A | 6/1998 | Ferragamo |
| 5,772,672 A | 6/1998 | Toy et al. |

(56) References Cited

U.S. PATENT DOCUMENTS

| | | |
|---|---|---|
| 5,776,151 A | 7/1998 | Chan |
| 5,779,706 A | 7/1998 | Tschakaloff |
| 5,779,719 A | 7/1998 | Klein et al. |
| 5,779,728 A | 7/1998 | Lunsford et al. |
| 5,782,862 A | 7/1998 | Bonutti |
| 5,782,925 A | 7/1998 | Collazo et al. |
| 5,785,713 A | 7/1998 | Jobe |
| 5,792,096 A | 8/1998 | Rentmeester et al. |
| 5,797,931 A | 8/1998 | Bito et al. |
| 5,797,963 A | 8/1998 | McDevitt |
| 5,800,537 A | 9/1998 | Bell |
| 5,800,544 A | 9/1998 | Demopulos |
| 5,806,518 A | 9/1998 | Mittelstadt |
| 5,807,403 A | 9/1998 | Beyar et al. |
| 5,810,827 A | 9/1998 | Haines et al. |
| 5,810,849 A | 9/1998 | Kontos |
| 5,810,853 A | 9/1998 | Yoon |
| 5,810,884 A | 9/1998 | Kim |
| 5,814,071 A | 9/1998 | McDevitt et al. |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,827,318 A | 10/1998 | Bonutti |
| 5,830,125 A | 11/1998 | Scribner et al. |
| 5,836,897 A | 11/1998 | Sakurai et al. |
| 5,836,948 A | 11/1998 | Zucherman et al. |
| 5,839,899 A | 11/1998 | Robinson |
| 5,843,178 A | 12/1998 | Vanney et al. |
| 5,845,645 A | 12/1998 | Bonutti |
| 5,851,185 A | 12/1998 | Berns |
| 5,853,422 A | 12/1998 | Huebsch et al. |
| 5,860,997 A | 1/1999 | Bonutti |
| 5,865,834 A | 2/1999 | McGuire |
| 5,866,634 A | 2/1999 | Tokushige |
| 5,868,749 A | 2/1999 | Reed |
| 5,871,018 A | 2/1999 | Delp et al. |
| 5,873,891 A | 2/1999 | Sohn |
| 5,874,235 A | 2/1999 | Chan |
| 5,879,372 A | 3/1999 | Bartlett |
| 5,888,196 A | 3/1999 | Bonutti |
| 5,888,219 A | 3/1999 | Bonutti |
| 5,891,166 A | 4/1999 | Schervinsky |
| 5,891,168 A | 4/1999 | Thal |
| 5,893,880 A | 4/1999 | Egan et al. |
| 5,895,426 A | 4/1999 | Scarborough et al. |
| 5,897,559 A | 4/1999 | Masini |
| 5,897,574 A | 4/1999 | Bonutti |
| 5,899,911 A | 5/1999 | Carter |
| 5,899,921 A | 5/1999 | Caspari et al. |
| 5,902,321 A | 5/1999 | Caspari et al. |
| 5,906,579 A | 5/1999 | Vander Salm et al. |
| 5,906,616 A | 5/1999 | Pavlov et al. |
| 5,906,625 A | 5/1999 | Bito et al. |
| 5,908,429 A | 6/1999 | Yoon |
| 5,911,721 A | 6/1999 | Nicholson et al. |
| 5,916,221 A | 6/1999 | Hodorek et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A | 7/1999 | Meyers |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,935,094 A | 8/1999 | Zupkas |
| 5,935,131 A | 8/1999 | Bonutti |
| 5,935,149 A | 8/1999 | Ek |
| 5,940,942 A | 8/1999 | Fong |
| 5,941,900 A | 8/1999 | Bonutti |
| 5,941,901 A | 8/1999 | Egan |
| 5,947,982 A | 9/1999 | Duran |
| 5,948,000 A | 9/1999 | Larsen et al. |
| 5,948,001 A | 9/1999 | Larsen |
| 5,948,002 A | 9/1999 | Bonutti |
| 5,951,590 A | 9/1999 | Goldfarb |
| 5,954,739 A | 9/1999 | Bonutti |
| 5,957,953 A | 9/1999 | DiPoto et al. |
| 5,961,499 A | 10/1999 | Bonutti |
| 5,961,521 A | 10/1999 | Roger |
| 5,961,538 A | 10/1999 | Pedlick et al. |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,044 A | 10/1999 | Nicholson et al. |
| 5,968,046 A | 10/1999 | Castleman |
| 5,968,047 A | 10/1999 | Reed |
| 5,980,520 A | 11/1999 | Vancaillie |
| 5,980,558 A | 11/1999 | Wiley |
| 5,980,559 A | 11/1999 | Bonutti |
| 5,984,929 A | 11/1999 | Bashiri et al. |
| 5,984,967 A | 11/1999 | Zdeblick et al. |
| 5,989,282 A | 11/1999 | Bonutti |
| 5,989,289 A | 11/1999 | Coates et al. |
| 5,993,458 A | 11/1999 | Vaitekunas et al. |
| 5,993,477 A | 11/1999 | Vaitekunas et al. |
| 6,007,537 A | 12/1999 | Burkinshaw et al. |
| 6,007,567 A | 12/1999 | Bonutti |
| 6,007,580 A | 12/1999 | Lehto et al. |
| 6,008,433 A | 12/1999 | Stone |
| 6,010,525 A | 1/2000 | Bonutti et al. |
| 6,010,526 A | 1/2000 | Sandstrom et al. |
| 6,013,853 A | 1/2000 | Athanasiou et al. |
| 6,017,305 A | 1/2000 | Bonutti |
| 6,017,321 A | 1/2000 | Boone |
| 6,024,746 A | 2/2000 | Katz |
| 6,033,410 A | 3/2000 | McLean et al. |
| 6,033,429 A | 3/2000 | Magovern |
| 6,033,430 A | 3/2000 | Bonutti |
| 6,042,596 A | 3/2000 | Bonutti |
| 6,045,551 A | 4/2000 | Bonutti |
| 6,050,998 A | 4/2000 | Fletcher et al. |
| 6,056,751 A | 5/2000 | Fenton, Jr. |
| 6,056,754 A | 5/2000 | Haines et al. |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton |
| 6,059,831 A | 5/2000 | Braslow et al. |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,066,175 A | 5/2000 | Henderson et al. |
| 6,068,637 A | 5/2000 | Popov et al. |
| 6,068,648 A | 5/2000 | Cole et al. |
| 6,074,409 A | 6/2000 | Goldfarb |
| 6,077,277 A | 6/2000 | Mollenauer et al. |
| 6,077,292 A | 6/2000 | Bonutti |
| 6,080,161 A | 6/2000 | Eaves, III et al. |
| 6,083,244 A | 7/2000 | Lubbers et al. |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,547 A | 8/2000 | Gellman et al. |
| 6,099,550 A | 8/2000 | Yoon |
| 6,099,552 A | 8/2000 | Adams |
| 6,102,850 A | 8/2000 | Wang et al. |
| 6,102,928 A | 8/2000 | Bonutti |
| 6,102,950 A | 8/2000 | Vaccaro |
| 6,102,955 A | 8/2000 | Mendes et al. |
| 6,106,529 A | 8/2000 | Techiera |
| 6,106,545 A | 8/2000 | Egan |
| 6,110,188 A | 8/2000 | Narciso, Jr. |
| 6,110,207 A | 8/2000 | Eichhorn et al. |
| 6,117,160 A | 9/2000 | Bonutti |

(56) References Cited

U.S. PATENT DOCUMENTS

| | | |
|---|---|---|
| 6,120,536 A | 9/2000 | Ding et al. |
| 6,123,710 A | 9/2000 | Pinczewski et al. |
| 6,125,574 A | 10/2000 | Ganaja et al. |
| 6,126,677 A | 10/2000 | Ganaja et al. |
| 6,132,468 A | 10/2000 | Mansmann |
| 6,132,472 A | 10/2000 | Bonutti |
| 6,139,320 A | 10/2000 | Hahn |
| RE36,974 E | 11/2000 | Bonutti |
| 6,146,385 A | 11/2000 | Torrie et al. |
| 6,149,669 A | 11/2000 | Li |
| 6,152,949 A | 11/2000 | Bonutti |
| 6,155,756 A | 12/2000 | Mericle et al. |
| 6,156,070 A | 12/2000 | Incavo et al. |
| 6,159,224 A | 12/2000 | Yoon |
| 6,159,234 A | 12/2000 | Bonutti et al. |
| 6,171,236 B1 | 1/2001 | Bonutti |
| 6,171,299 B1 | 1/2001 | Bonutti |
| 6,171,307 B1 | 1/2001 | Orlich |
| 6,171,340 B1 | 1/2001 | McDowell |
| 6,174,313 B1 | 1/2001 | Bonutti |
| 6,174,314 B1 | 1/2001 | Waddell |
| 6,174,324 B1 | 1/2001 | Egan et al. |
| 6,179,840 B1 | 1/2001 | Bowman |
| 6,179,850 B1 | 1/2001 | Goradia |
| 6,187,008 B1 | 2/2001 | Hamman |
| 6,187,023 B1 | 2/2001 | Bonutti |
| 6,190,400 B1 | 2/2001 | Van De Moer et al. |
| 6,190,401 B1 | 2/2001 | Green |
| 6,193,754 B1 | 2/2001 | Seedhom |
| 6,200,322 B1 | 3/2001 | Branch et al. |
| 6,200,329 B1 | 3/2001 | Fung et al. |
| 6,203,565 B1 | 3/2001 | Bonutti et al. |
| 6,214,051 B1 | 4/2001 | Badorf et al. |
| 6,217,591 B1 | 4/2001 | Egan et al. |
| 6,217,617 B1 | 4/2001 | Bonutti |
| 6,224,593 B1 | 5/2001 | Ryan |
| 6,224,630 B1 | 5/2001 | Bao et al. |
| 6,228,086 B1 | 5/2001 | Wahl et al. |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,749 B1 | 6/2001 | Rayhanabad |
| 6,241,771 B1 | 6/2001 | Gresser et al. |
| 6,258,091 B1 | 7/2001 | Sevrain et al. |
| 6,261,295 B1 | 7/2001 | Nicholson |
| 6,264,675 B1 | 7/2001 | Brotz |
| 6,267,761 B1 | 7/2001 | Ryan |
| 6,273,717 B1 | 8/2001 | Hahn et al. |
| 6,277,136 B1 | 8/2001 | Bonutti |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,296,646 B1 | 10/2001 | Williamson |
| 6,306,159 B1 | 10/2001 | Schwartz et al. |
| 6,309,405 B1 | 10/2001 | Bonutti |
| 6,312,448 B1 | 11/2001 | Bonutti |
| 6,319,252 B1 | 11/2001 | McDevitt et al. |
| 6,319,271 B1 | 11/2001 | Schwartz et al. |
| 6,325,806 B1 | 12/2001 | Fox |
| 6,338,730 B1 | 1/2002 | Bonutti et al. |
| 6,340,365 B2 | 1/2002 | Dittrich et al. |
| 6,342,075 B1 | 1/2002 | Macarthur |
| 6,348,056 B1 | 2/2002 | Bates et al. |
| 6,358,252 B1 | 3/2002 | Shapira |
| 6,358,266 B1 | 3/2002 | Bonutti |
| 6,358,271 B1 | 3/2002 | Egan et al. |
| 6,361,565 B1 | 3/2002 | Bonutti |
| 6,364,897 B1 | 4/2002 | Bonutti |
| 6,368,325 B1 | 4/2002 | McKinley et al. |
| 6,368,326 B1 | 4/2002 | Dakin et al. |
| 6,368,343 B1 | 4/2002 | Bonutti et al. |
| 6,371,957 B1 | 4/2002 | Amrein et al. |
| 6,398,797 B2 | 6/2002 | Bombard et al. |
| 6,409,742 B1 | 6/2002 | Fulton, III |
| 6,409,743 B1 | 6/2002 | Fenton, Jr. |
| 6,409,764 B1 | 6/2002 | White et al. |
| 6,419,704 B1 | 7/2002 | Ferree |
| 6,423,063 B1 | 7/2002 | Bonutti |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |
| 6,451,042 B1 | 9/2002 | Bonutti |
| 6,461,360 B1 | 10/2002 | Adams |
| 6,464,713 B2 | 10/2002 | Bonutti |
| 6,468,289 B1 | 10/2002 | Bonutti |
| 6,468,293 B2 | 10/2002 | Bonutti et al. |
| 6,471,715 B1 | 10/2002 | Weiss |
| 6,471,724 B2 | 10/2002 | Zdeblick et al. |
| 6,475,230 B1 | 11/2002 | Bonutti |
| 6,482,209 B1 | 11/2002 | Engh et al. |
| 6,488,196 B1 | 12/2002 | Fenton |
| 6,500,179 B1 | 12/2002 | Masini |
| 6,500,195 B2 | 12/2002 | Bonutti |
| 6,503,259 B2 | 1/2003 | Huxel et al. |
| 6,503,267 B2 | 1/2003 | Bonutti et al. |
| 6,503,277 B2 | 1/2003 | Bonutti |
| 6,527,774 B2 | 3/2003 | Lieberman |
| 6,530,933 B1 | 3/2003 | Yeung et al. |
| 6,535,764 B2 | 3/2003 | Imran et al. |
| 6,540,786 B2 | 4/2003 | Chibrac et al. |
| 6,543,455 B2 | 4/2003 | Bonutti |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,554,852 B1 | 4/2003 | Oberlander |
| 6,557,426 B2 | 5/2003 | Reinemann, Jr. |
| 6,558,390 B2 | 5/2003 | Cragg |
| 6,562,043 B1 | 5/2003 | Chan |
| 6,568,313 B2 | 5/2003 | Fukui et al. |
| 6,569,167 B1 | 5/2003 | Bobechko et al. |
| 6,569,187 B1 | 5/2003 | Bonutti |
| 6,572,635 B1 | 6/2003 | Bonutti |
| 6,575,980 B1 | 6/2003 | Robie et al. |
| 6,575,982 B1 | 6/2003 | Bonutti |
| D477,776 S | 7/2003 | Pontaoe |
| 6,585,750 B2 | 7/2003 | Bonutti |
| 6,585,764 B2 | 7/2003 | Wright et al. |
| 6,589,248 B1 | 7/2003 | Hughes |
| 6,589,281 B2 | 7/2003 | Hyde, Jr. |
| 6,592,531 B2 | 7/2003 | Bonutti |
| 6,592,609 B1 | 7/2003 | Bonutti |
| 6,594,517 B1 | 7/2003 | Nevo |
| 6,605,090 B1 | 8/2003 | Trieu et al. |
| 6,607,534 B2 | 8/2003 | Bonutti |
| 6,610,080 B2 | 8/2003 | Morgan |
| 6,616,696 B1 | 9/2003 | Merchant |
| 6,618,910 B1 | 9/2003 | Pontaoe |
| 6,620,181 B1 | 9/2003 | Bonutti |
| 6,623,486 B1 | 9/2003 | Weaver |
| 6,623,487 B1 | 9/2003 | Goshert |
| 6,626,944 B1 | 9/2003 | Taylor |
| 6,630,000 B1 | 10/2003 | Bonutti |
| 6,632,245 B2 | 10/2003 | Kim |
| 6,635,073 B2 | 10/2003 | Bonutti |
| 6,638,279 B2 | 10/2003 | Bonutti |
| 6,638,309 B2 | 10/2003 | Bonutti |
| 6,641,592 B1 | 11/2003 | Sauer et al. |
| 6,645,227 B2 | 11/2003 | Fallin et al. |
| 6,652,532 B2 | 11/2003 | Bonutti |
| 6,652,587 B2 | 11/2003 | Felt et al. |
| 6,666,877 B2 | 12/2003 | Morgan et al. |
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 | 3/2004 | Franischelli |
| 6,702,821 B2 | 3/2004 | Bonutti |
| 6,702,856 B2 | 3/2004 | Bonutti |
| 6,705,179 B1 | 3/2004 | Mohtasham |
| 6,709,457 B1 | 3/2004 | Otte |

(56) References Cited

U.S. PATENT DOCUMENTS

| | | |
|---|---|---|
| 6,719,765 B2 | 4/2004 | Bonutti |
| 6,719,797 B1 | 4/2004 | Ferree |
| 6,719,803 B2 | 4/2004 | Bonutti |
| 6,722,552 B2 | 4/2004 | Fenton |
| 6,723,102 B2 | 4/2004 | Johnson et al. |
| 6,733,506 B1 | 5/2004 | McDevitt et al. |
| 6,733,531 B1 | 5/2004 | Trieu |
| 6,736,853 B2 | 5/2004 | Bonutti |
| 6,755,865 B2 | 6/2004 | Tarabishy |
| 6,764,514 B1 | 7/2004 | Li et al. |
| 6,770,078 B2 | 8/2004 | Bonutti |
| 6,776,938 B2 | 8/2004 | Bonutti |
| 6,780,198 B1 | 8/2004 | Gregoire et al. |
| 6,786,989 B2 | 9/2004 | Torriani et al. |
| 6,796,003 B1 | 9/2004 | Marvel |
| 6,818,010 B2 | 11/2004 | Eichhorn et al. |
| 6,823,871 B2 | 11/2004 | Schmieding |
| 6,827,723 B2 | 12/2004 | Carson |
| 6,835,198 B2 | 12/2004 | Bonutti |
| 6,860,885 B2 | 3/2005 | Bonutti |
| 6,860,904 B2 | 3/2005 | Bonutti |
| 6,878,167 B2 | 4/2005 | Ferree |
| 6,890,334 B2 | 5/2005 | Brace et al. |
| 6,893,434 B2 | 5/2005 | Fenton et al. |
| 6,899,722 B2 | 5/2005 | Bonutti |
| 6,905,517 B2 | 6/2005 | Bonutti |
| 6,908,466 B1 | 6/2005 | Bonutti et al. |
| 6,913,666 B1 | 7/2005 | Aeschlimann et al. |
| 6,916,321 B2 | 7/2005 | TenHuisen |
| 6,921,264 B2 | 7/2005 | Mayer et al. |
| 6,923,824 B2 | 8/2005 | Morgan et al. |
| 6,932,835 B2 | 8/2005 | Bonutti |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt et al. |
| 6,989,029 B2 | 1/2006 | Bonutti |
| 6,990,982 B1 | 1/2006 | Bonutti |
| 6,997,940 B2 | 2/2006 | Bonutti |
| 7,001,385 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,018,380 B2 | 3/2006 | Cole |
| 7,033,379 B2 | 4/2006 | Peterson |
| 7,048,741 B2 | 5/2006 | Swanson |
| 7,048,755 B2 | 5/2006 | Bonutti |
| 7,066,960 B1 | 6/2006 | Dickman |
| 7,070,557 B2 | 7/2006 | Bonutti |
| 7,087,073 B2 | 8/2006 | Bonutti |
| 7,090,111 B2 | 8/2006 | Egan et al. |
| 7,094,251 B2 | 8/2006 | Bonutti |
| 7,104,996 B2 | 9/2006 | Bonutti |
| 7,114,500 B2 | 10/2006 | Bonutti |
| 7,128,753 B1 | 10/2006 | Bonutti et al. |
| 7,128,763 B1 | 10/2006 | Blatt |
| 7,134,437 B2 | 11/2006 | Bonutti |
| 7,147,652 B2 | 12/2006 | Bonutti et al. |
| 7,153,312 B1 | 12/2006 | Torrie et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,208,013 B1 | 4/2007 | Bonutti |
| 7,217,273 B2 | 5/2007 | Bonutti |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,311,719 B2 | 12/2007 | Bonutti |
| 7,329,263 B2 | 2/2008 | Bonutti |
| 7,335,205 B2 | 2/2008 | Aeschlimann |
| 7,371,240 B2 | 5/2008 | Pinczewski et al. |
| 7,429,266 B2 | 9/2008 | Bonutti |
| 7,445,634 B2 | 11/2008 | Trieu |
| 7,462,200 B2 | 12/2008 | Bonutti |
| 7,481,825 B2 | 1/2009 | Bonutti |
| 7,481,831 B2 | 1/2009 | Bonutti |
| 7,510,557 B1 | 3/2009 | Bonutti |
| 7,510,895 B2 | 3/2009 | Rateman |
| 7,610,557 B2 | 10/2009 | McLennan et al. |
| 7,615,054 B1 | 11/2009 | Bonutti |
| 7,635,390 B1 | 12/2009 | Bonutti |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,837,736 B2 | 11/2010 | Bonutti |
| 7,854,750 B2 | 12/2010 | Bonutti |
| 7,879,072 B2 | 2/2011 | Bonutti |
| 7,891,691 B2 | 2/2011 | Bearey |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,959,635 B1 | 6/2011 | Bonutti |
| 7,967,820 B2 | 6/2011 | Bonutti |
| RE43,143 E | 1/2012 | Hayhurst |
| 8,092,462 B2 | 1/2012 | Pinczewski et al. |
| 8,128,669 B2 | 3/2012 | Bonutti |
| 8,133,229 B1 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 8,425,522 B2 | 4/2013 | Bonutti |
| 8,486,066 B2 | 7/2013 | Bonutti |
| 8,496,657 B2 | 7/2013 | Bonutti et al. |
| 8,617,185 B2 | 12/2013 | Bonutti |
| 8,623,030 B2 | 1/2014 | Bonutti |
| 8,632,552 B2 | 1/2014 | Bonutti |
| 8,641,726 B2 | 2/2014 | Bonutti |
| 8,690,944 B2 | 4/2014 | Bonutti |
| 2001/0002440 A1 | 5/2001 | Bonutti |
| 2001/0009250 A1 | 7/2001 | Herman et al. |
| 2001/0023371 A1 | 9/2001 | Bonutti |
| 2001/0041916 A1 | 11/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora |
| 2002/0026244 A1 | 2/2002 | Trieu |
| 2002/0029055 A1 | 3/2002 | Bonutti |
| 2002/0029083 A1 | 3/2002 | Zucherman et al. |
| 2002/0029084 A1 | 3/2002 | Paul et al. |
| 2002/0040246 A1 | 4/2002 | Bonutti |
| 2002/0045902 A1 | 4/2002 | Bonutti |
| 2002/0062153 A1 | 5/2002 | Paul et al. |
| 2002/0095160 A1 | 7/2002 | Bonutti |
| 2002/0103495 A1 | 8/2002 | Cole |
| 2002/0123750 A1 | 9/2002 | Eisermann et al. |
| 2002/0138150 A1 | 9/2002 | Leclercq |
| 2002/0183762 A1 | 12/2002 | Anderson et al. |
| 2002/0188301 A1 | 12/2002 | Dallara et al. |
| 2003/0009147 A1 | 1/2003 | Bonutti |
| 2003/0023260 A1 | 1/2003 | Bonutti |
| 2003/0032975 A1 | 2/2003 | Bonutti |
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0105474 A1 | 6/2003 | Bonutti |
| 2003/0118518 A1 | 6/2003 | Hahn et al. |
| 2003/0158582 A1 | 8/2003 | Bonutti et al. |
| 2003/0167072 A1 | 9/2003 | Oberlander |
| 2003/0181800 A1 | 9/2003 | Bonutti |
| 2003/0195530 A1 | 10/2003 | Thill |
| 2003/0195565 A1 | 10/2003 | Bonutti |
| 2003/0204204 A1 | 10/2003 | Bonutti |
| 2003/0216742 A1 | 11/2003 | Wetzler et al. |

(56) References Cited

U.S. PATENT DOCUMENTS

| | | |
|---|---|---|
| 2003/0225438 A1 | 12/2003 | Bonutti et al. |
| 2003/0229361 A1 | 12/2003 | Jackson |
| 2004/0010287 A1 | 1/2004 | Bonutti |
| 2004/0030341 A1 | 2/2004 | Aeschlimann et al. |
| 2004/0034357 A1 | 2/2004 | Beane et al. |
| 2004/0097794 A1 | 5/2004 | Bonutti |
| 2004/0097939 A1 | 5/2004 | Bonutti |
| 2004/0098016 A1 | 5/2004 | Bonutti |
| 2004/0098050 A1 | 5/2004 | Foerster et al. |
| 2004/0127930 A1 | 7/2004 | Bonutti |
| 2004/0138689 A1 | 7/2004 | Bonutti |
| 2004/0138690 A1 | 7/2004 | Bonutti |
| 2004/0138703 A1 | 7/2004 | Alleyne |
| 2004/0143285 A1 | 7/2004 | Bonutti |
| 2004/0143334 A1 | 7/2004 | Ferree |
| 2004/0167548 A1 | 8/2004 | Bonutti |
| 2004/0172033 A1 | 9/2004 | Bonutti |
| 2004/0193181 A1 | 9/2004 | Bonutti |
| 2004/0220616 A1 | 11/2004 | Bonutti |
| 2004/0225325 A1 | 11/2004 | Bonutti |
| 2004/0230223 A1 | 11/2004 | Bonutti |
| 2004/0236374 A1 | 11/2004 | Bonutti et al. |
| 2004/0254582 A1 | 12/2004 | Bonutti |
| 2005/0033366 A1 | 2/2005 | Cole |
| 2005/0038514 A1 | 2/2005 | Helm et al. |
| 2005/0043796 A1 | 2/2005 | Grant et al. |
| 2005/0071012 A1 | 3/2005 | Serhan et al. |
| 2005/0090827 A1 | 4/2005 | Gedebou |
| 2005/0096699 A1 | 5/2005 | Wixey et al. |
| 2005/0110214 A1 | 5/2005 | Shank et al. |
| 2005/0113928 A1 | 5/2005 | Cragg et al. |
| 2005/0126680 A1 | 6/2005 | Aeschlimann et al. |
| 2005/0143826 A1 | 6/2005 | Zucherman et al. |
| 2005/0149024 A1 | 7/2005 | Ferrante et al. |
| 2005/0149029 A1 | 7/2005 | Bonutti |
| 2005/0203521 A1 | 9/2005 | Bonutti |
| 2005/0216059 A1 | 9/2005 | Bonutti |
| 2005/0216087 A1 | 9/2005 | Zucherman et al. |
| 2005/0222620 A1 | 10/2005 | Bonutti |
| 2005/0240190 A1 | 10/2005 | Gall et al. |
| 2005/0240227 A1 | 10/2005 | Bonutti |
| 2005/0246021 A1 | 11/2005 | Ringeisen et al. |
| 2005/0261684 A1 | 11/2005 | Shaolian et al. |
| 2005/0267481 A1 | 12/2005 | Carl et al. |
| 2005/0267534 A1 | 12/2005 | Bonutti |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0064095 A1 | 3/2006 | Senn et al. |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0142799 A1 | 6/2006 | Bonutti |
| 2006/0167495 A1 | 7/2006 | Bonutti |
| 2006/0200199 A1 | 9/2006 | Bonutti |
| 2006/0212073 A1 | 9/2006 | Bonutti |
| 2006/0217765 A1 | 9/2006 | Bonutti |
| 2006/0229623 A1 | 10/2006 | Bonutti et al. |
| 2006/0235470 A1 | 10/2006 | Bonutti |
| 2006/0241695 A1 | 10/2006 | Bonutti |
| 2006/0265009 A1 | 11/2006 | Bonutti |
| 2006/0265011 A1 | 11/2006 | Bonutti |
| 2007/0032825 A1 | 2/2007 | Bonutti et al. |
| 2007/0088362 A1 | 4/2007 | Bonutti et al. |
| 2007/0102005 A1 | 5/2007 | Bonutti |
| 2007/0118129 A1 | 5/2007 | Fraser et al. |
| 2007/0198555 A1 | 8/2007 | Friedman et al. |
| 2007/0208378 A1 | 9/2007 | Bonutti et al. |
| 2007/0265561 A1 | 11/2007 | Yeung |
| 2007/0270833 A1 | 11/2007 | Bonutti |
| 2008/0021474 A1 | 1/2008 | Bonutti et al. |
| 2008/0039845 A1 | 2/2008 | Bonutti |
| 2008/0039873 A1 | 2/2008 | Bonutti |
| 2008/0046090 A1 | 2/2008 | Paul et al. |
| 2008/0047567 A1 | 2/2008 | Bonutti |
| 2008/0051799 A1 | 2/2008 | Bonutti |
| 2008/0058822 A1 | 3/2008 | Bonutti |
| 2008/0065140 A1 | 3/2008 | Bonutti |
| 2008/0097448 A1 | 4/2008 | Binder et al. |
| 2008/0103519 A1 | 5/2008 | Bonutti |
| 2008/0108897 A1 | 5/2008 | Bonutti et al. |
| 2008/0108916 A1 | 5/2008 | Bonutti |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti |
| 2008/0195145 A1 | 8/2008 | Bonutti et al. |
| 2008/0269753 A1 | 10/2008 | Cannestra |
| 2008/0269808 A1 | 10/2008 | Gall et al. |
| 2009/0024161 A1 | 1/2009 | Bonutti |
| 2009/0093684 A1 | 4/2009 | Schorer |
| 2009/0138014 A1 | 5/2009 | Bonutti |
| 2009/0194969 A1 | 8/2009 | Bearey |
| 2010/0211120 A1 | 8/2010 | Bonutti et al. |
| 2010/0312350 A1 | 12/2010 | Bonutti |
| 2011/0060375 A1 | 3/2011 | Bonutti |
| 2011/0295253 A1 | 12/2011 | Bonutti et al. |
| 2012/0010623 A1 | 1/2012 | Bonutti |
| 2012/0165841 A1 | 6/2012 | Bonutti |
| 2012/0191140 A1 | 7/2012 | Bonutti |
| 2012/0215226 A1 | 8/2012 | Bonutti |
| 2012/0215233 A1 | 8/2012 | Bonutti et al. |
| 2012/0221017 A1 | 8/2012 | Bonutti |
| 2013/0144389 A1 | 6/2013 | Bonutti |
| 2013/0226185 A1 | 8/2013 | Bonutti |
| 2013/0226311 A1 | 8/2013 | Bonutti |
| 2014/0018852 A1 | 1/2014 | Bonutti |
| 2014/0018853 A1 | 1/2014 | Bonutti |
| 2014/0018854 A1 | 1/2014 | Bonutti |
| 2014/0025110 A1 | 1/2014 | Bonutti |
| 2014/0025111 A1 | 1/2014 | Bonutti |
| 2014/0025112 A1 | 1/2014 | Bonutti |

FOREIGN PATENT DOCUMENTS

| | | |
|---|---|---|
| CA | 2680827 | 9/2008 |
| CA | 2698057 | 3/2009 |
| CH | 117960 A | 5/1927 |
| DE | 337437 C | 5/1921 |
| DE | 605255 C | 11/1934 |
| DE | 1903016 | 10/1964 |
| DE | 1903316 | 10/1964 |
| DE | 1903016 | 8/1970 |
| DE | 2411226 A1 | 9/1974 |
| DE | 32 11 682 | 10/1983 |
| DE | 3517204 | 11/1986 |
| DE | 37 07 787 A1 | 9/1988 |
| DE | 3722538 | 1/1989 |
| DE | 90 02 844.9 U1 | 1/1991 |
| DE | 9002844 U1 | 1/1991 |
| EP | 0 010 650 A1 | 5/1980 |
| EP | 0 192 576 A1 | 8/1986 |
| EP | 0 283 661 A2 | 9/1988 |
| EP | 0 287 998 A2 | 10/1988 |
| EP | 0 418 147 A1 | 3/1991 |
| EP | 0 699 416 | 3/1996 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 325846 A | 5/1903 |
| FR | 726041 A | 5/1932 |
| FR | 1 111 677 A | 3/1956 |
| FR | 2 344 267 A1 | 10/1977 |
| FR | 2 580 504 A1 | 10/1986 |
| FR | 2 682 287 A1 | 4/1993 |
| FR | 2717368 | 3/1994 |
| FR | 2 696 338 | 4/1994 |
| FR | 2696338 | 4/1994 |
| FR | 2728779 | 1/1995 |
| FR | 2736257 | 7/1995 |

(56) References Cited

FOREIGN PATENT DOCUMENTS

| | | |
|---|---|---|
| FR | 2750031 | 6/1996 |
| FR | 2771621 | 11/1997 |
| FR | 2785171 | 10/1998 |
| GB | 214913 A | 5/1924 |
| GB | 2093701 A | 9/1982 |
| GB | 2306110 A | 4/1997 |
| JP | S6429266 A | 1/1989 |
| JP | 8140982 | 6/1996 |
| JP | H08173436 | 7/1996 |
| JP | 3738221 | 1/2006 |
| SU | 184396 | 7/1966 |
| SU | 1323090 A1 | 7/1987 |
| SU | 1367947 A1 | 1/1988 |
| WO | WO 87/01270 A1 | 3/1987 |
| WO | WO 88/01517 A1 | 3/1988 |
| WO | 91/12779 | 9/1991 |
| WO | 93/23094 | 11/1993 |
| WO | WO 93/23094 | 11/1993 |
| WO | WO9408642 | 4/1994 |
| WO | 95/16398 | 6/1995 |
| WO | WO 95/16398 | 6/1995 |
| WO | WO 95/31941 | 11/1995 |
| WO | WO9614802 | 5/1996 |
| WO | WO 96/29029 | 9/1996 |
| WO | WO9712779 | 4/1997 |
| WO | WO 97/20522 | 6/1997 |
| WO | WO 97/39700 | 10/1997 |
| WO | 97/49347 | 12/1997 |
| WO | WO 97/49347 | 12/1997 |
| WO | WO9811838 | 3/1998 |
| WO | WO9826720 | 6/1998 |
| WO | WO 01/34036 A1 | 5/2001 |
| WO | WO02053011 | 7/2002 |
| WO | 2007/092869 | 8/2007 |
| WO | 2007/092869 A2 | 8/2007 |
| WO | 2008/116203 | 9/2008 |
| WO | 2009/029908 | 3/2009 |
| WO | WO2010099222 | 2/2010 |

OTHER PUBLICATIONS

R. John Naranja, Jr. M.D. et al., A Review Paper entitled: The Search for the Holy Grail: a Century of Anterior Cruciate Ligament Reconstruction, The American Journal of Orthopedics, Nov. 1997, pp. 743-752.
Walter R. Shelton, M.D. et al., Technical Note, entitled: Meniscus Replacement with Bone Anchors: A Surgical Technique, Arthroscopy: The Journal of Arthroscopic and Related Surgery, vol. 10, No. 3, 1994, pp. 324-327.
010-3 Copending U.S. Appl. No. 11/932,907—RCE Response Sep. 15, 2011.
027 Copending U.S. Appl. No. 11/258,795 Non-Final Office Action mailed Apr. 26, 2011.
046 Copending U.S. Appl. No. 11/689,670, RCE Response Sep. 19, 2011.
European Search Report dated Sep. 10, 2012 for EP08732724.3 (046).
003-1 Copending U.S. Appl. No. 10/614,352, Final Office Action Jul. 12, 2010.
007-2 Copending U.S. Appl. No. 11/932,602 Final Response to Office Action Jun. 10, 2011.
039 Copending U.S. Appl. No. 11/671,556 Response filed Aug. 23, 2010.
The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.

Problem Solving Report Question No. 1014984.066, Ultrasonic Welding, (c) 1999.
Guide to Ultrasound Plastic Assembly, Ultrasonic Division Publication, (c) 1995.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
IPR—International Publication WO/2007/092869, publishedAug. 16, 2007 for PCT/US2007/061730.
ISR—International Search Report WO/2007/092869, published Dec. 13, 2007 for PCT/US2007/061730.
Intl Prelim Report on Patentability, WO/2007/092869, published Aug. 12, 2008 for PCT/US2007/061730.
Written Opinion WO/2007/092869 dated Aug. 7, 2008 for PCT/US2007/061730.
IPR—International Publication WO/2008/116203, published Sep. 22, 2009 for PCT/US08/57948.
ISR—International Search Report WO/2008/116203, published Dec. 24, 2008 for PCT/US08/57948.
IPER—Internation Preliminary Report on Patentability, WO/2008/116203, published Sep. 22, 2009 for PCT/US08/57948.
Written Opinion WO/2008/116203 dated Oct. 23, 2008 for PCT/US08/57948.
IPR—International Publication WO2009/029908, published May 3, 2009 for PCT/US08/74941.
ISR—International Search Report, WO2009/029908, published May 3, 2009 for PCT/US08/74941.
IPER—Internation Preliminary Report on Patentability, WO2009/029908, published Mar. 2, 2010 for PCT/US08/74941.
Written Opinion WO2009/029908 dated Feb. 28, 2010 for PCT/US08/74941.
International Search Report PCT/US2010/025263 completed Apr. 13, 2010.
Written Opinion for PCT/US2010/025263 completed Apr. 13, 2010.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 95, Arthroscopy vol. 11 No. 2 p. 245-251.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.

(56) References Cited

OTHER PUBLICATIONS

Nowak et al, Comparative Study of Fixation Techniques in the Open Bankart Operation Using Either a Cannulated Screw or Suture-Anchors, Acta Orthopcedica Belgica, vol. 64—Feb. 1998.

Packer et al, Repair of Acute Scapho-Lunate Dissociation Facilitated by the "TAG" Suture Anchor, Journal of Hand Surgery (British and European Volume, 1994) 19B: 5: 563-564.

Richmond, Modificatio of the Bankart reconstruction with a suture anchor, Am J Sports Med, vol. 19, No. 4, p. 343-346, 1991.

Shea et al, Technical Note: Arthroscopic Rotator Cuff Repair Using a Transhumeral Approach to Fixation, Arthroscopy: The Journal of Arthroscopic and Related Surgery, vol. 14, No. 1 Jan.-Feb. 1998: pp. 118-122.

Tfix, Acufex just tied the knot . . . , Am. J. Sports Med., vol. 22, No. 3, May-Jun. 1994.

Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 Feb. 2010: pp. 286-290.

Cobb et al, Late Correction of Malunited Intercondylar Humeral Fractures Intra-Articular Osteotomy and Tricortical Bone Grafting, J BoneJointSurg [Br] 1994; 76-B:622-6.

Fellinger, et al, Radial avulsion of the triangular fibrocartilage complex in acute wrist trauma: a new technique for arthroscopic repair, Jun. 97, Arthroscopy vol. 13 No. 3 p. 370-374.

Hecker et al , Pull-out strength of suture anchors for rotator cuff and Bankart lesion repairs, Nov.-Dec. 1993, The American Journal of Sports Medicine, vol. 21 No. 6 p. 874-879.

Hernigou et al , Proximal Tibial Osteotomy for Osteoarthritis with Varus Deformity A Ten to Thirteen-Year Follow-Up Study, J Bone Joint Surg, vol. 69-A, No. 3. Mar. 1987, p. 332-354.

Ibarra et al, Glenoid Replacement in Total Shoulder Arthroplasty, The Orthopedic Clinics of Northamerica: Total Shoulder Arthroplasty, vol. 29 No. 3, Jul. 1998 p. 403-413.

Murphycet al , Radial Opening Wedge Osteotomy in Madelung's Deformity, J. Hand Surg, vol. 21 A No. 6 Nov. 1996, p. 1035-1044.

Biomet, Stanmore Modular Hip, J. Bone Joint Surg., vol. 76-B : Number Two, Mar. 1994.

Intl Prelim Rep on Patentability and Written Opinion for PCT/US10/25263 dated Aug. 30, 2011.

Petition for Inter Partes Review of U.S. Patent No. 5,980,559, IPR 2013-00603, Filing Date Sep. 24, 2013.

Petition for Inter Partes Review of U.S. Patent No. 7,087,073, IPR 2013-00604, Filing Date Sep. 24, 2013.

Declaration of Wayne J. Sebastianelli, MD Regarding U.S. Patent No. 7,087,073, Sep. 24, 2013, IPR 2013-00604.

Petition for Inter Partes Review of U.S. Patent No. 6,500,195, IPR 2013-00624, Filing Date Oct. 2, 2013.

Declaration of Dr. Philip Hardy in Support of Petition for Inter Partes Review of U.S. Patent No. 6,500,195, IPR 2013-00624, Sep. 25, 2013.

Petition for Inter Partes Review of U.S. Patent No. 5,527,343, IPR 2013-00628, Filing Date Sep. 26, 2013, Sep. 25, 2013.

Corrected Petition for Inter Partes Review of US Patent No. 5,921,986, IPR 2013-00631, Filing Date Sep. 27, 2013.

Expert Declaration of Steve E. Jordan, MD, for Inter Partes Review of US Patent No. 5,921,986, IPR 2013-00631, Sep. 24, 2013.

Corrected Petition for Inter Partes Review of US Patent No. 8,147,514, IPR 2013-00632, Filing Date Sep. 27, 2013.

Declaration of Steve Jordan for USP 8,147,514, from IPR 2013-00632, dated Sep. 23, 2013 (exhibit 1009).

Corrected Petition For Inter Partes Review Of US Patent No. 8,147,514, IPR 2013-00633, Filing Date Sep. 27, 2013.

Declaration of Steve Jordan for USP 8,147,514, from IPR 2013-00633, dated Sep. 23, 2013 (exhibit 1006).

Flory, Principles of Polymer Chemistry, 1953, selected pages (IPR 2013-00603, exhibit 1012).

Grizzi, Hydrolytic degradation of devices based on poly(DL-lactic acid) size-dependence, Biomaterials, 1995, vol. 16, No. 4, p. 305-311 (IPR 2013-00603, exhibit 1006).

Gopferich, Mechanisms of polymer degradation and erosion, Biomaterials, 1996, vol. 17, No. 2, p. 103-114 (IPR 2013-00603, exhibit 1013).

Gao et el, Swelling of Hydroxypropyl Methylcellulose Matrix Tablets . . . , J. of Pharmaceutical Sciences, vol. 85, No. 7, Jul. 1996, p. 732-740 (IPR 2013-00603, exhibit 1014).

Linvatec, Impact Suture Anchor brochure, 2004 (IPR 2013-00628, exhibit 1010).

Seitz et al, Repair of the Tibiofibular Syndesmosis with a Flexible Implant, J. of Orthopaedic Trauma, vol. 5, No. 1, p. 78-82, 1991 (IPR 2013-00631, exhibit 1007) (2013-00632).

Translation of FR2696338 with translators certificate dated Sep. 17, 2013 (IPR 2013-00631, 2013-00632).

Translation of DE9002844.9 with translator's certificate dated Sep. 26, 2013 (IPR 2013-00631, 2013-00632).

Declaration of Steve Jordan for USP 5921986, from IPR 2013-00632, dated Sep. 24, 2013 (exhibit 1010).

Declaration of Steve Jordan for USP 5921986, from IPR 2013-00633, dated Sep. 24, 2013 (exhibit 1007).

Declaration of Dr. Steve E. Jordan for USP 8,147,514, from IPR 2013-00631, dated Sep. 23, 2013.

U.S. Appl. No. 13/221,043, Jun. 2011, Bonutti.

Copending U.S. Appl. No. 09/556,458, Non-Final Rejection mailed Sep. 25, 2002.

Copending U.S. Appl. No. 09/556,458, Response to Office Action Dec. 26, 2002.

Copending U.S. Appl. No. 10/614,352, Examiner Interview Summary Jul. 31, 2007.

Copending U.S. Appl. No. 10/614,352, Final Rejection mailed Jan. 25, 2007.

Copending U.S. Appl. No. 10/614,352, Final Rejection mailed Apr. 14, 2009.

Copending U.S. Appl. No. 10/614,352, Final Rejection mailed Oct. 2, 2007.

Copending U.S. Appl. No. 10/614,352, non Final Office Action Aug. 10, 2011.

Copending U.S. Appl. No. 10/614,352, Non-Final Rejection mailed Jan. 15, 2008.

Copending U.S. Appl. No. 10/614,352, Non-Final Rejection mailed Apr. 17, 2007.

Copending U.S. Appl. No. 10/614,352, Non-Final Rejection mailed Aug. 1, 2006.

Copending U.S. Appl. No. 10/614,352, Non-Final Rejection mailed Aug. 21, 2008.

Copending U.S. Appl. No. 10/614,352, Non-Final Rejection mailed Nov. 24, 2009.

Copending U.S. Appl. No. 10/614,352, Non-Final Rejection mailed Dec. 1, 2005.

Copending U.S. Appl. No. 10/614,352, Request for Continued Examination Sep. 14, 2009.

Copending U.S. Appl. No. 10/614,352, Request for Continued Examination Oct. 30, 2007.

Copending U.S. Appl. No. 10/614,352, Response to Office Action Mar. 1, 2006.

Copending U.S. Appl. No. 10/614,352, Response to Office Action Mar. 26, 2007.

Copending U.S. Appl. No. 10/614,352, Response to Office Action Apr. 26, 2010.

Copending U.S. Appl. No. 10/614,352, Response to Office Action May 15, 2008.

Copending U.S. Appl. No. 10/614,352, Response to Office Action Jul. 17, 2007.

Copending U.S. Appl. No. 10/614,352, Response to Office Action Sep. 14, 2009.

Copending U.S. Appl. No. 10/614,352, Response to Office Action Oct. 30, 2007.

Copending U.S. Appl. No. 10/614,352, Response to Office Action Nov. 1, 2006.

Copending U.S. Appl. No. 10/614,352, Response to Office Action Dec. 22, 2008.

(56) References Cited

OTHER PUBLICATIONS

Copending U.S. Appl. No. 11/931,823 final Office Action mailed Aug. 2, 2011.
Copending U.S. Appl. No. 11/931,823 Office Action mailed Nov. 24, 2010.
Copending U.S. Appl. No. 11/931,823 Response to Office Action Aug. 9, 2010.
Copending U.S. Appl. No. 11/931,823 RestrictionElect dated Jun. 8, 2010.
Copending U.S. Appl. No. 11/187,482 Response to Office Action Jun. 21, 2011.
Copending U.S. Appl. No. 10/413,696, Non-Final Rejection mailed Sep. 23, 2005.
Copending U.S. Appl. No. 10/413,696, Requirement for Restriction Jun. 8, 2005.
Copending U.S. Appl. No. 10/413,696, Response to Office Action Jul. 5, 2005.
Copending U.S. Appl. No. 10/413,696, Response to Office Action Dec. 20, 2005.
Copending U.S. Appl. No. 11/460,650, Examiner Interview Summary mailed Dec. 23, 2009.
Copending U.S. Appl. No. 11/460,650, Final Rejection mailed Apr. 20, 2010.
Copending U.S. Appl. No. 11/460,650, Final Rejection mailed Aug. 29, 2008.
Copending U.S. Appl. No. 11/460,650, Non-Final Rejection mailed Mar. 10, 2009.
Copending U.S. Appl. No. 11/460,650, Non-Final Rejection mailed May 30, 2007.
Copending U.S. Appl. No. 11/460,650, Non-Final Rejection mailed Sep. 16, 2009.
Copending U.S. Appl. No. 11/460,650, Non-Final Rejection mailed Dec. 28, 2007.
Copending U.S. Appl. No. 11/460,650, Request for Continued Examination Jan. 29, 2009.
Copending U.S. Appl. No. 11/460,650, Response to Office Action Jan. 12, 2010.
Copending U.S. Appl. No. 11/460,650, Response to Office Action Jan. 29, 2009.
Copending U.S. Appl. No. 11/460,650, Response to Office Action Mar. 28, 2008.
Copending U.S. Appl. No. 11/460,650, Response to Office Action Jun. 10, 2009.
Copending U.S. Appl. No. 11/460,650, Response to Office Action Oct. 1, 2007.
Copending U.S. Appl. No. 11/461,110, Final Rejection mailed Dec. 8, 2009.
Copending U.S. Appl. No. 11/461,110, Non-Final Rejection mailed Apr. 22, 2009.
Copending U.S. Appl. No. 11/461,110, Non-Final Rejection mailed Jun. 6, 2008.
Copending U.S. Appl. No. 11/461,110, Request for Continued Examination Mar. 12, 2008.
Copending U.S. Appl. No. 11/461,110, Request for Continued Examination Jun. 8, 2010.
Copending U.S. Appl. No. 11/461,110, Response to Office Action Mar. 12, 2008.
Copending U.S. Appl. No. 11/461,110, Response to Office Action Jun. 8, 2010.
Copending U.S. Appl. No. 11/461,110, Response to Office Action Sep. 22, 2009.
Copending U.S. Appl. No. 11/461,110, Response to Office Action Oct. 6, 2008.
Copending U.S. Appl. No. 11/461,110, Response to Office Action Oct. 15, 2007.
Copending U.S. Appl. No. 11/461,110, Final Rejection mailed Dec. 12, 2007.
Copending U.S. Appl. No. 11/461,110, Non-Final Rejection mailed May 14, 2007.
Copending U.S. Appl. No. 11/930,621, Final Rejection Jun. 22, 2010.
Copending U.S. Appl. No. 11/930,621, Non-Final Rejection mailed Sep. 21, 2009.
Copending U.S. Appl. No. 11/930,621, Response to Office Action Mar. 22, 2010.
Copending U.S. Appl. No. 09/524,397, Final Rejection mailed Jun. 15, 2001.
Copending U.S. Appl. No. 09/524,397, Non-Final Rejection mailed Dec. 18, 2000.
Copending U.S. Appl. No. 09/524,397, Response to Office Action Mar. 19, 2001.
Copending U.S. Appl. No. 09/524,397, Response to Office Action Oct. 15, 2001.
Copending U.S. Appl. No. 10/458,117, Advisory Action Jan. 20, 2006.
Copending U.S. Appl. No. 10/458,117, Examiner Interview Summary mailed May 16, 2008.
Copending U.S. Appl. No. 10/458,117, Non-Final Rejection mailed Mar. 22, 2005.
Copending U.S. Appl. No. 10/458,117, Non-Final Rejection mailed Nov. 15, 2006.
Copending U.S. Appl. No. 10/458,117, Request for Continued Examination Feb. 26, 2008.
Copending U.S. Appl. No. 10/458,117, Request for Continued Examination Feb. 21, 2006.
Copending U.S. Appl. No. 10/458,117, Request for Continued Examination Aug. 3, 2007.
Copending U.S. Appl. No. 10/458,117, Response to Office Action Feb. 13, 2007.
Copending U.S. Appl. No. 10/458,117, Response to Office Action Jun. 22, 2005.
Copending U.S. Appl. No. 10/458,117, Response to Office Action Aug. 3, 2007.
Copending U.S. Appl. No. 10/458,117, Response to Office Action Nov. 8, 2005.
Copending U.S. Appl. No. 10/458,117, Final Rejection mailed May 3, 2007.
Copending U.S. Appl. No. 10/458,117, Final Rejection mailed Sep. 8, 2005.
Copending U.S. Appl. No. 11/370,775, Examiner Interview Summary mailed Oct. 29, 2007.
Copending U.S. Appl. No. 11/370,775, Examiner Interview Summary mailed Apr. 24, 2008.
Copending U.S. Appl. No. 11/370,775, Examiner Interview Summary mailed Feb. 27, 2009.
Copending U.S. Appl. No. 11/370,775, Examiner Interview Summary mailed Aug. 28, 2009.
Copending U.S. Appl. No. 11/370,775, Non-Final Rejection mailed Feb. 6, 2007.
Copending U.S. Appl. No. 11/370,775, Non-Final Rejection mailed Jan. 22, 2008.
Copending U.S. Appl. No. 11/370,775, Non-Final Rejection mailed Oct. 15, 2008.
Copending U.S. Appl. No. 11/370,775, Non-Final Rejection mailed Nov. 6, 2009.
Copending U.S. Appl. No. 11/370,775, Response to Office Action Jun. 4, 2007.
Copending U.S. Appl. No. 11/370,775, Response to Office Action Oct. 26, 2007.
Copending U.S. Appl. No. 11/370,775, Response to Office Action May 22, 2008.
Copending U.S. Appl. No. 11/370,775, Response to Office Action Jan. 15, 2009.
Copending U.S. Appl. No. 11/370,775, Response to Office Action Aug. 13, 2009.
Copending U.S. Appl. No. 11/370,775, Response to Office Action May 6, 2010.
Copending U.S. Appl. No. 11/370,775, Supplemental Response to Office Action Jan. 30, 2009.
Copending U.S. Appl. No. 11/370,775, Final Rejection mailed Aug. 31, 2007.
Copending U.S. Appl. No. 11/370,775, Final Rejection mailed Mar. 13, 2009.

(56) References Cited

OTHER PUBLICATIONS

Copending U.S. Appl. No. 11/370,775, Request for Continued Examination Oct. 26, 2007.
Copending U.S. Appl. No. 11/370,775, Request for Continued Examination Jan. 10, 2011.
Copending U.S. Appl. No. 11/370,775, Request for Continued Examination Aug. 13, 2009.
Copending U.S. Appl. No. 11/456,132, Examiner Interview Summary mailed Aug. 28, 2009.
Copending U.S. Appl. No. 11/456,132, Request for Continued Examination Jun. 11, 2008.
Copending U.S. Appl. No. 11/456,132, Response to Office Action Jan. 7, 2009.
Copending U.S. Appl. No. 11/456,132, Response filed Jan. 18, 2012.
Copending U.S. Appl. No. 11/456,132, Response to Office Action Apr. 14, 2011.
Copending U.S. Appl. No. 11/456,132, Response to Office Action Apr. 19, 2010.
Copending U.S. Appl. No. 11/456,132, Response to Office Action Jun. 11, 2008.
Copending U.S. Appl. No. 11/456,132, Response to Office Action Aug. 13, 2009.
Copending U.S. Appl. No. 11/456,132, Response to Office Action Nov. 19, 2007.
Copending U.S. Appl. No. 11/456,132, Final Rejection mailed Mar. 11, 2008.
Copending U.S. Appl. No. 11/456,132, Final Rejection mailed Dec. 18, 2009.
Copending U.S. Appl. No. 11/456,132, Non-Final Rejection mailed Mar. 13, 2009.
Copending U.S. Appl. No. 11/456,132, Non-Final Rejection mailed Jun. 18, 2007.
Copending U.S. Appl. No. 11/456,132, Non-Final Rejection mailed Oct. 7, 2008.
Copending U.S. Appl. No. 11/456,221, Final Rejection mailed Feb. 22, 2008.
Copending U.S. Appl. No. 11/456,221, Final Rejection mailed Mar. 24, 2010.
Copending U.S. Appl. No. 11/456,221, Non-Final Rejection mailed Jul. 6, 2009.
Copending U.S. Appl. No. 11/456,221, Non-Final Rejection mailed Jul. 9, 2007.
Copending U.S. Appl. No. 11/456,221, Non-Final Rejection mailed Oct. 29, 2008.
Copending U.S. Appl. No. 11/456,221, Request for Continued Examintation Jun. 19, 2008.
Copending U.S. Appl. No. 11/456,221, Response to Office Action Jan. 6, 2010.
Copending U.S. Appl. No. 11/456,221, Response to Office Action Mar. 30, 2009.
Copending U.S. Appl. No. 11/456,221, Response to Office Action May 22, 2008.
Copending U.S. Appl. No. 11/456,221, Response to Office Action Nov. 9, 2007.
Copending U.S. Appl. No. 11/932,051 Final Office Action mailed Jun. 9, 2011.
Copending U.S. Appl. No. 11/932,051, RCE Response Dec. 9, 2011.
Copending U.S. Appl. No. 11/932,051, Requirement for Restriction Jan. 22, 2010.
Copending U.S. Appl. No. 10/228,855, Non-Final Rejection mailed Sep. 28, 2005.
Copending U.S. Appl. No. 10/228,855, Response to Office Action Dec. 28, 2005.
Copending U.S. Appl. No. 11/465,199, Response to Office Action Jun. 28, 2010.
Copending U.S. Appl. No. 11/465,199, Non-Final Rejection mailed Dec. 28, 2009.
Copending U.S. Appl. No. 11/932,602 non final Office Action Oct. 6, 2010.
Copending U.S. Appl. No. 11/932,602, Response to Office Action Apr. 6, 2011.
Copending U.S. Appl. No. 12/359,364, Final Office Action Apr. 7, 2011.
Copending U.S. Appl. No. 11/438,537—RCE Response Nov. 21, 2011.
Copending U.S. Appl. No. 11/932,907, non-final Office Action Nov. 17, 2010.
Copending U.S. Appl. No. 11/932,907, Response to Office Action Apr. 18, 2011.
Copending U.S. Appl. No. 11/133,730 Final Office action Aug. 17, 2011.
Copending U.S. Appl. No. 11/169,475—Response Sep. 2, 2011.
Copending U.S. Appl. No. 11/169,475 Office Action Mar. 2, 2011.
Copending U.S. Appl. No. 11/126,543 non Final Office Action Aug. 10, 2011.
Copending U.S. Appl. No. 11/126,543 RCE Response filed Jun. 30, 2011.
Copending U.S. Appl. No. 10/780,444, Examiner Interview Summary mailed Nov. 20, 2009.
Copending U.S. Appl. No. 10/780,444, Final Rejection mailed Mar. 30, 2010.
Copending U.S. Appl. No. 10/780,444, Final Rejection mailed Dec. 23, 2008.
Copending U.S. Appl. No. 10/780,444, nonFinal Office Action Aug. 9, 2011.
Copending U.S. Appl. No. 10/780,444, Non-Final Rejection mailed Mar. 11, 2008.
Copending U.S. Appl. No. 10/780,444, Non-Final Rejection mailed Jul. 7, 2009.
Copending U.S. Appl. No. 10/780,444, Request for Continued Examination Apr. 23, 2009.
Copending U.S. Appl. No. 10/780,444, Requirement for Restriction Sep. 12, 2007.
Copending U.S. Appl. No. 10/780,444, Requirement for Restriction Apr. 10, 2007.
Copending U.S. Appl. No. 10/780,444, Response filed Feb. 9, 2012.
Copending U.S. Appl. No. 10/780,444, Response to Office Action Apr. 23, 2009.
Copending U.S. Appl. No. 10/780,444, Response to Office Action May 10, 2007.
Copending U.S. Appl. No. 10/780,444, Response to Office Action Jul. 9, 2008.
Copending U.S. Appl. No. 10/780,444, Response to Office Action Oct. 12, 2007.
Copending U.S. Appl. No. 10/780,444, Response to Office Action Dec. 4, 2009.
Copending U.S. Appl. No. 10/779,978 Non-Final Office Action mailed Jan. 13, 2011.
Copending U.S. Appl. No. 10/779,978, Final Rejection mailed Feb. 3, 2009.
Copending U.S. Appl. No. 10/779,978, Final Rejection mailed May 14, 2010.
Copending U.S. Appl. No. 10/779,978, Non-Final Rejection mailed Jun. 18, 2008.
Copending U.S. Appl. No. 10/779,978, Non-Final Rejection mailed Aug. 3, 2007.
Copending U.S. Appl. No. 10/779,978, Non-Final Rejection mailed Oct. 1, 2009.
Copending U.S. Appl. No. 10/779,978, Request for Continued Examination Jul. 6, 2009.
Copending U.S. Appl. No. 10/779,978, Requirement for Restriction Apr. 20, 2007.
Copending U.S. Appl. No. 10/779,978, Response to Office Action Feb. 1, 2010.
Copending U.S. Appl. No. 10/779,978, Response to Office Action Mar. 25, 2008.
Copending U.S. Appl. No. 10/779,978, Response to Office Action May 21, 2007.
Copending U.S. Appl. No. 10/779,978, Response to Office Action Jul. 6, 2009.
Copending U.S. Appl. No. 10/779,978, Response to Office Action Jul. 13, 2011.

(56) References Cited

OTHER PUBLICATIONS

Copending U.S. Appl. No. 10/779,978, Response to Office Action Oct. 20, 2008.
Copending U.S. Appl. No. 10/779,978, Response to Office Action Dec. 3, 2007.
Copending U.S. Appl. No. 10/797,685, Examiner Interview Summary mailed Sep. 11, 2007.
Copending U.S. Appl. No. 10/797,685, Final Rejection mailed Apr. 25, 2007.
Copending U.S. Appl. No. 10/797,685, Non-Final Rejection mailed Nov. 17, 2006.
Copending U.S. Appl. No. 10/797,685, Response to Office Action Feb. 20, 2007.
Copending U.S. Appl. No. 10/797,685, Response to Office Action Aug. 27, 2007.
Copending U.S. Appl. No. 11/874,323 Office Action mailed Jul. 6, 2011.
Copending U.S. Appl. No. 11/874,323 Response filed Apr. 21, 2011.
Copending U.S. Appl. No. 11/202,294, Office Action mailed Jun. 24, 2011.
Copending U.S. Appl. No. 11/202,294, Response filed Dec. 24, 2011.
Copending U.S. Appl. No. 11/358,399 non Final Office Action Jan. 3, 2011.
Copending U.S. Appl. No. 11/358,399 Response filed Jul. 5, 2011.
Copending U.S. Appl. No. 11/671,556 Final Office Action mailed Nov. 12, 2010.
Copending U.S. Appl. No. 11/671,556, Non-Final Rejection mailed Feb. 22, 2010.
Copending U.S. Appl. No. 11/671,556, Requirement for Restriction Sep. 1, 2009.
Copending U.S. Appl. No. 11/671,556, Response to Office Action Nov. 2, 2009.
Copending U.S. Appl. No. 11/416,618, Examiner Interview Summary mailed Apr. 15, 2010.
Copending U.S. Appl. No. 11/416,618, Final Rejection mailed Jun. 24, 2009.
Copending U.S. Appl. No. 11/416,618, Non-Final Rejection mailed Oct. 13, 2009.
Copending U.S. Appl. No. 11/416,618, Non-Final Rejection mailed Nov. 26, 2008.
Copending U.S. Appl. No. 11/416,618, Response to Office Action Mar. 15, 2010.
Copending U.S. Appl. No. 11/416,618, Response to Office Action Mar. 26, 2009.
Copending U.S. Appl. No. 11/416,618, Response to Office Action Apr. 16, 2010.
Copending U.S. Appl. No. 11/416,618, Response to Office Action Sep. 24, 2009.
Copending U.S. Appl. No. 11/416,618, Request for Continued Examination Dec. 8, 2010.
Copending U.S. Appl. No. 11/689,670, Final Office Action mailed Mar. 17, 2011.
Copending U.S. Appl. No. 11/689,670, Requirement for Restriction Mar. 15, 2010.
Copending U.S. Appl. No. 11/689,670, Response to Office Action Jan. 3, 2011.
Copending U.S. Appl. No. 11/689,670, Response to Office Action Apr. 15, 2010.
Copending U.S. Appl. No. 11/202,210, Requirement for Restriction mailed Aug. 16, 2011.
Copending U.S. Appl. No. 12/202,210, Response filed Dec. 16, 2011.
Co-pending U.S. Appl. No. 11/438,537, Supplemental Final Rejection mailed Sep. 25, 2009.
File History of U.S. Patent No. 5,403,348; U.S. Appl. No. 08/062,295; filed May 14, 1993; 231 pages.
File History of U.S. Patent No. 5,522,846; U.S. Appl. No. 08/402,352; filed Mar. 10, 1995; 215 pages.
File History of U.S. Patent No. 5,527,343; U.S. Appl. No. 08/344,466; filed Nov. 23, 1994; 246 pages.
File History of U.S. Patent No. 5,549,630; U.S. Appl. No. 08/291,970; filed Aug. 17, 1994; 276 pages.
File History of U.S. Patent No. 5,980,559; U.S. Appl. No. 08/964,167; filed Nov. 4, 1997; 57 pages.
File History of U.S. Patent No. 6,500,195; U.S. Appl. No. 09/872,033; filed Jun. 1, 2001; 522 pages.
File History of U.S. Patent No. 7,087,073; U.S. Appl. No. 10/413,696; filed Apr. 14, 2003; 13 pages.
Petition for *Inter Partes* Review of U.S. Patent No. 5,980,559 Under 35 U.S.C. § 312 and 37 C.F.R. § 42.104; filed Sep. 24, 2013; IPR2013-00603; with exhibits, 382 pages.
Declaration of David Kaplan, Ph.D. Regarding U.S. Patent No. 5,980,559, IPR 2013-00603, Sep. 24, 2013.
Petition for *Inter Partes* Review of U.S. Patent No. 7,087,073 Under 35 U.S.C. § 312 and 37 C.F.R. § 42.104; filed Sep. 24, 2013; IPR2013-00604; with exhibits, 243 pages.
Declaration of Wayne J. Sebastianelli, MD Regarding U.S. Patent No. 7,087,073, Sep. 24, 2013,IPR 2013-00604.
Petition for *Inter Partes* Review of U.S. Patent No. 6,500,195 Under 35 U.S.C. § 312 and 37 C.F.R. § 42.104; filed Sep. 25, 2013; IPR2013-00624; with exhibits, 1152 pages.
Declaration of Dr. Philip Hardy in Support of Petition for *Inter Partes* Review of U.S. Patent No. 6,500,195, IPR 2013-00624.
Petition for *Inter Partes* Review of U.S. Patent No. 5,527,343 Under 35 U.S.C. § 312 and 37 C.F.R. § 42.104; filed Sep. 26, 2013; IPR2013-00628; with exhibits, 882 pages.
Declaration of Dr. Philip Hardy in Support of Petition for *Inter Partes* Review of U.S. Patent No. 5,527,343, IPR 2013-00628, Sep. 25, 2013.
Corrected Petition for *Inter Partes* Review of U.S. Patent No. 5,921,986 Under 35 U.S.C. §§ 311-319 and 37 C.F.R. § 42.100 Et Seq.; filed Oct. 11, 2013; IPR2013-00631; with exhibits, 285 pages.
Expert Declaration of Steve E. Jordan, MD, for *Inter Partes* Review of U.S. Patent No. 5,921,986, IPR 2013-00631, Sep. 24, 2013.
Corrected Petition for *Inter Partes* Review of U.S. Patent No. 8,147,514 Under 35 U.S.C. §§ 311-319 and 37 C.F.R. § 42.100 Et Seq.; filed Oct. 11, 2013; IPR2013-00632; with exhibits, 268 pages.
Declaration of Steve E. Jordan for U.S. Patent No. 8,147,514, IPR 2013-00631, dated Sep. 23, 2013.
Declaration of Dr. Steve E. Jordan for U.S. Patent No. 8,147,514, IPR 2013-00631, Sep. 23, 2013.
Declaration of Steve E. Jordan for U.S. Patent No. 5,921,986, from IPR 2013-00632, dated Sep. 24, 2013 (exhibit 1010).
Declaration of Steve E. Jordan for U.S. Patent No. 5,921,986, from IPR 2013-00633, dated Sep. 24, 2013 (exhibit 1007).
Corrected Petition for *Inter Partes* Review of U.S. Patent No. 8,147,514 Under 35 U.S.C. §§ 311-319 and 37 C.F.R. § 42.100 Et. Seq.; filed Oct. 11, 2013; IPR2013-00633; with exhibits, 248 pages.
*Bonutti Skeletal Innovations LLC* v. *Linvatec Corporation and ConMed Corporation*; "Defendants Linvatec and ConMed Corporation's Invalidity Contentions;" With Exhibits; Case No. 6:12-cv-01379; M.D. Florida; Sep. 30, 2013; 2703 pages.
*Bonutti Skeletal Innovations LLC* v. *Linvatec Corporation and ConMed Corporation*; "Defendants Linvatec and ConMed Corporation's Non-Infringement Contentions;" With Exhibits; Case No. 6:12-cv-01379; M.D. Florida; Sep. 30, 2013; 310 pages.
*Bonutti Skeletal Innovations LLC* v. *Linvatec Corporation and ConMed Corporation*; "Defendants' Proposed Claim Term Constructions;" With Exhibits; Case No. 6:12-cv-01379; M.D. Florida; Nov. 1, 2013; 53 pages.
*Bonutti Skeletal Innovations LLC* v. *Linvatec Corporation and ConMed Corporation*; "Defendants' Proposed Terms for Construction;" Case No. 6:12-cv-01379; M.D. Florida; Oct. 10, 2013; 9 pages.
*Bonutti Skeletal Innovations LLC* v. *Linvatec Corporation and ConMed Corporation*; "Joint Claim Construction Statement;" With Exhibits; Case No. 6:12-cv-01379; M.D. Florida; Nov. 15, 2013; 55 pages.
*Bonutti Skeletal Innovations LLC* v. *Linvatec Corporation and ConMed Corporation*; "Plaintiff Bonutti Skeletal Innovations LLC's Initial Identification of Disputed Claim Terms;" Case No. 6:12-cv-01379; M.D. Florida; Oct. 10, 2013; 3 pages.
*Bonutti Skeletal Innovations LLC* v. *Linvatec Corporation and ConMed Corporation*; "Plaintiff Bonutti Skeletal Innovations LLC's

(56) References Cited

OTHER PUBLICATIONS

Proposed Interpretations of Disputed Claim Terms;" With Exhibits; Case No. 6:12-cv-01379; M.D. Florida; Nov. 1, 2013; 35 pages.
*Bonutti Skeletal Innovations LLC v. Arthrex*; "Defendant Arthrex Inc.'s Preliminary Identification of Proposed Claim Terms for Construction by the Court;" Case No. 6:12-cv-01380; M.D. Florida; Mar. 15, 2013; 8 pages.
*Bonutti Skeletal Innovations LLC v. Arthrex*; "Defendant Arthrex Inc.'s Preliminary Identification of Proposed Claim Terms for Construction by the Court;" Case No. 6:13-cv-00620; M.D. Florida; Oct. 16, 2013; 8 pages.
*Bonutti Skeletal Innovations LLC v. Arthrex*; "Defendant Arthrex, Inc.'s Disclosure of Preliminary Non-Infringement and Invalidity Contentions;" With Exhibits; Case No. 6:13-cv-00620; M.D. Florida; Sep. 23, 2013; 1751 pages.
*Bonutti Skeletal Innovations LLC v. Arthrex*; "Defendant Arthrex, Inc.'s Notice of a First Supplemental Disclosure of Preliminary Invalidity Contentions;" With Exhibits; Case No. 6:13-cv-00620; M.D. Florida; Oct. 24, 2013; 660 pages.
*Bonutti Skeletal Innovations LLC v. Arthrex*; "Defendant Arthrex, Inc.'s Preliminary Constructions of Terms Proposed for Construction by the Court;" Case No. 6:13-cv-01380; M.D. Florida; Mar. 25, 2013; 11 pages.
*Bonutti Skeletal Innovations LLC v. Arthrex*; "Defendant Arthrex, Inc.'s Preliminary Constructions of Terms Proposed for Construction by the Court;" With Exhibit; Case No. 6:12-cv-00620; M.D. Florida; Nov. 1, 2013; 27 pages.
*Bonutti Skeletal Innovations LLC v. Arthrex*; "Defendant Arthrex, Inc.'s Supplemental Claim Construction Statement;" Case No. 6:13-cv-00620; M.D. Florida; Nov. 15, 2013; 9 pages.
*Bonutti Skeletal Innovations LLC v. Arthrex*; "First Amended Complaint with Exhibits" Case No. 6:12-cv-01380; M.D. Florida; Sep. 21, 2012; 259 pages.
*Bonutti Skeletal Innovations LLC v. Arthrex*; "Joint Claim Construction Statement;" Case No. 6:13-cv-00620; M.D. Florida; Nov. 15, 2013; 25 pages.
*Bonutti Skeletal Innovations LLC v. Arthrex*; "Consent Joint Motion for Leave to File Corrected Joint Claim Construction Statement Exhibit;" Case No. 6:13-cv-00620; M.D. Florida; Dec. 12, 2013; 23 pages.
*Bonutti Skeletal Innovations LLC v. Arthrex*; "Notice of Filing Corrected Joint Claim Construction Statement;" Case No. 6:13-cv-00620; M.D. Florida; Dec. 23, 2013; 21 pages.
*Bonutti Skeletal Innovations LLC v. Arthrex*; "Plaintiff Bonutti Skeletal Innovations LLC's Proposed Interpretations of Disputed Claim Terms;" With Exhibits; Case No. 6:13-cv-00620; M.D. Florida; Nov. 1, 2013; 34 pages.
*Bonutti Skeletal Innovations LLC v. Arthrex*; "Plaintiffs Initial Preliminary Identification of Claim Terms and Phrases Potentially Needing Interpretation by the Court;" Case No. 6:13-cv-01380; M.D. Florida; Mar. 15, 2013; 5 pages.
*Bonutti Skeletal Innovations LLC v. DePuy Mitek LLC, et al.*; "Declaration of Stephen M. Belkoff, Ph.D in Support of Plaintiff Bonutti Skeletal Innovations LLC's Preliminary Claim Construction Brief;" Civil Action No. 1:12-cv-11667; United States District Court District of Massachusetts; Dec. 9, 2013; 49 pages.
*Bonutti Skeletal Innovations LLC v. DePuy Mitek LLC, et al.*; "Defendants' List of Proposed Claim Terms and Phrases for Interpretation;" Civil Action No. 1:12-cv-11667; United States District Court District of Massachusetts; Oct. 3, 2013; 6 pages.
*Bonutti Skeletal Innovations LLC v. DePuy Mitek LLC, et al.*; "Defendants' Preliminary Invalidity Disclosures;" Civil Action No. 1:12-cv-11667; United States District Court District of Massachusetts; Aug. 29, 2013; 73 pages.
*Bonutti Skeletal Innovations LLC v. DePuy Mitek LLC, et al.*; "Defendants' Preliminary Non-Infringement Disclosures;" Civil Action No. 1:12-cv-11667; United States District Court District of Massachusetts; Aug. 29, 2013; 86 pages.
*Bonutti Skeletal Innovations LLC v. DePuy Mitek LLC, et al.*; "Defendants' Proposed Claim Constructions;" Civil Action No. 1:12-cv-11667; United States District Court District of Massachusetts; Oct. 10, 2013; 7 pages.
*Bonutti Skeletal Innovations LLC v. DePuy Mitek LLC, et al.*; "Depuy's Opening Claim Construction Brief;" Civil Action No. 1:12-cv-11667; United States District Court District of Massachusetts; Dec. 9, 2013; 35 pages.
*Bonutti Skeletal Innovations LLC v. DePuy Mitek LLC, et al.*; "Joint Appendices a through I;" Civil Action No. 1:12-cv-11667; United States District Court District of Massachusetts; Dec. 9, 2013; 413 pages.
*Bonutti Skeletal Innovations LLC v. DePuy Mitek LLC, et al.*; "Plaintiff Bonutti Skeletal Innovations LLC's Claim Construction Reply Brief;" Civil Action No. 1:12-cv-11667; United States District Court District of Massachusetts; Jan. 16, 2014; 24 pages.
*Bonutti Skeletal Innovations LLC v. DePuy Mitek LLC, et al.*; "Plaintiff Bonutti Skeletal Innovations LLC's List of Proposed Claim Terms and Phrases for Interpretation;" Civil Action No. 1:12-cv-11667; United States District Court District of Massachusetts; Oct. 3, 2013; 4 pages.
*Bonutti Skeletal Innovations LLC v. DePuy Mitek LLC, et al.*; "Plaintiff Bonutti Skeletal Innovations LLC's Preliminary Claim Construction Brief;" Civil Action No. 1:12-cv-11667; United States District Court District of Massachusetts; Dec. 9, 2013; 27 pages.
*Bonutti Skeletal Innovations LLC v. DePuy Mitek LLC, et al.*; "Plaintiff Bonutti Skeletal Innovations LLC's Response to Defendants' Proposed Claim Constructions;" Civil Action No. 1:12-cv-11667; United States District Court District of Massachusetts; Oct. 30, 2013; 14 pages.
*Bonutti Skeletal Innovations LLC v. DePuy Mitek LLC, et al.*; "Plaintiff's Initial Preliminary Infringement Disclosures;" Civil Action No. 1:12-cv-11667; United States District Court District of Massachusetts; May 30, 2013; 8 pages.
*Bonutti Skeletal Innovations LLC v. DePuy Mitek LLC, et al.*; "DePuy's Reply Claim Construction Brief;" Civil Action No. 1:12-cv-11667; United States District Court District of Massachusetts; Jan. 16, 2014; 23 pages.
510k Summary of Safety and Effectiveness; "Mitek Micro Anchor;" Jun. 28, 1996; K962511; 1 page.
510(k) Summary of Safety and Effectiveness; "Multitak Suture System;" Oct. 28, 1996; K964324; 2 pages.
Amis, Andrew A.; "Anterior Cruciate Ligament Graft Positioning, Tensioning, and Twisting;" Knee Surgery, Sports Traumatology, Arthroscopy, 6 [Suppl. 1]; 1998; pp. S2-S12.
Amis, Andrew A.; "Anterior Cruciate Ligament Replacement, Knee Stability and the Effects of Implants;" The Journal of Bone and Joint Surgery, 71-B; 1989; pp. 819-824.
Andersen, Henrik Norholm, et al.; "The Immediate Postoperative Kinematic State After Anterior Cruciate Ligament Reconstruction with Increasing Peroperative Tension;" Knee Surger, Sports Traumatology, Arthroscopy, 6[Suppl. 1]; 1998; pp. S62-S69.
Barber, F. Alan, et al.; "Suture Anchor Failure Strength—An In Vivo Study;" Arthroscopy: The Journal of Arthroscopic and Related Surgery, vol. 9, No. 6; 1993; pp. 647-652.
Barber, F. Alan; "The Ultimate Strength of Suture Anchors;" Arthroscopy: The Journal of Arthroscopic and Related Surgery, vol. 11, No. 1; Feb. 1995, pp. 21-28.
Barrett, Gene R., et al.; "T-Fix Endoscopic Meniscal Repair: Technique and Approach to Different Types of Tears;" Arthroscopy, vol. 11, No. 2; pp. 245-251.
Barrows, Thomas H., et al.; "Synthetic Bioabsorbable Polymers;" High Performance Biomaterials: A Comprehensive Guide to Medical and Pharmaceutical Applications 243 (Michael Szycher ed.); 1991.
Branson, Polymers: Characteristics and Compatibility for Ultrasonic Assembly, Applied Technologies Group, 1971, 4 pages.
Bylski-Austrow, D.I., et al.; "Anterior Cruciate Ligament Replacements: A Mechanical Study of Femoral Attachment Location, Flexion Angle at Tensioning, and Initial Tension;" Journal of Orthopaedic Research, 8; 1990; pp. 522-531.
Canadian Patent Application #2641580 equivalent to U.S. Appl. No. 11/671,556, P. Bonutti, Aug. 6, 2008.

(56) References Cited

OTHER PUBLICATIONS

Canadian Patent Application #2680827 equivalent to U.S. Appl. No. 11/689,670, P. Bonutti, Sep. 22, 2009.
Canadian Patent Application #2698057 equivalent to U.S. Appl. No. 12/202,210, P. Bonutti, Aug. 26, 2010.
Diduch, et al.; "Modern Concepts in Arthroscopic Bankart Repair;" Journal of Long Term Effects of Medical Implants, 9(2&3); 1999; pp. 377-393.
Escalas, F., et al.; "T-Fix Anchor Sutures for Arthroscopic Meniscal Repair;" Knee Surgery, Sports Traumatol, Arthroscopy; 1997, vol. 5, pp. 72-76.
Flory, Principles of Polymer Chemisty, 1953, selected pages (cited in IPR 2013-00603, exhibit 1012).
Gao et al., Swelling of Hydroxypropyl Methycellulose Matrix Tablets . . . , J. of Pharmaceutical Sciences, vol. 85, No. 7, Jul. 1996, p. 732-740.
Gopferich, Mechanisms of polymer degradation and erosion, Biomaterials, 1996, vol. 17, No. 2, p. 103-114.
Grizzi; "Hydrolytic degradation of devices based on poly(DL-lactic acid) size-dependence;" Biomaterials, 1995, vol. 16, No. 4; pp. 305-311.
Grumbine, et al.; "Grappling Suture Fixation Technique;" Clin Podiatr Med Surg. 3(2); 1986; pp. 235-239.
Hanna, et al.; "Repair of Distal Tendo Achillis Rupture With The Use Of The Mitek Anchor System;" J Am Podiatr Med Assoc, 83(12); Dec. 1993; pp. 663-668.
Hecker, Aaron T., et al.; "Pull-out strength of suture anchors for rotator cuff and Bankart lesion repairs;" The American Journal of Sports Medicine, vol. 21, No. 6; Nov.-Dec. 1993; cover page and pp. 874-879.
ISR—International Search Report, WO/2009/029908, published Oct. 28, 2008 for PCT/US2008/074941.
Karlsson, J. et al; "Repair of Bankart Lesions With a Suture Anchor in Recurrent Dislocation of the Shoulder;" Scand. J. of Med & Science in Sports, 1995, 5; pp. 170-174.
Kurosaka, Masahiro, et al.; "A Biomechanical Comparison of Different Surgical Techniques of Graft Fixation in Anterior Cruciate Ligament Reconstruction;" The American Journal of Sports Medicine, vol. 15, No. 3; 1987; pp. 225-229.
Lambert, Kenneth L.; "Vascularized Patellar Tendon Graft with Rigid Internal Fixation for Anterior Cruciate Ligament Insufficiency;" Clinical Orthopaedics and Related Research, No. 172; Jan.-Feb. 1983; pp. 85-89.
Linvatec, Impact Suture Anchor brochure, 2004 (cited in IPR 2013-00628, exhibit 1010).
Markolf, Keith L., et al.; "Biomechanical Consequences of Replacement of the Anterior Cruciate Ligament with a Patellar Ligament Allograft;" The Journal of Bone and Joint Surgery, vol. 78-A, No. 11; Nov. 1996; pp. 1720-1727.
Ming Li; Structure-Property Relationships in the Case of the Degradation of Massive Aliphatic Poly-(α-Hydroxy Acids) in Aqueous Media (Parts 1-3) Journals of Materials Science: Materials in Medicine 1; 1990; pp. 123-139 and 198-206.
Mosca, Vincent S., et al.; "Calcaneal Lengthening for Valgus Deformity of the Hindfoot: Results in Children Who Had Severe, Symptomatic Flatfoot and Skewfoot;" J Bone Joint Surg, vol. 77-A, No. 4; Apr. 1995; pp. 500-512.
Nabors, Erric D., et al.; "Anterior Cruciate Ligament Graft Tensioning in Full Extension;" The American Journal of Sports Medicine, vol. 23, No. 4; 1995; pp. 488-492.
Nativ, O., et al.; "Bladder Neck Suspension Using Bone Anchors For The Treatment of Female Stress Incontinence;" ASAIO J., 43(3); May-Jun. 1997; pp. 204-208.

Obrist, J. et al.; "Bankart Operation With the Mitek Anchor System;" Unfallchirurgie, 17(4); Aug. 1991; pp. 208-212.
Pol E. Huijsmans, et al., "Arthroscopic Rotator Cuff Repair with Double Row Fixation," The Journal of Bone and Joint Surgery, Jun. 2007, vol. 89-A, No. 6, pp. 1248-57.
Richmond, John C., et al.; "Modification of the Bankart Reconstruction with a Suture Anchor;" Am J Sports Med, vol. 19, No. 4; 1991; p. 343-346.
Rodgers, et al.; "The Use of Osseous Suture Anchors in the Treatment of Severe, Complicated Elbow Dislocations;" Am J. Orthrop, 25(11); Nov. 1996; pp. 794-798.
Seitz, William, et al., Repair of the Tibiofibular Syndesmosis with a Flexible Implant, J. of Orthopaedic Trama, vol. 5, No. 1, p. 78-82, 1991.
Shelton, W., et al.; "Meniscus Replacement with Bone Anchors: A Surgical Technique;" Arthroscopy: The Journal of Arcioscopic and Related Surgery, 10(3); Jun. 1994; pp. 324-327.
Snyder, SJ; "Evaluation and Treatment of the Rotator Cuff;" Orthop Clin North Am, 24(1); Jan. 1993; pp. 173-192.
Steiner, Mark E., et al.; "Anterior Cruciate Ligament Graft Fixation;" The American Journal of Sports Medicine, vol. 22, No. 2; 1994; pp. 240-247.
Suchenski, Maureen, et al.; "Material Properties and Composition of Soft-Tissue Fixation;" 26 Arthroscopy: The Journal of Arthroscopy and Related Surgery 822, vol. 26, No. 6; 2010, pp. 821-831.
Tohyama, Harukazu, et al.; "Significance of Graft Tension in Anterior Cruciate Ligament Reconstruction;" Knee Surgery, Sports Traumatology, Arthroscopy, 6 [Suppl. 1]; 1998; pp. S30-S37.
Verhaven, E., et al.; "Surgical Treatment of Acute Biceps Tendon Ruptures With a Suture Anchor;" Acta Orthop Belg, 59(4); 1993; pp. 426-429.
Van Heerwaarden, R.J., et al.; "Effect of Pretension in Reconstructions of the Anterior Cruciate Ligament With a Dacron Prosthesis;" Knee Surgery, Sports Traumatology, Arthroscopy, 3; 1996; pp. 202-208.
Van Kampen, Albert, et al.; "The Effect of Different Graft Tensioning in Anterior Cruciate Ligament Reconstruction: A Prospective Randomized Study;" The Journal of Arthroscopy and Related Surgery, vol. 14, No. 8; Nov.-Dec. 1998; 1998; pp. 845-850.
Weinraub, et al.; "A New Method for Reattachment of the Tendo Achillis Following Retrocalcaneal Exostectomy;" J Foot Ankle Surg, 37(2); Mar.-Apr. 1998; pp. 86-95.
Westrich, et al.; "Isolated Rupture and Repair of the Popliteus Tendon;" Arthoscopy, 11(5); Oct. 1995; pp. 628-632.
Yamamoto, Yuhei, et al.; "Application of a Suture Anchor Technique for Flap Fixation to Bone;" Journal of Reconstructive Microsurgery; Jul. 1996, vol. 12, No. 5, pp. 313-315.
Yoshiya, Shinichi, et al.; "Graft Tension in Anterior Cruciate Ligament Reconstruction;" The American Journal of Sports Medicine, vol. 15, No. 5; 1987, pp. 464-470.
*Bonutti Skeletal Innovations LLC* v. *Linvatec Corporation* and *ConMed Corporation*; "Order;" Case No. 6:12-cv-1379-Orl-22TBS; M.D. Florida; Mar. 25, 2014; 22 pages.
*Bonutti Skeletal Innovation LLC* v. *Arthrex, Inc.*, "Order," Case No. 6:13-cv-620-Orl-22TBS; M.D. Florida, Mar. 25, 2014, 29 pages.
Copending U.S. Appl. No. 11/230,020, Final Office Action dated Aug. 2, 2011.
Copending U.S. Appl. No. 12/030,728, Response to Office Action Sep. 21, 2011.
*Bonutti Skeletal Innovations LLC* v. *DePuy Mitek LLC, et al.*; "Memorandum and Order on Claim Construction;" Civil Action No. 1:12-cv-11667; United States District Court District of Massachusetts; May 2, 2014; 22 pages.
U.S. Appl. No. 14/282,908, May 2014, Bonutti.

\* cited by examiner

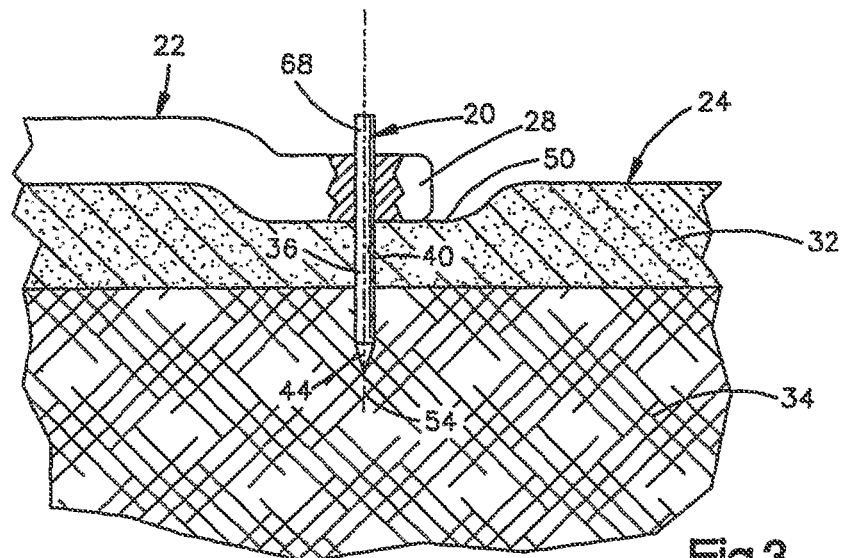
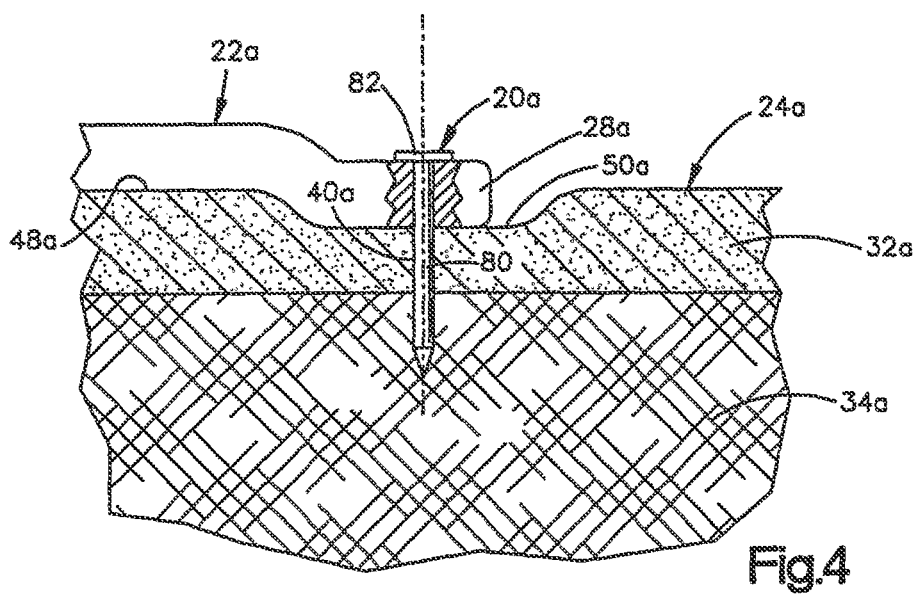

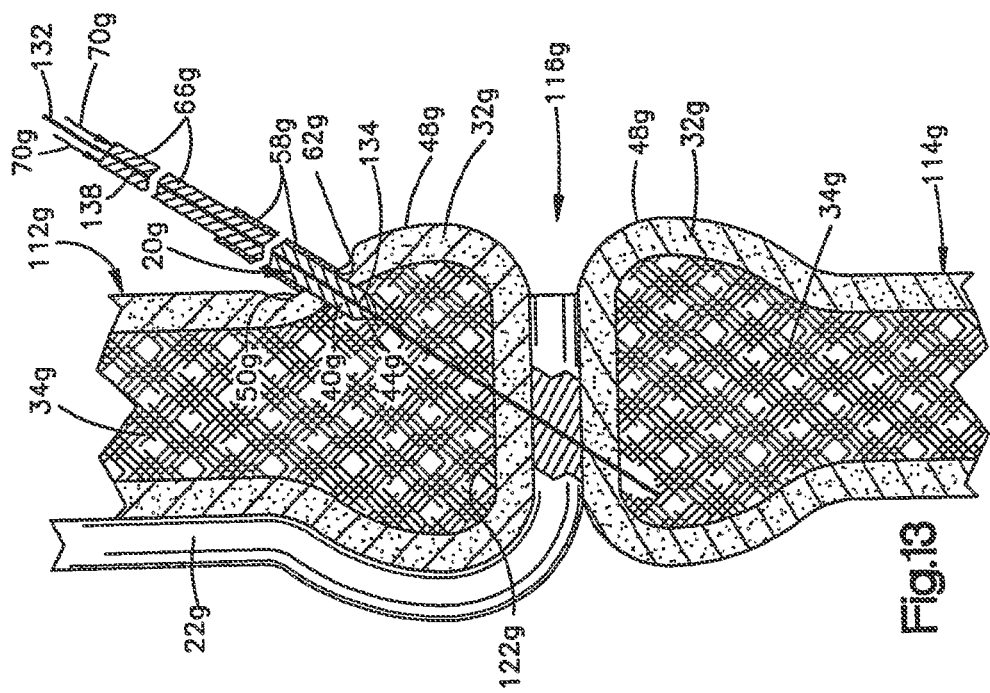
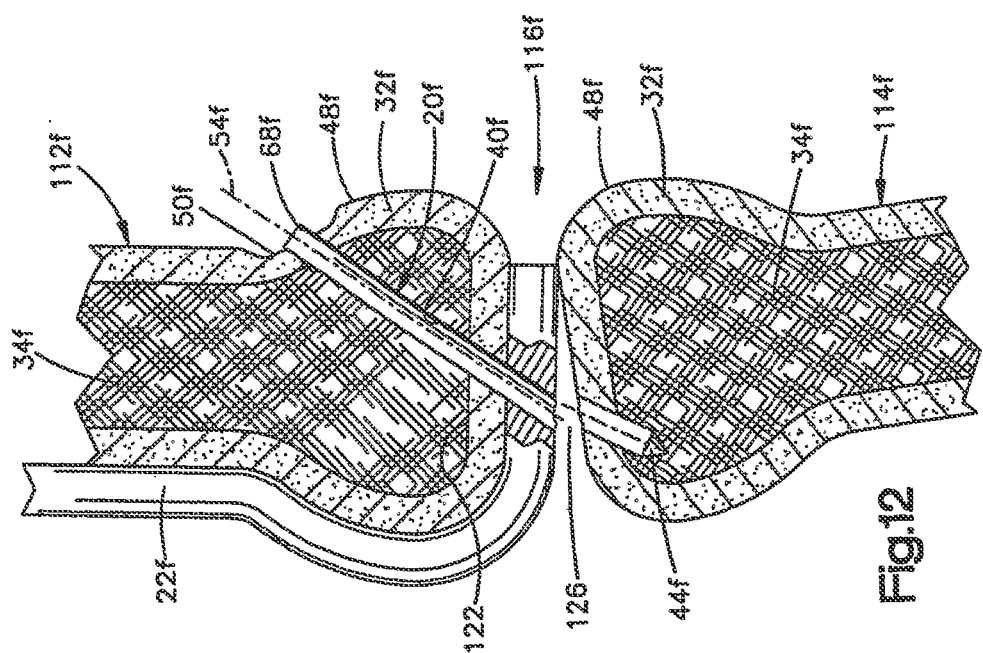

METHOD OF SECURING TISSUE

CROSS REFERENCE TO RELATED APPLICATIONS

This application is a continuation of U.S. patent application Ser. No. 11/067,911 filed Feb. 28, 2005 (now U.S. Pat. No. 8,128,669), which in turn is a continuation of U.S. patent application Ser. No. 10/007,360 filed Oct. 29, 2001 (now U.S. Pat. No. 6,860,885), which in turn is a continuation of U.S. patent application Ser. No. 09/370,865 filed Aug. 9, 1999 (now U.S. Pat. No. 6,447,516). The benefit of the earlier filing dates of each of the above-identified applications is hereby claimed. Furthermore, the content of each of the above-identified applications is incorporated herein by reference.

BACKGROUND OF THE INVENTION

The present invention relates to a new and improved method of securing tissue against movement relative to a portion of a bone in a patient's body.

Various tissue fixation systems have previously been utilized to hold portions of body tissue against movement relative to each other. When tissue is secured against movement relative to a portion of a bone, it is necessary to interconnect the bone and the tissue. In this situation, it has been a common practice to drill a hole which extends into or through the bone. A retaining member such as a pin, screw or suture anchor is positioned in the hole after it has been drilled in the bone. The concept of utilizing a retainer member formed of bone to anchor a suture is disclosed in U.S. Pat. No. 5,626,612.

SUMMARY OF THE INVENTION

The present invention relates to a new and improved method of securing tissue against movement relative to a portion of a bone in a patient's body. The method includes positioning a retainer member formed of bone in the portion of the bone in the patient's body and connecting the retainer member with the tissue to be secured. The step of positioning the retainer member formed of bone in the patient's body may include utilizing the retainer member to form an opening in a compact outer layer of the portion of the bone in the patient's body.

When the retainer member formed of bone is used to form an opening in the portion of the bone in the patient's body, the retainer member may advantageously be at least partially enclosed in a tubular member. Force may be applied against a trailing end portion of the retainer member formed of bone to force a leading end portion of retainer member into the portion of the bone in the patient's body. Movement of the retainer member into the portion of the bone in the patient's body may advantageously be interrupted when the leading end portion of the retainer member has moved to a predetermined depth in the bone in the patient's body.

The retainer member formed of bone may extend through and/or tension body tissue which is to be connected with the bone in the patient's body by the retainer member. The retainer member formed of bone may have a head end portion which engages body tissue. Alternatively, the retainer member formed of bone may be utilized to anchor a suture which is connected with body tissue. The retainer member formed of bone may be positioned in a bone in the patient's body so as to extend across a fracture and hold the portions of the bone on opposite sides of the fracture against movement relative to each other.

A retainer member, which may or may not be formed of bone, is utilized to immobilize a joint by having the retainer member extend between bones at the joint. If it is subsequently desired to release the joint for movement, the retainer member may be broken.

BRIEF DESCRIPTION OF THE DRAWINGS

The foregoing and other features of the invention will become more apparent upon a consideration of the following description taken in connection with the accompanying drawings wherein:

FIG. 3 is a schematic illustration, similar to FIGS. 1 and 2, illustrating the manner in which the tissue is connected with the bone by the retainer member;

FIG. 4 is a schematic illustration, similar to FIG. 3, illustrating the manner in which a second embodiment of the retainer member formed of bone is used to secure tissue against movement relative to a bone in a patient's body;

FIG. 12 is a schematic fragmentary sectional view illustrating the manner in which the retainer member of FIG. 11 is broken to release the joint for movement; and FIG. 13 is a schematic fragmentary sectional view, similar to FIG. 12, illustrating the manner in which a retainer member is moved into bones at a joint to immobilize the joint and hold tissue against movement relative to the joint.

DESCRIPTION OF SPECIFIC PREFERRED EMBODIMENTS OF THE INVENTION

Figure 1:
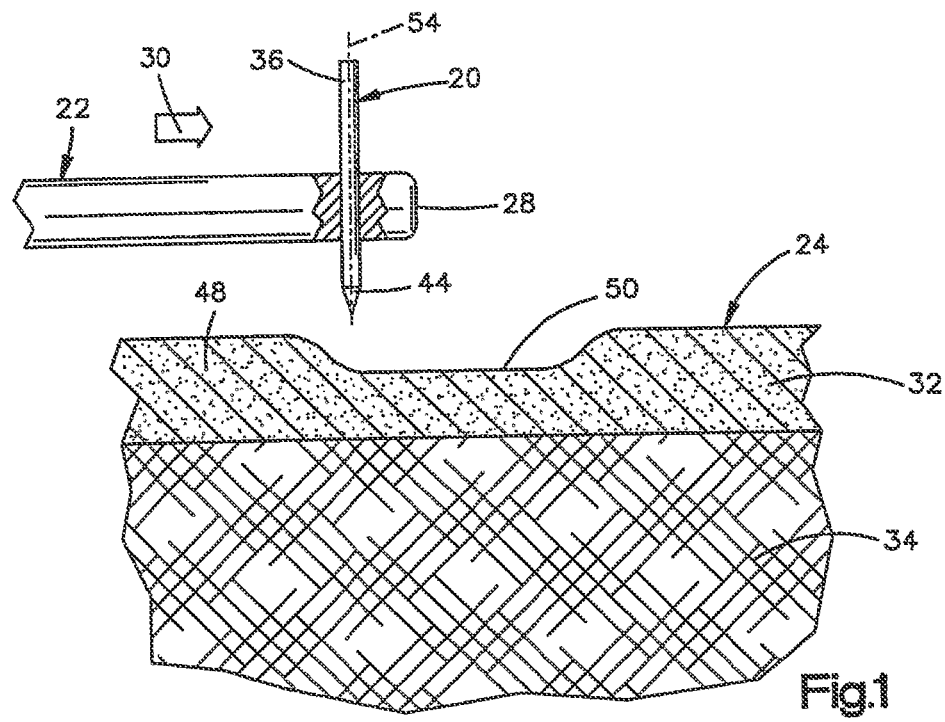
FIG. 1 is a fragmentary schematic sectional view illustrating engagement of a retainer member formed of bone with tissue which is to be tensioned and connected with a bone in a patient's body.
Figure 2:
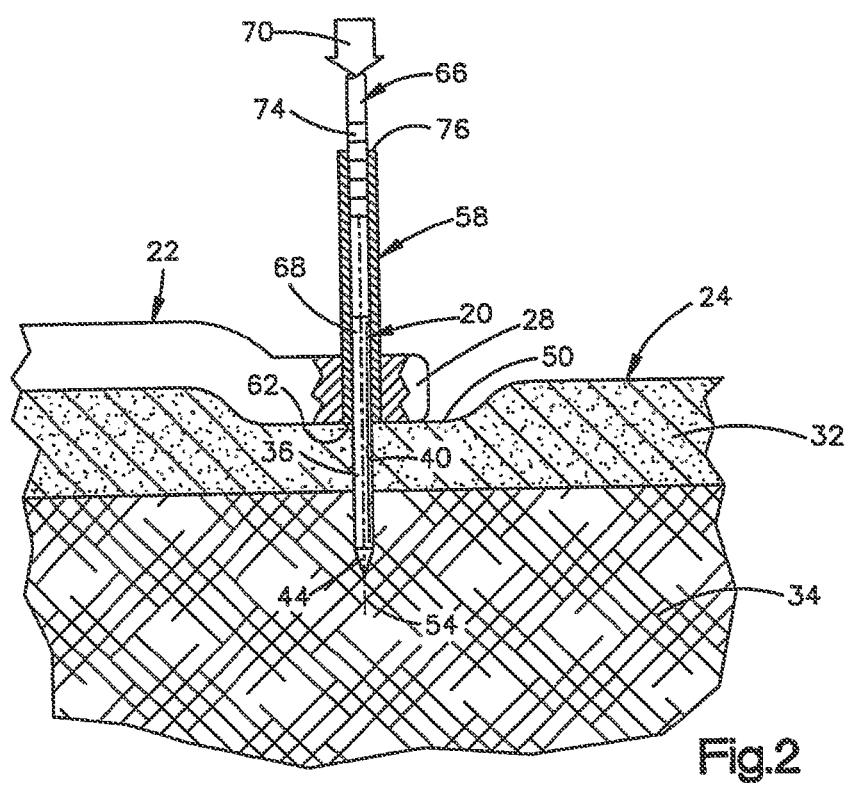
FIG. 2 is a schematic illustration, similar to FIG. 1, illustrating the manner in which the retainer member forms an opening in the bone in the patient's body.

Embodiment of FIGS. 1-3

In the embodiment of the invention illustrated in FIGS. 1-3, a retainer member 20 formed of bone is utilized to hold body tissue 22 against movement relative to a portion of a bone 24 in a human patient's body. The retainer member 20 may formed of bone which is allograft, autograft, or heterograft. However, it is contemplated that it may be preferred to form the retainer member 20 of freeze dried hard cortical bone.

The tissue 22 is connective tissue, such as a ligament or tendon. However, the tissue 22 could be other types of tissue if desired.

When the tissue 22 is to be connected with the bone 24, the retainer member 20 is inserted through an end portion 28 of the tissue 22. The retainer member 20 is then pulled toward the right (as viewed in FIG. 1), in the manner indicated by an arrow 30 in FIG. 1, to tension the tissue 22. The end portion 28 of the tissue 22 is moved rightward from an initial position (FIG. 1) to a connecting position (FIG. 2) as the tissue is tensioned.

The retainer member 20 is then positioned in the bone 24 in the patient's body in the manner illustrated in FIGS. 2 and 3. The retainer member 20 extends through a compact outer or cortical layer 32 of the bone into cancellous bone 34. A cylindrical outer side surface 36 (FIG. 3) on the installed retainer member 20 engages the end portion 28 of the tissue 22, the compact outer layer 32 of the bone 24, and the cancellous bone 34 to maintain tension in the tissue 22 and hold the tissue against movement relative to the bone 24. Although it is preferred to form the retainer member 20 with a cylindrical outer side surface 36, is contemplated that the retainer member 20 could have a different configuration if desired.

In accordance one of the features of the present invention, the retainer member 30 is utilized to form an opening 40 (FIGS. 2 and 3) at a location in the bone 24 where there is no naturally occurring opening (FIG. 1). Although it is preferred to initiate formation of the opening 40 with the retainer member 20 at a location in the bone 24 which is free of openings (FIG. 1), it is contemplated that a small opening could be predrilled through the compact outer layer 32 and into the cancellous bone 34 if desired. This small pilot opening would function to facilitate locating a leading end portion 44 of the retainer member 20 relative to the bone 24.

If a pilot opening is formed in the bone 24, the retainer member 20 would enlarge the pilot opening. As the pilot opening is enlarged by the retainer member 20, the opening 40 in the bone 24 would be formed to a configuration corresponding to the configuration of the outer side surface 36 of the retainer member. For example, if the retainer member 20 has a rectangular outer side surface 36 the opening 40 would be formed to have a rectangular cross-sectional configuration as the retainer member is moved into the pilot opening. Alternatively, if the retainer member 20 has a cylindrical outer side surface 36, the retainer member would form the opening 40 with a cylindrical side surface.

The illustrated retainer member 30 is a solid cylindrical body of hard cortical bone. However, it is contemplated that an axially extending passage could be formed through the retainer member 20. This axially extending passage would accept a long, thin guide member (not shown), such as a K-wire. The guide member, that is, the K-wire, would be utilized to initiate formation of a small opening extending through the compact outer or cortical layer 32 into the cancellous bone 34.

The retainer member 20 would then be moved along the guide member until the leading end portion 44 of the retainer member 20 engages the hard, compact outer layer 32 of the bone 24. The retainer member 20 would then be utilized to form an opening 40 in the compact outer layer 32 of the bone 24 with a cross-sectional configuration corresponding to the cross-sectional configuration of the retainer member. During formation of the opening 40 with the retainer member 20, the retainer member would be moved axially along the guide rod or wire. Once the retainer member 20 has been moved to a desired position relative to the bone 24, the guide wire or rod would be removed from the bone and from the retainer member.

In the embodiment of the invention illustrated in FIGS. 1-3, it is preferred to initiate formation of the opening 40 in the bone 24 with the retainer member 20. Prior to initiation of formation of the opening 40 with the retainer member 20, a hard outer surface 48 is removed from the compact outer layer 32 of bone by a decortication process. The decortication process is performed by abrading the hard outer surface 48 on the compact outer layer 32 of bone to expose an imperforate inner area 50 at a location where the retainer member 20 is to be utilized to form the opening 40 (FIGS. 2 and 3) in the bone 24.

Once the decortication process has been completed, the retainer member 20 is moved through the end portion 28 of the tissue 22 in the manner illustrated schematically in FIG. 1. The retainer member 20 is then pulled toward the right (as viewed in FIG. 1) to obtain a desired level of tension in the tissue 22. This moves the end portion 28 of the tissue 22 from the initial position of FIG. 1 to the connecting position of FIG. 2.

A pointed leading end portion 44 of the retainer member 20 is then moved into engagement with the imperforate inner area 50 on the compact outer layer 32 of bone 24. The retainer member 20 initiates formation of the opening 40. The retainer member 20 is then moved axially through the compact outer layer 32 to the cancellous bone 34 (FIGS. 2 and 3). To move the retainer member 20 through the compact outer layer 32, the retainer member 20 may be rotated about its longitudinal central axis 54 and moved axially into the bone 24 in much the same manner in which a drill is rotated about its central axis and moved into a member being drilled.

It is believed that it will be preferred to move the retainer member 20 into the bone 24 under the influence of an axial force without rotating the retainer member about its central axis 54. Since bone has a relatively high compressive strength, the retainer member 20 formed of bone can be utilized to transmit relatively large forces along the longitudinal central axis 54 of the retainer member 20 to force the retainer member into the bone 24. However, bone has a relatively low tensile strength and cannot transmit large transverse loads. Therefore, when the retainer member 20 is moved into the bone 24 under the influence of axial forces, there may be a tendency for the retainer member to shear or fail by a lateral buckling or fracture of the retainer member rather than by direct compression of the retainer member.

In order to support the retainer member 20 during movement of the retainer member into the bone 24, the retainer member is advantageously inserted into a tubular cylindrical metal sleeve or member 58 (FIG. 2). An annular end portion 62 of the cylindrical sleeve 58 is positioned in engagement with the inner area 50 on the compact outer layer 32 at a location where the retainer member 20 is to be moved into the bone 24. A point on the conical leading end portion 44 of the retainer member engages the inner area 50 on the bone 24 at a location where the formation of the opening 40 is to be initiated.

When the retainer member 20 is to be moved through the tissue 32 into the bone 24, the manner illustrated in FIGS. 1 and 2, the tubular cylindrical sleeve or member 58 is also moved through the end portion 28 of the tissue 22 (FIG. 2). However, if desired, the retainer member 20 could be moved into the bone 24 to the position illustrated in FIG. 3 and the end portion 28 of the tissue then positioned in engagement with the retainer member 20. However, it is believed that it will be preferred to insert the retainer member 20 through the end portion 28 of the tissue 22 before the retainer member is moved into the bone 24 (FIG. 1) so that the retainer member 20 can be utilized to tension the tissue 22.

The tubular member 58 may be moved through the end portion 28 of the tissue 22 (FIG. 2) contemporaneously with the retainer member 20. The conical leading end portion 44 of the retainer member 20 would project from the end of the tubular member 58. This would enable the leading end portion 44 of the retainer member 20 to be utilized to pierce the tissue 22 to initiate the formation of an opening in the tissue. The tubular sleeve 58 can then be utilized to further form the opening in the tissue 22 as the sleeve is moved into the end portion 28 of the tissue. The sleeve 58 may be utilized to apply force to the end portion 28 of the tissue 22 during tensioning of the tissue, that is, during movement of the tissue toward the right (as viewed in FIG. 1).

The retainer member 20 is moved out of the tubular sleeve 58 into the compact outer layer 32 of the bone 24 (FIG. 2). To move the retainer member 20 out of the sleeve 58 into the bone 24, a pusher member 66 is utilized to apply an axial force to a trailing end portion 68 (FIG. 2) of the retainer member 20. The axial force applied by the pusher member 36 has been indicated schematically by an arrow 70 in FIG. 2.

The force 70 applied by the pusher member 66 against the trailing end portion 68 of the retainer member 20 moves the pointed leading end portion 44 of the retainer member 20 into the compact outer layer 32 of the bone 24 and initiates the formation of the opening 40. The tubular sleeve 58 engages the cylindrical outer side surface 36 of the retainer member 20 to support the retainer member against sidewise loading. This results in the retainer member being subjected only to compressive forces as the retainer member is forced into the bone 24.

As the retainer member 20 moves into the bone 24, the material of the compact outer layer 32 of a bone is displaced sideways by the leading end portion 44 of the retainer member. As the retainer member 20 continues to move into the compact outer layer 32 of the bone 24, the material of the compact outer layer supports the retainer member 20 against transverse loading in much the same manner as in which the tubular sleeve 58 supports the retainer member 20. Therefore, the pusher member 68 can apply a relatively large axial force to the retainer member 20 without failure, that is without fracture or buckling, of the retainer member 20. The pusher member 66 has a cylindrical outer side surface with the same diameter as the cylindrical outer side surface 36 of the retainer member 20 and of the passage extending through the tubular sleeve 58.

In accordance with another of the features of the present invention, the retainer member 20 is moved through a predetermined distance into the bone 24. During movement of the retainer member 20 into the bone 24 under the influence of the axial force 70, the extent of movement of the retainer member into the bone 24 is determined. The step of moving the retainer member 20 axially into the bone 24 is interrupted when the leading end portion 44 of the retainer member 20 has moved through the compact outer layer 32 of the bone 24 and has moved a predetermined distance into the cancellous bone 34.

In order to enable the extent of penetration of the retainer member 20 into the bone 24 to be determined during movement of the retainer member into the bone, indicia 74 is provided on the pusher member 66. The indicia 74 cooperates with the tubular sleeve 58 to indicate the extent of movement of the retainer member 20 into the bone 24. When the indicia 74 indicates that the retainer member 20 is moved through a desired distance into the bone 24, the application of the force 70 against the retainer member 20 by the pusher member 66 is interrupted.

In the embodiment of the invention illustrated in FIG. 2, the indicia 74 is provided by a plurality of bands of different color on the pusher member 66. Each of the annular bands on the cylindrical pusher member 66 corresponds to a different extent of movement of the retainer member 20 into the bone 24. When a band of a color corresponding to a desired extent of movement of the retainer member 20 into the bone 24 is aligned with an annular upper end 76 of the tubular sleeve 58, the application of the force 70 to the pusher member is interrupted.

It should be understood that although the indicia 74 has been illustrated in FIG. 2 as being formed by annular bands of different colors, the indicia 74 could be formed by suitable alphanumeric characters if desired. Rather than providing the indicia 74 on the pusher member 66, a stop element could be provided on the pusher member. The stop element would be moved into engagement with a selected one of a plurality of slots which have different lengths and extend axially along the tubular sleeve 58. Of course, other methods of indicating the extent of movement of the retainer member 20 into the bone 24 could be utilized if desired.

Once the retainer member 20 has been moved to the desired position relative to the bone 24, the pusher member 66 is removed from the tubular sleeve 58. The tubular sleeve 58 is removed from the end portion 28 of the tissue 22. This results in the tissue 22 being secured against movement relative to the bone 24 by the retainer member 20 (FIG. 3). Therefore, forces resulting from tension in the tissue 22 are transmitted through the retainer member 20 to the bone 24.

The retainer member 20 is effective to secure the tissue 22 against movement relative to the bone 24 during healing of the tissue. Since the retainer member 20 is formed of bone, the retainer member promotes healing and does not have to be removed after the tissue 22 has healed.

The foregoing description has assumed that the retainer member 20 is inserted through the end portion 28 of the tissue 22 and then moved into the bone 24. However, if desired, the retainer member 20 could be moved into the bone 24 prior to engaging the tissue 22. If this was done, the end portion 28 of the tissue 22 would be pulled to tension the tissue and would then be forced downward, as viewed in FIGS. 2 and 3, onto the exposed trailing end portion 68 of the retainer member 20. If desired, a point could be provided on the trailing end portion 68 of the retainer member 20 to facilitate movement of the retainer member into the end portion 28 of the tissue 22.

Embodiment of FIG. 4

In the embodiment of the invention illustrated in FIGS. 1-3, a cylindrical retainer member 20 is utilized to secure the tissue 22 against movement relative to the bone 24. In the embodiment of the invention illustrated in FIG. 4, a head end portion is provided on the retainer member to clamp the tissue against the bone. Since the embodiment of the invention illustrated in FIG. 4 is generally similar to the embodiment of the invention illustrated in FIGS. 1-3, similar numerals will be utilized to designate similar components, the suffix letter "a" being added to the numerals of FIG. 4 to avoid confusion.

A retainer member 20a (FIG. 4) is formed of bone and is utilized to secure tissue 22a against movement relative to bone 24a in a human patient's body. The retainer member 20a is also utilized to maintain tension in the tissue 22a. The retainer member 20a has a cylindrical shank portion 80 which extends through an end portion 28a of the tissue 22a. The shank portion 80 of the retainer member 20a extends through a compact outer layer 32a of the bone 24a into cancellous bone 34a which is enclosed by the compact outer layer 32a. The shank portion 80 is utilized to form an opening 40a in the bone 24a.

In accordance with a feature of this embodiment of the invention, the retainer 20a has a circular head end portion 82 which projects radially outward from the cylindrical shank portion 80 and is effective to apply force against the end portion 28a of the tissue 22a. Both the head end portion 82 and the shank portion 80 of the retainer member 20a are formed of bone. The head end portion 82 and the shank portion 80 are formed by a single piece of hard cortical bone which has been freeze dried.

The head end portion 82 of the retainer 20a is effective to clamp the end portion 28a of the tissue 22a against an inner area 50a on the compact outer layer 32a of the bone 24a. The inner area 50a is formed by a decortication process during which a portion of a hard outer surface 48a is removed. Removal of the hard outer surface 48a facilitates penetration of the bone 24a by the retainer member 20a.

The end portion 28a of the tissue 22a is engaged by the shank portion 80 of the retainer member 20a, in the same manner as is illustrated in FIG. 1 for the retainer member 20. The tissue 22a is then tensioned by moving the retainer member 20a and the end portion 28a of the tissue toward the right (as viewed in FIG. 4), in the same manner as is schematically illustrated in FIGS. 1 and 2 for the tissue 22. The shank portion 80 of the retainer member 20a is then utilized to form an opening in the bone 24a.

The head end portion 82 of the retainer member 20a is pressed firmly against the end portion 28a of the tissue 22a to hold the tissue in place and maintain a desired tension in the tissue. Although it is preferred to tension the tissue 22 and 22a of FIGS. 1-4 and to maintain the tension in the tissue with the retainer members 20 and 20a, the retainer members could be utilized to hold the tissue in place without tensioning the tissue.

In the embodiment of the invention illustrated in FIG. 4, the shank portion 80 of the retainer member 20a is utilized to initiate formation of the opening 40a at a location which is free of naturally occurring openings. However, a small pilot opening could be provided in the manner previously described in connection with the embodiment of the invention illustrated in FIGS. 1-3. As was previously mentioned, the pilot opening could be formed with a drill or a long thin member, such as a K-wire. If a long thin member is used to form the pilot opening, the retainer member 20a could be provided with an axial passage extending through the shank portion 80 and the head end portion 82. The long thin member would be inserted through the passage in the retainer member 20a and utilized to guide movement of the retainer member into the bone 24a.

Figure 5:
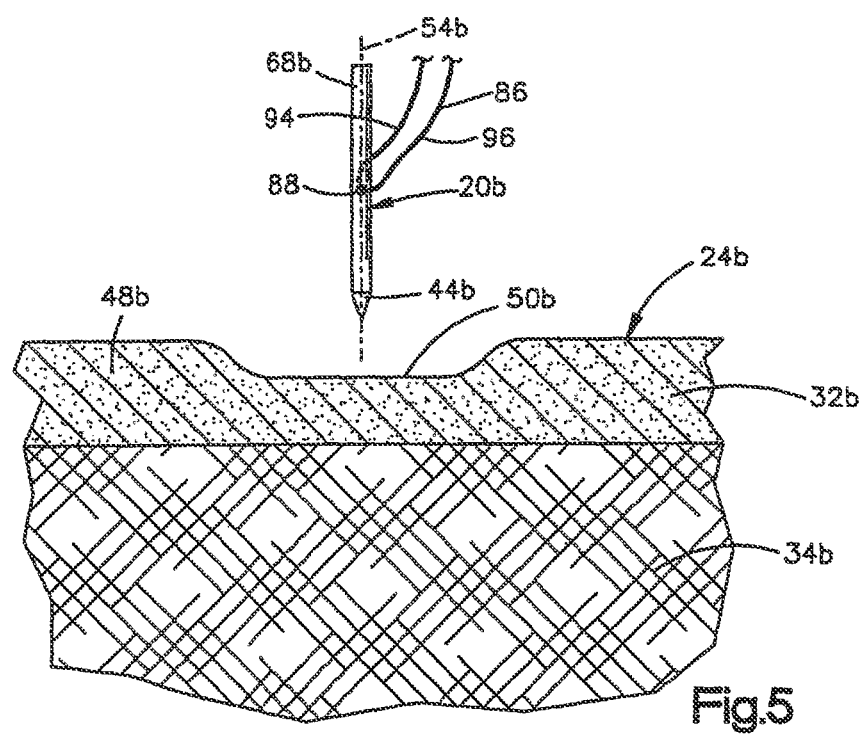
FIG. 5 is a fragmentary schematic illustration, similar to FIG. 1, illustrating the manner in which a retainer member formed of bone is connected with a suture prior to being positioned in a bone in a patient's body.
Figure 6:
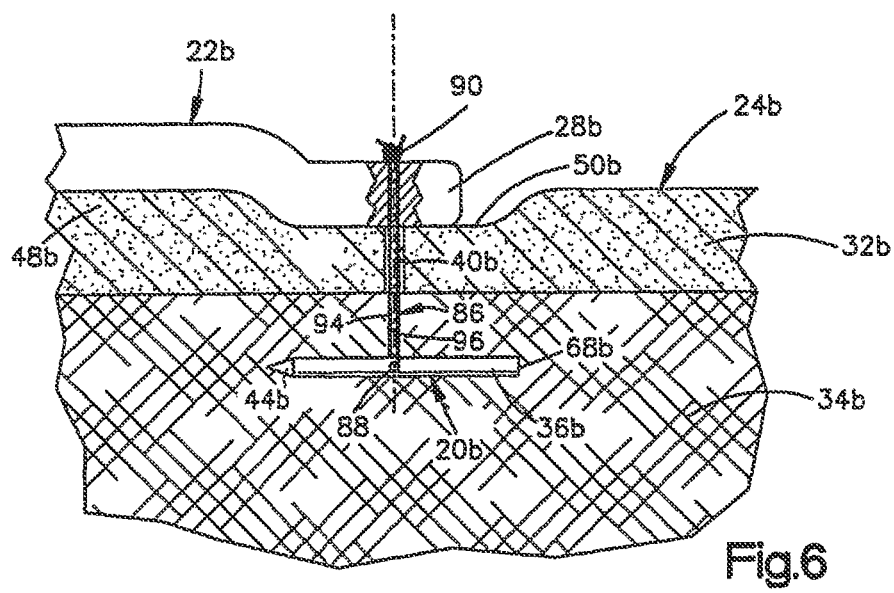
FIG. 6 is a fragmentary schematic illustration, similar to FIG. 5, illustrating the manner in which the retainer member is positioned in the bone in the patient's body and the suture is used to connect tissue with the bone.

Embodiment of FIGS. 5 and 6

In the embodiment of the invention illustrated in FIGS. 1-4, the retainer member 20 formed of bone extends through the tissue 22 to interconnect the retainer member and the bone 24. In the embodiment of the invention illustrated in FIGS. 5 and 6, a retainer member formed of bone is connected with tissue by a suture. Since the embodiment of the invention illustrated in FIGS. 5 and 6 is generally similar to the embodiments of the invention illustrated in FIGS. 1-4, similar numerals will be utilized to designate similar components, the suffix letter "b" being associated with the numerals of FIGS. 5 and 6 to avoid confusion.

A retainer member 20b (FIGS. 5 and 6) is formed of bone. The retainer member 20b may be formed of hard cortical bone which has been freeze dried. The retainer member 20b is utilized to secure tissue 22b (FIG. 6) against movement relative to a bone 24b in a human patient's body.

In accordance with a feature of this embodiment of the invention, a suture 86 is utilized to connect the retainer member 20b with the body tissue 22b. The suture 86 extends through an opening 88 formed in the retainer member 20b. The suture 86 may be connected with the body tissue 22b by a suitable knot 90 (FIG. 6). Alternatively, a fastener or crimp may be utilized to connect end portions of the suture 86. The crimp could have a construction similar to that disclosed in U.S. Pat. No. 5,593,425.

The retainer member 20b is disposed in cancellous bone 34b. The retainer member 20b is supported by the cancellous bone 34b in a spaced apart relationship with a compact outer layer 32b (FIG. 6) of bone which encloses the cancellous bone 34b. Therefore, the cancellous bone 34b is effective to support the retainer member 20b against movement under the influence of force transmitted to the retainer 20b through the suture 86.

The suture 86 extends through an opening 40b formed in the compact outer layer 32b of the bone 24b. The opening 40b was formed in the bone 24b by the retainer member 20b. The suture 86 extends from the opening 40b into engagement with an end portion 28b of the tissue 22b.

The suture 86 may extend through the end portion 28b of the tissue 22b, in much the same manner as in which the retainer 20 of FIG. 3 extends through the end portion 28 of the tissue 22. Alternatively, sections 94 and 96 of the suture 86 could be wrapped around the tissue 22b to secure the tissue against movement relative to the bone 24b. Tension transmitted through the sections 94 and 96 of the suture 86 is applied to the tissue 22b and firmly clamps or presses the tissue against an inner area 50b formed on the compact outer layer 32b by removing a hard outer surface 48b of the bone 24b with a decortication process.

Tension forces transmitted through the sections 94 and 96 of the suture 86 to the retainer member 20b are transmitted from a cylindrical outer side surface 36b of the retainer member 20b to the cancellous bone 34b. The retainer member 20b is completely enclosed by a matrix of the cancellous bone 34b. Therefore, the outer side surface 36b on the retainer member 20b is pressed against only the cancellous bone 34b under the influence of forces transmitted through the suture 86 to the retainer member 20b. The cancellous bone 34b resists these tension forces and supports the retainer member 20b in a spaced apart relationship with the compact outer layer 32b. This results in the retainer member 20b being supported by the cancellous bone 34b.

The retainer 20b is moved into the bone 24b in the same manner as previously explained in conjunction with the embodiment of the invention illustrated in FIGS. 1-3. However, the retainer 22b is moved completely through the compact outer layer 32b of the bone 24b into the cancellous bone 34b. Once this has occurred, the orientation of the retainer member 20b relative to the bone 24b is changed by rotating the anchor 20*b* through ninety degrees (90°) with a toggling action in a manner similar to that disclosed in U.S. Pat. Nos. 5,527,343 and 5,534,012.

To position the retainer member 20*b* relative to the bone 24*b*, the conical leading end portion 44*b* (FIG. 5) on the retainer member 20*b* is moved into engagement with the imperforate inner area 50*b* on the compact outer layer 32*b* of the bone 24*b*. At this time, a central axis 54*b* of the retainer member 20*b* extends perpendicular to the surface 50*b*. An axially directed force, corresponding to the force 70 in FIG. 2, is then applied to the retainer member 20*b*. This force results in the pointed leading end portion 44*b* of the retainer member 20*b* penetrating the compact outer layer 32*b* of the bone 24*b* to initiate formation of the opening 40*b* (FIG. 6).

Continued application of the axial force to the retainer member 20*b* results in the opening 40*b* being formed in the compact outer layer 32*b* of the bone 24*b*. If desired, a pilot opening could be formed in the compact outer layer 32*b* of the bone 24*b* to facilitate locating of the retainer member 20*b* relative to the bone 24*b*. The retainer member 20*b* would then be utilized to enlarge the pilot opening and form the opening 40*b* as the retainer member 20*b* is moved axially through the compact outer layer 32*b* of the bone 24*b*.

The retainer member 20*b* is moved completely through the compact outer layer 32*b* of the bone 24*b* with the retainer member in the orientation illustrated in FIG. 5, that is, with the central axis 54*b* of the retainer member extending perpendicular to the inner area 50*b* on the compact outer layer 32*b*. Once the retainer member 20*b* has been moved completely through the compact outer layer 32*b*, the sections 94 and 96 of the suture 86 are tensioned and the anchor is rotated through 90 to the orientation illustrated in FIG. 6 with a toggling action.

During movement of the retainer member 20*b* through the compact outer layer 32*b* of the bone 24*b* and during formation of the opening 40*b*, it is contemplated that it may be desirable to support the retainer member 20*b* with a tubular sleeve, similar to the tubular sleeve 58 of FIG. 2. If this is done, the suture 86 would extend axially through the tubular sleeve. The pusher member 66 of FIG. 2, could be provided with a central opening through which the suture 86 extends or the suture 86 could extend along an outer side of the pusher member. It is contemplated that the pusher member 66 may be moved axially through the outer layer 32*b* (FIGS. 5 and 6) of the bone 24*b* to apply force against a trailing end portion 68*b* of the retainer member 20*b* during toggling or rotation of the retainer member 20*b* to the orientation illustrated in FIG. 6. The retainer member 20*b* may be moved from the orientation shown in FIG. 5 to the orientation shown in FIG. 6 with a toggling action similar to that disclosed in U.S. Pat. Nos. 5,522,846 and 5,534,012.

In the embodiment of the invention illustrated in FIGS. 5 and 6, the retainer member 20*b* is moved through the compact outer layer 32*b* into the cancellous bone 34*b*. The orientation of the retainer member 20*b* is then changed with a togging action. However, it is contemplated that the retainer 20*b* could be positioned in the bone 24*b* in a different manner if desired. For example, the retainer 20*b* could be positioned in the bone 24*b* in the same manner as previously described in conjunction with the embodiment of the invention illustrated in FIGS. 1-3. If this was done, the trailing end portion 68*b* of the retainer member 20*b* would extend from the bone 24*b* with the axis 54*b* extending perpendicular to the inner area 50*b*.

If the retainer 20*b* is positioned in the manner illustrated in FIGS. 1-3, the suture 86 could extend from a suture opening 88 in the trailing end portion 68*b* of the retainer member 20*b*. This would facilitate moving the suture 86 relative to the retainer member 20*b* when the retainer member is positioned in the bone 24*b*. The trailing end portion 68*b* of the retainer 20*b* would extend outward from the inner area 50*b* on the compact outer layer 32*b* of the bone 24*b*. This would result in the suture opening 88 in the retainer 20*b* being exposed so that the bone 24*b* would not impede movement of the suture 86 relative to the retainer member 20*b*.

Figure 7:
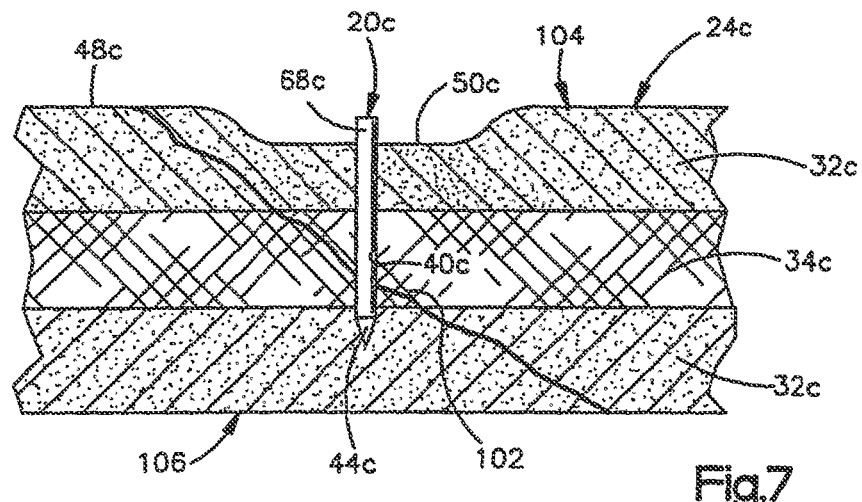
FIG. 7 is a schematic fragmentary sectional view illustrating the manner in which a retainer member formed of bone is used to hold a portion of a bone on one side of a fracture against movement relative to a portion of the bone on the opposite side of the fracture.

Embodiment of FIG. 7

In an embodiment of the invention illustrated in FIGS. 1-6, a retainer member of bone is utilized to position tissue, such as a tendon or ligament, relative to a bone. In the embodiment of the invention illustrated in FIG. 7, a retainer member formed of bone is utilized in the treatment of a fractured bone. Since the embodiment of the invention illustrated in FIG. 7 is generally similar to the embodiment of the invention illustrated in FIGS. 1-6, similar numerals will be utilized to designate similar components, the suffix letter "c" being associated with the numerals of FIG. 7 to avoid confusion.

A bone 24*c* has a fracture 102 which divides the bone 24*c* into a first portion 104 at a second portion 106. The two portions 104 and 106 of the bone 24*c* are formed by a compact outer layer 32*c* which encloses cancellous bone 34*c*. A retainer member 20*c* secures the first and second portions 104 and 106 of the bone 24*c* against movement relative to each other. The retainer member 20*c* is formed of bone. The retainer member 20*c* may be formed of hard cortical bone which has been freeze dried.

The retainer member 20*c* is positioned in the first portion 104 of the bone 24*c*. The retainer member 20*c* extends into the second portion 106 of the bone 24*c* to connect the second portion 106 of the bone 24*c* with the first portion 104 of the bone 24*c*. Thus, the second portion 106 of the bone 24*c* is tissue which is connected with the first portion 104 of the bone 24*c* by the retainer member 20*c*.

The retainer member 20*c* has the same construction as the retainer member 20 of FIGS. 1-3. The retainer member 20*c* is positioned in the bone 24*c* in the same manner as previously explained in conjunction with the embodiment of the invention illustrated in FIGS. 1-3. Thus, the retainer member 20*c* is utilized to form an opening 40*c* in the bone 24*c*. A tubular sleeve, similar to the tubular sleeve 58 of FIG. 2, may be utilized to enclose the retainer member 20*c* during forming of the opening 40*c*.

During positioning of the retainer member 20*c* in the first and second portions 104 and 106 of the bone 24*c*, the retainer member 20*c* is utilized to form an opening 40*c* which extends through the first portion 104 of the bone 24*c* into the second portion 106 of the bone 24*c*. In the embodiment of the invention illustrated in FIG. 7, the opening 40*c* is terminated in the compact outer layer 32*c* of the second portion 106 of the bone 24*c*. However, if desired, the opening 40*c* could extend through both the first portion 104 and the second portion 106 of the bone 24*c*. If this was done, the retainer member 20*c* would be moved downward (as viewed in FIG. 7) so that the leading end portion 44*c* of the retainer member would extend beyond the lower surface of the compact outer layer 32*c* on the portion 106 of the bone 24*c*. The leading end portion 44*c* of the retainer member could then be cut or abraded so that the lower (as viewed in FIG. 7) end of the retainer member 20*c* would be smooth or flush with the lower (as viewed in FIG. 7) surface of the bone 24*c*.

When the retainer member 20*c* is to be positioned relative to the bone 24*c*, a hard outer surface 48*c* on the bone 24*c* is removed with a decortication process. This exposes an imperforate inner area 50*c* on the compact outer layer 32*c* of the bone 24*c*. The retainer member 20*c* is positioned in a tubular sleeve or member having the same construction as the tubular sleeve or member 58 of FIG. 2. An end portion of the tubular member is positioned adjacent to the inner, area 50c with the pointed leading end portion 44c of the retainer member 20c disposed in engagement with the compact outer layer 32c of the bone 24c.

The retainer member 40c is then utilized to form the opening 20c. If desired, a small pilot opening could be formed through the first portion 104 and into the second portion 106 of the bone 24c. The retainer member 20c would then be utilized to form the opening 40c by enlarging the small pilot opening.

To form the opening 40c with the retainer member 20c, a pusher member, corresponding to the pusher member 66 of FIG. 2, is inserted into the tubular sleeve or member, corresponding to the tubular sleeve or member 58 of FIG. 2, in which the retainer member 20c is disposed. Force is then applied against the trailing end portion 68c of the retainer member 20c while the retainer member is supported against sidewise fracturing or buckling by the tubular sleeve.

The leading end portion 44c of the retainer member 20c moves through the compact outer layer 32c on the portion 104 of the bone 24c under the influence of the force applied against the trailing end portion 68c of the retainer member 20c. During the continued application of force to the trailing end portion 68c of the retainer member 20c, the leading end portion 44c of the retainer member moves through the cancellous bone 34c and moves across the fracture 102 into the second portion 206 of the bone 24c. When the leading end portion 44c of the retainer member 20c has moved part way through the compact outer layer 32c on the second portion 106 of the bone 24c to the position illustrated in FIG. 7, the application of force to the trailing end portion 68c of the retainer member 20c is interrupted.

To enable movement of the retainer member 20c into the bone 24c to be interrupted when the retainer member is in the position illustrated in FIG. 7, the extent of movement of the leading end portion 44c of the retainer member 20c relative to the bone 24c is determined during movement of the retainer member 20c into the bone toward the position illustrated in FIG. 7. Determining the extent of movement of the retainer member 20c into the bone 24c may, be accomplished by having indicia on the pusher member cooperate with the tubular sleeve which encloses the retainer member 20c during the application of force to the trailing end portion 68c of the retainer member 20c. The manner in which the indicia on the pusher member cooperates with the tubular sleeve to indicate the extent of movement of the leading end portion 44c of the retainer member 20c is the same as was previously discussed in conjunction with the embodiment of the invention illustrated in FIG. 2.

As was previously mentioned, a different method of indicating the extent of movement of the pusher member relative to the tubular sleeve could be utilized, for example, suitable slots in the tubular sleeve could be engaged by a indicator pin extending from the pusher member. Indicia could be provided on the tubular sleeve adjacent to the slots or the slots could have stop surfaces which limit the extent of movement of the pusher member and, therefore, the extent of movement of the retainer member 20c into the bone 24c.

Figure 8:
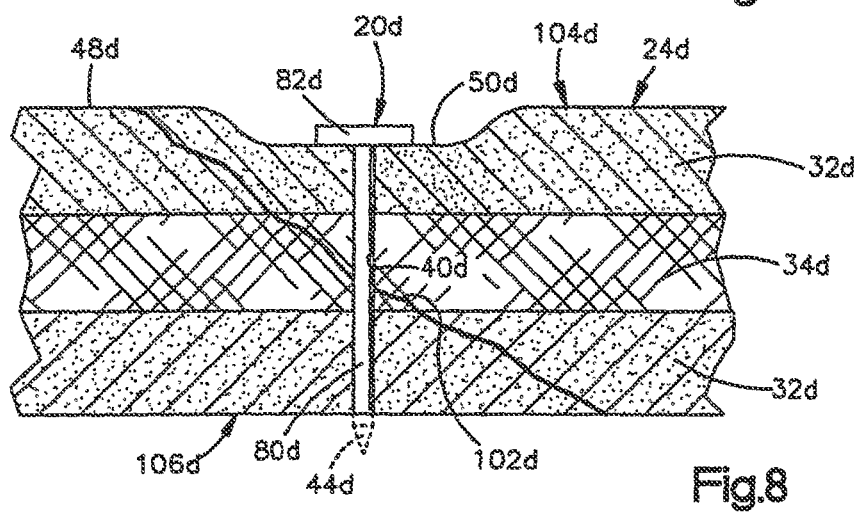
FIG. 8 is a schematic fragmentary sectional view, joined similar to FIG. 7, illustrating the manner in which a second embodiment of the retainer member formed of bone is used to hold a portion of a bone on one side of a fracture against movement relative to a portion of the bone on the opposite side of the fracture.

Embodiment of FIG. 8

The embodiment of the invention illustrated in FIG. 7, a cylindrical retainer member 20c is utilized to treat a fracture 102 in a bone 24c. In the embodiment of the invention illustrated in FIG. 8, the retainer member used to treat the fracture in a bone has a relatively large head end portion. Since the embodiment of the invention illustrated in FIG. 8 is generally similar to the embodiments of the invention illustrated in FIGS. 1-7, similar numerals will utilized to designate similar components, the suffix letter "d" being associated with the numerals of FIG. 8 to avoid confusion.

A retainer member 20d (FIG. 8) is utilized to treat a fracture 102d in a bone 24d. The retainer member 20d has a cylindrical shank portion 80d which extends across the fracture 102d. A circular head end portion 82d is connected with the shank portion 80d. The retainer member 20d is integrally formed as one piece of bone. The retainer member 20d may be formed of hard cortical bone which has been freeze dried.

The fracture 102d divides the bone 24d into a first portion 104d and a second portion 106d. The bone 24d has a compact outer or cortical layer 32d which enclosed cancellous bone 34d. The compact outer layer 32d forms part of the first portion 104d and the second portion 106d of the bone 24d. Similarly, the cancellous bone 34d forms part of both the first and second portions 104d and 106d of the bone 24d.

The fastener 20d is positioned relative to the bone imperforate 24d with the head end portion 82d in engagement with an inner area 50d which, is exposed by removing a portion of a hard outer surface 48d on the compact outer layer 32d. A leading end portion 44d on the shank portion 80d of the retainer member 20d is then positioned in engagement with the inner area 50d of the portion 104d of the bone 24d. An axial force is applied against the head end portion 82d of the fastener 20d to move the leading end portion 44d of the fastener through the portion of the compact outer layer 32d disposed on the first portion 104d of the bone 24d.

As force continues to be applied against the head end portion 82d of the fastener 20d, the leading end portion 44d of the fastener 20d moves into the cancellous bone 34d and across the fracture 102d. Movement of the retainer member 20d into the bone 24d is not interrupted until after the shank portion 80d of the retainer member 24d has moved through the portion of the compact outer layer 32d disposed on the portion 106d of the bone 34d. When the fastener 20d has been moved to the position shown in FIG. 8 with the head end portion 82d firmly pressed against the inner area 50d, the leading end portion 44d of the fastener 20d is removed. This results in the leading end of the shank portion 80d being disposed flush with the outer side surface of the second portion 106d of the bone 24d.

During movement of the retainer member 20d into the bone 24d, the shank portion 80d of the retainer member forms an opening 40d which extends through the first portion 104d of the bone 24d. The opening 40d extends across the fracture 102d and through the second portion 106d of the bone 24d. A small pilot opening extending to the bone 24d may be formed prior to movement of the retainer member 20d into the bone 24d. If this is done, the retainer member 20d applies force to the bone 24d to enlarge the small pilot opening and form the relatively large opening 40d in the bone 24d.

Figure 9:
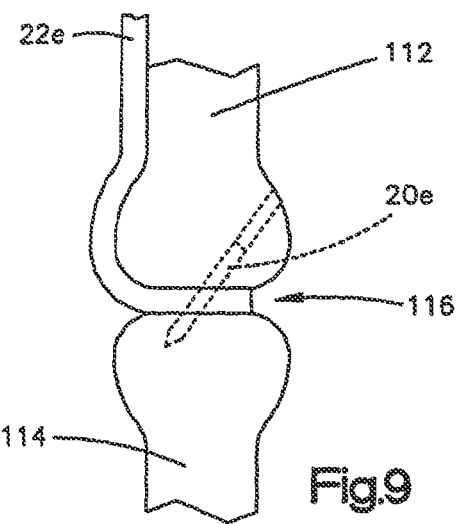
FIG. 9 is a schematic illustration depicting the relationship between end portions of bones in patient's body at a joint between the bones.
Figure 10:
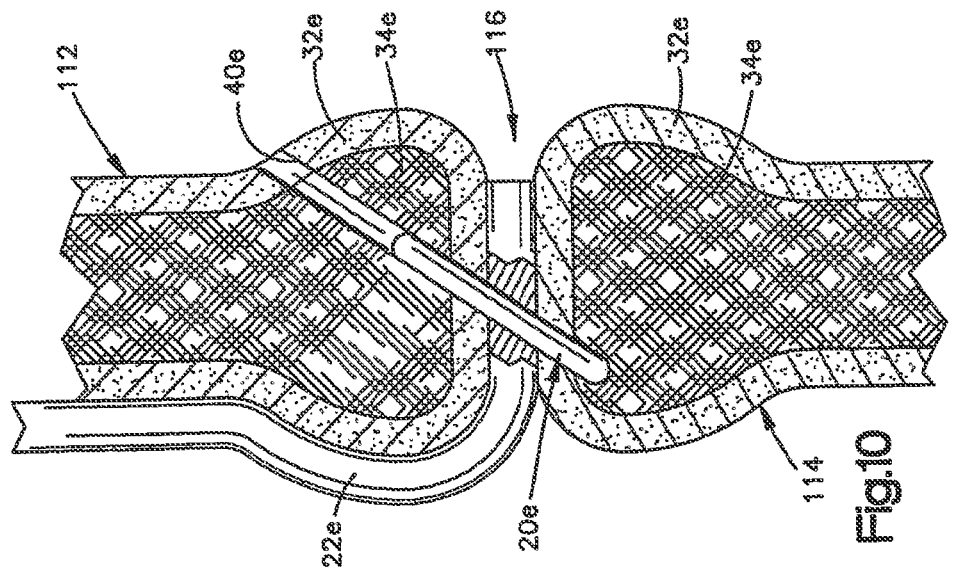
FIG. 10 is an enlarged schematic fragmentary sectional view of the joint of FIG. 9 and illustrating the manner in which a retainer member extends across the joint to immobilize the joint and hold tissue against movement relative to the joint.

Embodiment of FIGS. 9 and 10

In the embodiment of the invention illustrated in FIGS. 1-8, the retainer member has been illustrated as being associated with bone at a location which is spaced at least a short distance from a joint. Of course, the retainer members of FIGS. 1-8 could be associated with bone at a joint if desired. In the embodiment of the invention illustrated. In FIG. 9, a retainer member extends between bones at a joint where the bones are interconnected. Since the embodiment of the invention illustrated in FIGS. 9 and 10 is generally similar to the embodiment of the invention illustrated in FIGS. 1-8, similar numerals will be utilized to designate similar components, the suffix "e" being associated with the numerals of FIGS. 9 and 10 to avoid confusion.

Bones 112 and 114 (FIGS. 9 and 10) are interconnected at a joint 116. Tissue 22e extends along the bone 112 into the joint 116. It is contemplated that the joint 116 may be any one of the many joints in a patient's body.

In accordance with a feature of this embodiment of this invention, a retainer member 20e extends between the bones 112 and 114. The retainer member 20e has a cylindrical configuration. The retainer member 20e is formed from one piece of bone in the same manner as the retainer members 20 of FIGS. 1-8. The retainer member 20e may be formed of hard cortical bone which has been freeze dried. However, the retainer member 20e could be formed of other materials if desired.

The retainer member 20e extends through the tissue 22e to secure the tissue against movement relative to the bones 112 and 114. In addition, the retainer member 20e immobilizes the joint 116. Thus, the retainer member 20e is effective to prevent relative movement between the bones 112 and 114 at the joint 116.

The joint 116 may be permanently immobilized. However, after the tissue 22e has healed, it may be desired to release the bones 112 and 114 for movement relative to each other at the joint 116. This may be accomplished by breaking the retainer member 20e.

To break the bone forming the retainer member 20e, it is merely necessary to move one of the bones, for example the bone 114, relative to the other bone 112. The force transmitted from the bones 112 and 114 to the retainer member 20e will cause the retainer member to break or snap and thereby release the bones 112 and 114 for movement. Since the retainer member 20e is formed of bone, it is not necessary to remove the retainer member from the bones 112 and 114 after the tissue 22e has healed.

The retainer member 20e is positioned in a cylindrical opening 40e which extends through the bone 112 through the tissue 22e and into the bone 114. In the embodiment of the invention illustrated in FIG. 10, the relatively long passage 40e is formed with a drill. However, if desired, the retainer member 20e could be utilized to form the passage 40e in the manner previously described in conjunction with the embodiments of the invention illustrated in FIGS. 1-8.

It is believed, due to the relatively long length of the passage 40e it may be desired to drill a small diameter pilot passage before using the retainer member 20e to form the passage 40e. A pusher member, corresponding to the pusher member 66 of FIG. 2, would move into the passage 40e to apply force against the retainer member 20e which is illustrated as having a length which is shorter than the passage 40e. If desired, the length of the retainer member 20e could be increased so that a trailing end portion of the retainer member 20e would be flush with the entrance to the passage 40e when the leading end portion of the retainer member is in the position illustrated in FIG. 10. Alternatively, the passage 40e could be drilled only through the bone 112. The remainder of the passage would be formed through the tissue 22e and a portion of the bone 114 by the retainer member 20e.

The bones 112 and 114 have compact outer layers 32e which enclose cancellous bone 34e. The retainer member 20e extends from the cancellous bone 34e in the bone 112 through the compact outer layer 32e of the bone 112 into the tissue 22e. The retainer member 20e extends from the tissue 22e through the compact outer layer 32e of the bone 114. The retainer member 20 extends into the cancellous bone 34e of the bone 114.

Since the retainer member 20e extends through the tissue 22e, the retainer member is effective to secure the tissue 22e against movement relative to the bones 112 and 114. Since the retainer member 20e extends between the bones 112 and 114, the retainer member is effective to immobilize the joint 116. Of course, immobilization of the joint can be terminated by merely applying sufficient force to the bones 112 and 114 to break the retainer member 20e at the joint 116.

The retainer member 20e is formed of bone. The illustrated embodiment of the retainer 20e is formed of hard cortical bone which has been freeze dried. However, the retainer 20e could be formed of other materials if desired. For example, the retainer 20e could be formed of biodegradable polymers. Alternatively, the retainer 20e could be formed of a ceramic material.

Figure 11:
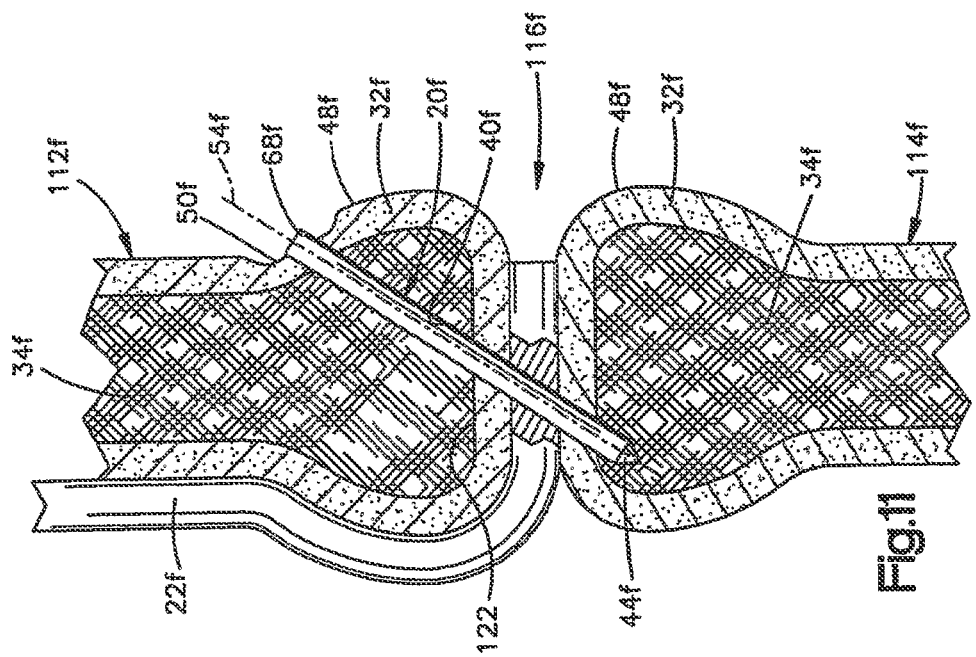
FIG. 11 is a schematic fragmentary sectional view, similar to FIG. 10, illustrating the a manner in which a second embodiment of the retainer member is utilized to immobilize a joint and hold tissue against movement relative to the joint.

Embodiment of FIGS. 11 and 12

In the embodiment of the invention illustrated in FIGS. 9 and 10, a relatively short retainer member 20e extends between bones 112 and 114 to immobilize a joint 116 and to secure tissue 22e against movement relative to the joint. In the embodiment of the invention illustrated in FIGS. 11 and 12, a relatively long retainer member is provided to immobilize the joint and hold tissue against movement relative to the joint. Since the embodiment of the invention illustrated in FIGS. 11 and 12 is generally similar to the embodiment of the invention illustrated in FIGS. 1-10, similar numerals will be utilized to designate similar components, the suffix letter "f" being associated with the numerals of FIGS. 11 and 12.

Bones 112f and 114f are interconnected at a joint 116f. Tissue 22f extends into the joint 116f and is disposed between the ends of the bones 112f and 114f. A retainer member 20f extends between the bones 112f and 114f and extends through the tissue 22f at the joint 116f. The retainer member 20f immobilizes the joint, that is, the retainer member secures the bones 112f and 114f against movement relative to each other. In addition, the retainer 20f secures the tissue 22f against movement relative to the bones 112f and 114f at the joint 116f.

In accordance with one of the features of the present invention, the retainer member 20f is formed of bone. The retainer member 20f may be formed of hard cortical bone which has been freeze dried. The retainer member 20f is utilized to form an opening 40f which extends through the bone 112f, through the tissue 22f, and into the bone 114f. If desired, the retainer member 20f could extend through the bone 114f and have a lower (as viewed in FIG. 11) end which is flush with an outer side surface of the bone. The retainer member 20f has a cylindrical configuration and is integrally formed as one piece of bone.

The retainer member 20f has a pointed leading end portion 44f which initiates formation of the opening 40f. If desired, a relatively small diameter pilot opening could be drilled through the bone 112f, body tissue 22f into the bone 114f. The retainer member 20f would then be utilized to form the opening 40f by enlarging the small pilot opening. In the embodiment of the invention illustrated in FIG. 10, it is contemplated that it may be preferred to form the opening 40e with a drill. However, in the embodiment of the invention illustrated in FIGS. 11 and 12, it is contemplated that it will be preferred to utilize the retainer member 20f to form the opening 40f.

When the retainer member 20f is to be positioned in the bones 112f and 114f, a hard outer surface 48f of a compact outer layer 32f of the bone 112f is ground or abraded away with a decortication process. This exposes an imperforate inner area 50f on the compact outer layer 32f of the bone 112f. The leading end portion 44f of the retainer member 20f is then positioned in engagement with the inner area 50f.

A force, corresponding to the force 70 of FIG. 2, is then applied to a trailing end portion 68f of the retainer member 20f. The retainer member 20f may be enclosed with a tubular member, corresponding to the tubular member 58 of FIG. 2.

Force may be applied against the trailing end portion 68f of the retainer member 20f with a pusher member, corresponding to the pusher member 66 of FIG. 2. The force applied to the trailing end portion 68f of the retainer member 20f extends parallel to a longitudinal central axis 54f of the retainer member 20f.

The force applied to the trailing end portion 68f of the retainer member 20f causes the pointed leading end portion 44f of the retainer member to initiate the formation of the opening 40f in the compact outer layer 32f of the bone 112f. The force applied to the trailing end portion 68f of the retainer member 20f moves the leading end portion 44f of the retainer member through the compact outer layer 32f into cancellous bone 34f which is enclosed by the compact outer layer 32f.

The continued application of force to the trailing end portion 68f of the retainer member 20f moves the retainer member through the cancellous bone 34f. The leading end portion 44f of the retainer member 20f moves into engagement with an inner side surface 122 of the compact outer layer 32f. The pointed leading end portion 44f then penetrates the compact outer layer 32f for a second time. This results in the formation of an opening 40f which extends through the bone 112f.

The leading end portion 44f of the retainer member 20f then enters the tissue 22f. The continued application of force against the trailing end portion 68f of the retainer member 20f moves the leading end portion 44f into the compact outer layer 32f on the bone 114f. If desired, a hard outer surface 48f on the compact outer layer 32f of the bone 114f could be removed with a decortication process at the location where the leading end portion 44f of the retainer member 20f moves into initial engagement with the bone 114f.

The continued application of force against the trailing end portion 68f of the retainer member 20f moves the retainer member through the compact outer layer 32f of the bone 114f into cancellous bone 34f. Movement of the retainer member 20f into the bone 114f can be terminated with the leading end portion 44f in the cancellous bone 34f of the bone 114f, as shown in FIG. 11. However, if desired, the movement of the retainer member 20f along its longitudinal central axis 54f could be continued and the retainer member moved through the compact outer layer 32f of the bone 114f for a second time.

When the retainer member 20f is moved through the bone 112f and the tissue 22f into the bone 114f, a shown in FIG. 11, the retainer member immobilizes the joint 116f. In addition, the retainer member 20f secures the tissue 22f in the joint 116f.

During movement of the retainer member 20f into and through the bone 112f into and through the tissue 22f and into the bone 114f, it is believed that it may be preferred to enclose the portion of the retainer member 20f which is disposed outside of the opening 40f with a tubular sleeve or member, corresponding to the tubular sleeve or member 58 of FIG. 2. The end of the tubular member would be positioned in engagement with the inner area 50f on the compact outer layer 32f of the bone 112f. A pusher member, corresponding to the pusher member 66 of FIG. 2, would be utilized to apply force against the trailing end portion 68f of the retainer member 20f.

It is believed that it would be particularly advantageous to utilize indicia which indicates the extent to which the leading end portion 44f of the retainer member 20f is moved along the central axis 54f. This is because the opening 40f has a relatively long axial extent and the use of indicia, corresponding to the indicia 74 of FIG. 2, on the pushrod will enable a surgeon to determine exactly where the leading end portion 44f of the retainer member 20f is located relative to the bones 112f and 114f. The indicia will also allow the surgeon to terminate movement of the retainer member 20f along the axis 54f when the retainer member is moved to the position shown in FIG. 11.

After the joint 116f has been immobilized for a sufficient period of time to enable the tissue 22f to heal, it is contemplated that it may be desired to release the joint 116f so that the bones 112f and 114f can move relative to each other at the joint. To release the joint 116f, force is applied to the bones 112f and 114f to break the retainer member 20f in the manner illustrated schematically in FIG. 12. Thus, force applied to the bones 112f and 114f tends to rotate the bone 114f in a counterclockwise direction from the position illustrated in FIG. 11 to the position shown in FIG. 12. As this occurs, the force applied to the retainer member 20f causes the retainer member to break or fracture at a location indicated schematically at 126 in FIG. 12. Since the retainer member 20f is formed of bone which is relatively weak in tension, a relatively small amount of force is required to break the retainer member 20f. Since the retainer member 20f is formed of bone, there is no need to remove the retainer member after it has been broken.

Embodiment of FIG. 13

In the embodiment of the invention illustrated in FIGS. 11 and 12, the retainer member 20f is utilized to initiate the formation of the opening 40f and to form the opening. In the embodiment of the invention illustrated in FIG. 13, a guide wire or rod is utilized to initiate formation of the opening which is subsequently formed by the retainer member. Since the embodiment of the invention illustrated in FIG. 13 is generally similar to the embodiment of the invention illustrated in FIGS. 1-12, similar numerals will be utilized to designate similar components, the suffix letter "g" being associated with the numerals of FIG. 13 to avoid confusion.

Tissue 22g (FIG. 13) is disposed between bones 112g and 114g at a joint 116g. A retainer member 20g is utilized to secure the tissue 22g against movement relative to the bones 112g and 114g and to secure the bones against movement relative to each other. The retainer member 20g has a cylindrical configuration and is formed of bone. The retainer member 20g may be formed of hard cortical bone which has been freeze dried.

In accordance with one of the features of the embodiment of the invention illustrated in FIG. 13, a cylindrical guide wire or rod 132 extends through a cylindrical passage 134 formed in the retainer member 20g. The guide wire or rod 132 forms small diameter pilot openings which extend through the bone 112g, through the tissue 22g at the joint 116g and into the bone 114g. The guide wire or rod 132 is moved to the position illustrated in FIG. 13 to form the relatively small diameter pilot openings while the retainer member 20g is spaced apart from the guide wire or rod. To move the guide wire or rod 132 to the position shown in FIG. 13; an axial force is applied against the guide wire.

Once the guide wire 132 has been moved through the bone 112g, the tissue 22g, and into the bone 114g in the manner illustrated in FIG. 13, the retainer member 20g is moved into telescopic engagement with the guide wire 132. To provide for engagement of the guide wire 132 with the retainer member 20g, the upper (as viewed in FIG. 13) end of the guide wire 132 is inserted into the cylindrical passage 134 which extends axially through the retainer member 20g. The retainer member 20g is then moved, axially along the guide wire 132 until a conical leading end portion 44g of the retainer member 20g engages an inner area 50g on the compact outer layer 32g of the bone 112g.

The inner area 50g is formed by abrading or otherwise removing a hard outer surface layer 48g from the compact outer layer 32g with a decortication process.

Once the retainer member 20g has been moved along the guide wire 132g into engagement with the compact outer layer 32g of the bone 112g, a tubular sleeve or member 58g is moved along the guide wire rod 132 into telescopic engagement with the retainer member 20g. An annular leading end portion 62g of the tubular sleeve 58g is moved into engagement with the area 50g in the manner illustrated in FIG. 13. At this time, the leading end portion 44g of the retainer member 20g is also disposed in engagement with the area 50g on the compact outer layer 32g of the bone 12g.

The tubular sleeve 58g has an axial extent which is greater than the axial extent of the retainer member 20g. Therefore, the tubular sleeve 50g extends axially past an upper or trailing end portion of the retainer member 20g. At this time, the retainer member 20g is fully enclosed by the tubular sleeve 58g.

A pusher member 66g has a longitudinally extending cylindrical passage 138 through which the guide wire rod 132 extends. When the leading end portion 44g of the retainer member 20g is disposed in engagement with the inner area 50g, the tubular sleeve 58g encloses the retainer member. The pusher member 66g extends axially upward (as viewed in FIG. 13) from the upper end portion of the tubular sleeve or member 58g.

In order to form the opening 40g with the retainer member 20g, force, indicated schematically by arrows 70g in FIG. 13, is applied against the upper (as viewed in FIG. 13) end of the pusher member 66g. The force is transmitted from the pusher member 66g to the retainer member 20g. The force transmitted to the retainer member 20g causes the leading end portion 44g of the retainer member 20g to form the opening 40g in the compact outer layer 32g of the bone 112g.

As the opening 40g is formed in the compact outer layer 32g of the bone 112g by the retainer member 20g, the retainer member is moved axially along the guide wire 132. Therefore, the guide wire 132 is effective to steer movement of the retainer member 20g through the bone 112g and tissue 22g into the bone 114g. As the force 70g applied by the pusher member 66g to the trailing end of the retainer member 20g moves the retainer member 20g into cancellous bone 34g of the bone 112g, the guide wire 132 cooperates with the retainer member 20g to prevent deviation of the retainer member from its intended course.

Continued movement of the retainer member 20g along the guide wire 132 under the influence of force 70g, results in the leading end portion 44g of the retainer member 20g moving into engagement with an inner side surface 122g of the compact outer layer 32g on the bone 112g. Continued application of axial force to the retainer member 20g moves the retainer member along the guide wire 132 through the compact outer layer 32g and into the tissue 22g. The leading end portion 44g of the retainer member 20g then moves into engagement with the compact outer layer 32g of the bone 114g.

Continued movement of the retainer member 20g along the guide wire 132 moves the leading end portion 44g of the retainer member through the compact outer layer 32g of the bone 114g. The leading end portion 44g of the retainer member 20g then moves into cancellous bone 34g which is enclosed by the compact outer layer 32g of the bone 114g. Indicia, corresponding to the indicia 74 of FIG. 2, on the pusher member 66g cooperates with the tubular sleeve 58g to indicate when the leading end portion 44g of the retainer member 20g has reached the lower (as viewed in FIG. 13) end of the guide wire 132. When this happens, an application of the force 70g to the pusher member 66g is interrupted and axial movement of the retainer member 20g along the guide wire 132 is interrupted. At this time, a trailing end portion of the retainer member 20g will have reached the end of the tubular sleeve 58 and be adjacent to the inner area 50g on the compact outer layer 32g of the bone 112g.

The tubular sleeve 58g and pusher member 66g are then disengaged from the guide wire 132 by moving them axially upward (as viewed in FIG. 13) away from the bone 112g along the guide wire. The guide wire 132 is then withdrawn from the retainer member 20g.

After the guide wire 132 is withdrawn from the retainer member 20g, the retainer member is disposed in the same orientation relative to the bones 112g and 114g as is the retainer member 20f relative to the bones 112f and 114f of FIG. 11. Thus, the retainer member 20g will extend through the bone 112g and through the body tissue 22g into the bone 114g. If desired, the retainer member 20g could be moved through the bone 114g so that the leading end portion 44g of the retainer member 20g extends from the outer side surface of the bone 114g. The leading end portion 44g of the retainer member would then be removed so that the end of the retainer member 20g would be aligned with the outer side surface of the bone 114g to provide a smooth area which would not irritate adjoining tissue. If the retainer member 20g is to extend through the bone 114g, the guide wire 132 would be moved through the bone 114g to enable the guide wire to guide movement of the retainer member 20g throughout the extent of axial movement of the retainer member relative to the bone 114.

Once the retainer member 20g has been moved to the desired position relative to the bones 112g and 114g, that is to a position corresponding to the position of the retainer member 20f of FIG. 11 relative to the bones 112f and 114f, the joint 116g is immobilized. Thus, the bones 112g and 114g are secured against movement relative to each other. In addition, the tissue 22g is secured against movement relative to the bones 112g and 114g.

In the embodiment of the invention illustrated in FIG. 13, the retainer member 20g is formed of bone. However, the retainer member 20g may be formed of other materials if desired. For example, the retainer member 20g could be formed of a biodegradable material. Alternatively, the retainer member 20g could be formed of a ceramic material.

Conclusion

In view of the foregoing description, it is apparent that the present invention relates to a new and improved method of securing tissue 22 against movement relative to a portion of a bone 24 in a patient's body. The method includes positioning a retainer member 20 formed of bone in the portion of the bone 24 in the patient's body and connecting the retainer member with the tissue 22 to be secured. The step of positioning the retainer member 20 formed of bone in the patient's body may include utilizing the retainer member to form an opening 40 in a compact outer layer of the portion of the bone 24 in the patient's body.

When the retainer member 20 formed of bone is used to form an opening 40 in the portion of the bone 24 in the patient's body, the retainer member may advantageously be at least partially enclosed in a tubular member 58. Force 70 may be applied against a trailing end portion 68 of the retainer member 20 formed of bone to force a leading end portion 44 of retainer member into the portion of the bone 24 in the patient's body. Movement of the retainer member 20 into the portion of the bone 24 in the patient's body may advantageously be interrupted when the leading end portion 44 of the retainer member has moved to a predetermined depth in the bone in the patient's body.

The retainer member 20 formed of bone may extend through and/or tension body tissue 22 which is to be connected with the bone 24 in the patient's body by the retainer member. The retainer member 20 formed of bone may have a head end portion 82 which engages body tissue 22. Alternatively, the retainer member 20 formed of bone may be utilized to anchor a suture 86 which is connected with body tissue. The retainer member 20 formed of bone may be positioned in a bone 24 in the patient's body so as to extend across a fracture 102 and hold the portions 104 and 106 of the bone on opposite sides of the fracture against movement relative to each other.

A retainer member 20, which may or may not be formed of bone, is utilized to immobilize a joint 116 by having the retainer member extend between bones 112 and 114 at the joint. If it is subsequently desired to release the joint 116 for movement, the retainer member may be broken.

What is claimed is:

1. A method of securing tissues of a body of a patient, the method comprising:
    drilling a hole through a first tissue portion and a second tissue portion, the hole having a longitudinal axis;
    utilizing an elongate member connected to a first member and a second member;
    passing the first member into the hole and through at least portions of the first tissue portion and the second tissue portion, the elongate member extending through the portions of the first tissue portion and the second tissue portion;
    changing an orientation of at least a portion of the first member to form an angle between a longitudinal axis of the first member and the longitudinal axis of the hole; and
    tensioning the elongate member between the first and second member to resist relative movement between the first tissue portion and the second tissue portion.

2. The method as set forth in claim 1, wherein at least one of the first tissue portion and the second tissue portion includes bone.

3. The method as set forth in claim 2, wherein the bone includes a compact outer layer.

4. The method as set forth in claim 1, further comprising applying a force to the first member.

5. The method as set forth in claim 4, wherein the force includes an axially directed force.

6. The method of claim 1, further comprising, before passing the first member into the hole and through the at least portions of the first tissue portion and the second tissue portion, passing the first member through a tubular member positioned adjacent one of the first tissue portion and the second tissue portion.

7. The method of claim 1, wherein the first member includes a first end and an opposite second end, a length and the longitudinal axis of the first member extending between the first and second ends, and a opening therethrough located between the first end and the second end.

8. The method of claim 7, wherein the elongate member includes a first portion and a second portion, at least one of the first portion and the second portion extending outwardly from the opening in the first member, portions of the first portion and the second portion of the elongate member extending through the first tissue portion and the second tissue portion.

9. A method of securing tissues of a body of a patient, the method comprising:
    drilling a hole through a first tissue portion and a second tissue portion of the body, the hole having a longitudinal axis;
    passing a first member, connected to an elongate member, into the hole and through at least portions of the first tissue portion and the second tissue portion;
    moving the first member from a first portion to a second position, a longitudinal axis of the first member in the first position being aligned with the longitudinal axis of the hole, and the longitudinal axis of the first member being angled relative to the longitudinal axis of the hole in the second position; and
    tensioning the elongate member to resist relative movement between the first tissue portion and the second tissue portion.

10. The method as set forth in claim 9, further comprising utilizing a second member connected to the elongate member.

11. The method as set forth in claim 9, where at least one of the first tissue portion and the second tissue portion is bone including a compact outer layer.

12. The method of claim 9, wherein the first member includes a first end and an opposite second end, a length and the longitudinal axis of the first member extending between the first and second ends, and an opening therethrough located between the first end and the second end.

13. The method of claim 12, wherein the elongate member includes a first portion and a second portion, at least one of the first portion and the second portion extending outwardly from the opening in the first member, portions of the first portion and the second portion of the elongate member extending through the first tissue portion and the second tissue portion.

14. A method of securing tissues of a body of a patient, the method comprising:
    utilizing an elongate member connected to a first member and a second member;
    passing the first member through at least portions of a first tissue portion and a second tissue portion of the body, and at least one of the first tissue portion and the second tissue portion being bone;
    toggling the first member relative to the elongate member from a first position to a second position; and
    tensioning the elongate member between the first and second member to resist relative movement between the first tissue portion and the second tissue portion.

15. The method of claim 14, wherein at least one of the first tissue portion and the second tissue portion is bone.

16. The method of claim 14, wherein the first member includes a first end and an opposite second end, a length and a longitudinal axis extending between the first and second ends, and an opening therethrough located between the first end and the second end, and the elongate member includes a first portion and a second portion, and at least one of the first portion and the second portion extending outwardly from the opening in the first member, portions of the first portion and the second portion of the elongate member extending through the first tissue portion and the second tissue portion.

17. The method of claim 16, wherein toggling the first member comprises rotating the first member such that the longitudinal axis thereof is rotated approximately ninety degrees.

18. A method of securing tissues of a body of a patient, the method comprising:
    utilizing an elongate member connected to a first member;
    positioning a tubular member with respect to one of a first tissue portion and a second tissue portion of the body;
    passing the first member through the tubular member;
    passing the first member through at least portions of the first tissue portion and the second tissue portion, and at least one of the first tissue portion and the second tissue portion being bone;
    toggling the first member relative to the elongate member from a first position to a second position; and tensioning the elongate member to resist relative movement between the first tissue portion and the second tissue portion.

19. The method of claim 18, wherein at least one of the first tissue portion and the second tissue portion is bone.

20. The method of claim 18, wherein the first member includes a first end and an opposite second end, a length and a longitudinal axis extending between the first and second ends, and an opening therethrough located between the first end and the second end, and the elongate member includes a first portion and a second portion, and at least one of the first portion and the second portion extending outwardly from the opening in the first member, portions of the first portion and the second portion of the elongate member extending through the first tissue portion and the second tissue portion.

21. The method of claim 20, wherein toggling the first member comprises rotating the first member such that the longitudinal axis thereof is rotated approximately ninety degrees.

22. A method of securing tissues of a body of a patient, the method comprising:
    utilizing an elongate member connected to a first member and a second member;
    passing the first member through at least portions of a first tissue portion and second tissue portion of the body;
    changing the orientation of the first member relative to the elongate member; and
    tensioning the elongate member to maintain a position of the first tissue portion and the second tissue portion with respect to one another.

23. The method of claim 22, wherein the first member includes a first end, a second end, and a length and a longitudinal axis extending between the first end and the second end, and wherein, when changing the orientation of the first member, the first member is rotated relative to the elongate member.

24. A method of securing tissues of a body of a patient, the method comprising:
    utilizing an elongate member connected to a first member and a second member;
    positioning a tubular member with respect to one of a first tissue portion and a second tissue portion of the body;
    passing the first member through the tubular member;
    passing the first member through at least portions of the first tissue portion and the second tissue portion;
    changing the orientation of the first member relative to the elongate member; and
    tensioning the elongate member to maintain a position of the first tissue portion and the second tissue portion with respect to one another.

25. The method of claim 24, wherein the first member includes a first end, a second end, and a length and a longitudinal axis extending between the first end and the second end, and wherein, when changing the orientation of the first member, the first member is rotated relative to the elongate member.

26. A method of securing a first body tissue and a second body tissue of a patient to each other, the method comprising:
    utilizing a first device having a first end and an opposite second end, a length and a longitudinal axis extending between the first and second ends, and a first side and a second side and a dimension therebetween, the length being greater than the dimension between the first side and the second side, the first device having an opening located proximate a midpoint of the length and extending through the first side and the second side, the opening having a suture located therein and the suture having at least one of a first portion and a second portion extending therefrom;
    applying a force to the first device with a second device to move the first device through a surface of one of the first and second body tissues and through at least a portion of the first and second body tissues along a direction of insertion that is approximately parallel to the longitudinal axis of the first device;
    rotating the first device to position the longitudinal axis of the first device transverse to the direction of insertion; and
    positioning a fastener adjacent to the surface of the one of the first and second body tissues and using the fastener to maintain tension in the first and second portions of the suture.

27. The method of claim 26, further including drilling a hole along the direction of insertion of the first device in at least one of the first and second body tissues of the patient.

28. The method of claim 26, wherein the applying the force to move the first device through the at least a portion of the first and second body tissues further includes passing the first device through a cylindrical opening in a third device.

\* \* \* \* \*

UNITED STATES PATENT AND TRADEMARK OFFICE
CERTIFICATE OF CORRECTION

| | | |
|---|---|---|
| PATENT NO. | : 8,845,699 B2 | Page 1 of 1 |
| APPLICATION NO. | : 13/413393 | |
| DATED | : September 30, 2014 | |
| INVENTOR(S) | : Peter M. Bonutti | |

It is certified that error appears in the above-identified patent and that said Letters Patent is hereby corrected as shown below:

On Title Page 1, Item 57 Abstract:
Column 2, line 6, change "hone" to --bone--;
Column 2, line 11, change "hone" to --bone--.

In the Claims:
Column 20
Line 1, Claim 9, change "portion" to --position--.

Signed and Sealed this
Tenth Day of February, 2015

Michelle K. Lee
*Deputy Director of the United States Patent and Trademark Office*